US012521399B2

(12) United States Patent
Deng et al.

(10) Patent No.: US 12,521,399 B2
(45) Date of Patent: *Jan. 13, 2026

(54) COMPOUND AS VOLTAGE-GATED SODIUM CHANNEL INHIBITOR

(71) Applicant: Guangzhou Fermion Technology Co., Ltd., Guangzhou (CN)

(72) Inventors: Daiguo Deng, Guangzhou (CN); Wenhe Zhong, Guangzhou (CN); Jielian Lu, Guangzhou (CN); Zengrong Lei, Guangzhou (CN)

(73) Assignee: Guangzhou Fermion Technology Co., Ltd., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/080,373

(22) Filed: Mar. 14, 2025

(65) Prior Publication Data

US 2025/0262220 A1 Aug. 21, 2025

Related U.S. Application Data

(63) Continuation of application No. 18/879,544, filed as application No. PCT/CN2023/112584 on Aug. 11, 2023.

(30) Foreign Application Priority Data

Aug. 12, 2022 (CN) ......................... 202210971471.1
Sep. 15, 2022 (CN) ......................... 202211124412.7

(51) Int. Cl.
*A61K 31/55* (2006.01)
*C07D 401/12* (2006.01)

(52) U.S. Cl.
CPC ............ *A61K 31/55* (2013.01); *C07D 401/12* (2013.01)

(58) Field of Classification Search
CPC .............................. A61K 31/55; C07D 401/12
See application file for complete search history.

(56) References Cited

U.S. PATENT DOCUMENTS

2025/0154109 A1* 5/2025 Bajji ....................... A61P 29/00

FOREIGN PATENT DOCUMENTS

| | | | |
|---|---|---|---|
| CN | 101466665 | A | 6/2009 |
| CN | 101855210 | A | 10/2010 |
| CN | 105683157 | A | 6/2016 |
| CN | 112457294 | A | 3/2021 |
| CN | 114031518 | A | 2/2022 |
| CN | 114437062 | A | 5/2022 |
| CN | 117069694 | A | 11/2023 |
| WO | 2021188880 | A1 | 9/2021 |
| WO | 2023138599 | A1 | 7/2023 |
| WO | 2023150201 | A2 | 8/2023 |
| WO | 2023211990 | A1 | 11/2023 |

OTHER PUBLICATIONS

PCT/CN2023/112584 International Search Report and Written Opinion, mailed Nov. 16, 2023, 20 pages.

* cited by examiner

*Primary Examiner* — James H Alstrum-Acevedo
*Assistant Examiner* — Manahil Mirghani Ali Abdalhameed
(74) *Attorney, Agent, or Firm* — Goodwin Procter LLP

(57) ABSTRACT

Provided are a compound as a voltage-gated sodium channel inhibitor, a preparation method therefor, a pharmaceutical composition thereof, and a use thereof. The compound has the structural characteristics of formula (I).

(I)

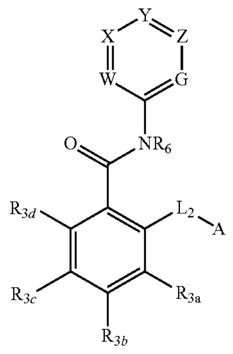

6 Claims, No Drawings

COMPOUND AS VOLTAGE-GATED SODIUM CHANNEL INHIBITOR

TECHNICAL FIELD

The present invention relates to a compound as a voltage-gated sodium channel inhibitor, a preparation method therefor, a pharmaceutical composition thereof, and a use thereof. The compound has the structural characteristics of formula (I).

BACKGROUND

There are mainly nine subtypes of human Nav, namely Nav1.1 to Nav1.9, respectively. The Nav subtypes are classified as TTX-sensitive (TTX-S) and TTX-insensitive (TTX-R), depending on whether they can be effectively inhibited by nanomoles of tetrodotoxin (TTX). The tissue expressions of the different subtypes vary greatly.

Nav1.1, Nav1.2, Nav1.3, Nav1.4, Nav1.6, and Nav1.7 are of the TTX-S type. Nav1.1, Nav1.2, and Nav1.3 are abundantly expressed in the central nervous system (CNS), Nav1.4 is abundantly present in skeletal muscle, and Nav1.6 and Nav1.7 are mainly abundantly present in the central nervous system.

Nav1.5, Nav1.8, and Nav1.9 are of the TTX-R type. Nav1.5 is mainly present in cardiomyocytes, and Nav1.8 and Nav1.9 are present in the dorsal root ganglia of the peripheral nervous system (PNS-DRG).

TABLE 1

Information of Nav subtypes

| Channel | Encoding gene | TTX $IC_{50}$ (nm) | Tissue for expression |
|---|---|---|---|
| Nav1.1 | SCN1A | 6 | Central nervous system |
| Nav1.2 | SCN2A | 13 | Central nervous system |
| Nav1.3 | SCN3A | 4 | Central nervous system |
| Nav1.4 | SCN4A | 5 | Skeletal muscle |
| Nav1.5 | SCN5A | 2000 | Cardiomyocytes |
| Nav1.6 | SCN8A | 3 | Central nervous system, neuroglia, dorsal root ganglia |
| Nav1.7 | SCN9A | 4 | Central nervous system, dorsal root ganglia |
| Nav1.8 | SCN10A | 31000 | Dorsal root ganglia |
| Nav1.9 | SCN11A | 1500 | Dorsal root ganglia |

Studies have shown that ion channel changes are a molecular basis for peripheral sensitization, central sensitization, and de-inhibition following inflammation or neuropathological injuries, and are also an important molecular mechanism for pain genesis. At present, Nav inhibitors have been proven to be effective. For example, the local anesthetic lidocaine relieves pain by inhibiting Nav, and non-selective Nav inhibitors such as lamotrigine, lacosamide, and mexiletine have been used successfully for the treatment of chronic pain. However, due to lack of subtype selectivity, the Nav inhibitors currently clinically used can inhibit sodium ion channels expressed in the heart and the central nervous system. The therapeutic window is narrow, and the application range is limited.

Highly selective Nav inhibitors represent one of the key directions for the research and development of voltage-gated sodium ion channels. Since Nav1.8 is mainly distributed in the peripheral nervous system and is localized in pain-sensing neurons, it is a highly selective target of action for pain treatment. Therefore, selective inhibition of Nav1.8 has good prospects for reducing potential toxic side effects.

Nav1.8 is a subtype of voltage-gated sodium ion channels (VGSC/Nav).

Nav1.8 is involved in the process of conduction and transmission of nociceptive action potential. Nav1.8 is the main mediator in the rising phase of the action potential due to its depolarized voltage dependence, and Nav1.8 also contributes to repeated high-frequency emission due to its ability to rapidly recover from inactivation. The propagation of pain sensation can be blocked by inhibiting the activity of Nav1.8, and since Nav1.8 is predominantly expressed in neurons that transmit pain signals in the dorsal root ganglia (DRG) of the peripheral nervous system, selective inhibition of Nav1.8 can also effectively reduce potential toxic side effects.

There is currently a need for a drug with superior activity as a voltage-gated sodium channel inhibitor that particularly selectively inhibits Nav1.8, thereby providing therapeutic benefits in the treatment of diseases.

SUMMARY

On the basis of the foregoing, the present invention provides a compound as a voltage-gated sodium channel inhibitor. The compound has the activity of selectively inhibiting Nav1.8, and is therefore useful in the treatment of a variety of diseases mediated by the same, especially various types of pain.

The present invention provides a compound represented by general formula (I), or a pharmaceutically acceptable salt, enantiomer, diastereomer, racemate, solvate, hydrate, polymorph, prodrug, or isotopic variant thereof:

(I)

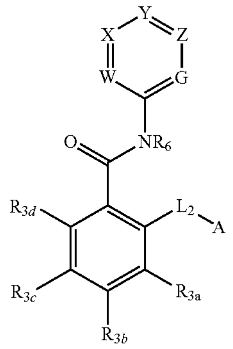

wherein each substituent is as defined in the present invention.

In one embodiment, the present invention provides a pharmaceutical composition comprising the compound as defined herein or the pharmaceutically acceptable salt, enantiomer, diastereomer, racemate, solvate, hydrate, polymorph, prodrug, or isotopic variant thereof, and a mixture thereof, and a pharmaceutically acceptable excipient. Preferably, the pharmaceutical composition further comprises other therapeutic agents.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same in the preparation of a medicament as a voltage-gated sodium channel inhibitor.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same in the preparation of a medicament as a sodium ion channel 1.8 (Nav1.8) inhibitor.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same as a voltage-gated sodium channel inhibitor.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same as a sodium ion channel 1.8 (Nav1.8) inhibitor.

In one embodiment, the present invention provides a method for inhibiting a voltage-gated sodium channel in a subject, comprising administering to the subject the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same.

In one embodiment, the present invention provides a method for inhibiting sodium ion channel 1.8 (Nav1.8) in a subject, comprising administering to the subject the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same.

The voltage-gated sodium channel inhibitor according to the present invention is useful in the treatment of a disease selected from: acute, chronic, neuropathic, or inflammatory pain, arthritis, migraine, cluster headache, trigeminal neuralgia, herpetic neuralgia, generalized neuralgia, epilepsy or epilepsy conditions, neurodegenerative diseases, psychiatric disorders such as anxiety and depression, bipolar disorder, muscular rigidity, arrhythmia, movement disorders, neuroendocrine disorders, ataxia, multiple sclerosis, irritable bowel syndrome, incontinence, visceral pain, osteoarthritic pain, postherpetic neuralgia, diabetic neuropathy, radiculalgia, sciatica, back pain, headache, neck pain, severe or intractable pain, nociceptive pain, penetrating pain, postoperative pain, cancer pain, stroke, cerebral ischemia, traumatic brain injury, amyotrophic lateral sclerosis, stress- or exercise-induced angina, heart palpitation, hypertension, migraine, or abnormal gastrointestinal activity.

In some embodiments, the disease relating to the present method is selected from radiculalgia, sciatica, back pain, headache, neck pain, intractable pain, acute pain, postoperative pain, back pain, tinnitus, or cancer pain.

DETAILED DESCRIPTION

Definitions

The compound, preparation method therefor, and pharmaceutical composition and use thereof of the present invention will be described in further detail below with reference to specific examples. The present invention may be implemented in many different forms and is not limited to the embodiments described herein. On the contrary, these embodiments are provided for the purpose of providing a thorough and complete understanding of the present disclosure.

Unless otherwise defined, all technical and scientific terms used herein have the meaning commonly understood by those of ordinary skill in the art. The terms used herein in the description are for the purpose of describing particular embodiments only and are not intended to limit the present invention. As used herein, the term "and/or" means any and all combinations of one or more of associated listed items.

Unless stated to the contrary, terms used in the description and claims have the following meanings.

Elements involved in the groups and compounds described in the present invention include carbon, hydrogen, oxygen, sulfur, nitrogen, or halogens, including their isotopes. Further, the elements carbon, hydrogen, oxygen, sulfur, or nitrogen involved in the groups and compounds of the present invention are optionally further replaced by one or more isotopes corresponding thereto. The isotopes of carbon include $^{12}C$, $^{13}C$, and $^{14}C$, the isotopes of hydrogen include protium (H), deuterium (D, or heavy hydrogen), and tritium (T, or superheavy hydrogen), the isotopes of oxygen include $^{16}O$, $^{17}O$, and $^{18}O$, the isotopes of sulfur include $^{32}S$, $^{33}S$ $^{34}S$, and $^{36}S$, the isotopes of nitrogen include $^{14}N$ and $^{15}N$, the isotopes of fluorine include $^{19}F$, the isotopes of chlorine include $^{35}Cl$, $^{36}Cl$, and $^{37}Cl$, and the isotopes of bromine include $^{79}Br$ and $^{81}Br$.

The term "alkyl" refers to a saturated straight or branched chain aliphatic hydrocarbon group, specifically a saturated hydrocarbon containing a primary (normal) carbon atom, a secondary carbon atom, a tertiary carbon atom, a quaternary carbon atom, or a combination thereof. A phrase containing the term, e.g., "$C_{1-6}$ alkyl" refers to an alkyl containing 1 to 6 carbon atoms, and each occurrence thereof may be independently a $C_1$ alkyl, a $C_2$ alkyl, a $C_3$ alkyl, a $C_4$ alkyl, a $C_5$ alkyl, or a $C_6$ alkyl. One of embodiments may comprise an alkyl containing 1 to 20 carbon atoms, preferably an alkyl containing 1 to 10 carbon atoms, and more preferably a lower alkyl containing 1 to 6 carbon atoms or 1 to 4 carbon atoms. Non-limiting examples of the alkyl include: methyl, ethyl, 1-propyl, 2-propyl (i-Pr, i-propyl, $-CH(CH_3)_2$), 1-butyl (n-Bu, n-butyl, $-CH_2CH_2CH_2CH_3$), 2-methyl-prop-1-yl (i-Bu, i-butyl, $-CH_2CH(CH_3)_2$), 2-butyl (s-Bu, sec-butyl, $-CH(CH_3)CH_2CH_3$), 2-methyl-prop-2-yl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-but-2-yl ($-C(CH_3)_2CH_2CH_3$), 3-methyl-but-2-yl ($-CH(CH_3)CH(CH_3)_2$), 3-methyl-but-1-yl ($-CH_2CH_2CH(CH_3)_2$), 2-methyl-but-1-yl ($-CH_2CH(CH_3)CH_2CH_3$), 1-hexyl ($-CH_2CH_2CH_2CH_2CH_2CH_3$), hex-2-yl ($-CH(CH_3)CH_2CH_2CH_2CH_3$), hex-3-yl ($-CH(CH_2CH_3)(CH_2CH_2CH_3)$), 2-methyl-pent-2-yl ($-C(CH_3)_2CH_2CH_2CH_3$), 3-methyl-pent-2-yl ($-CH(CH_3)CH(CH_3)CH_2CH_3$), 4-methyl-pent-2-yl ($-CH(CH_3)CH_2CH(CH_3)_2$), 3-methyl-pent-3-yl ($-C(CH_3)(CH_2CH_3)_2$, 2-methyl-pent-3-yl ($-CH(CH_2CH_3)CH(CH_3)_2$), 2,3-dimethyl-but-2-yl ($-C(CH_3)_2CH(CH_3)_2$), 3,3-dimethyl-but-2-yl ($-CH(CH_3)C(CH_3)_3$, octyl ($-(CH_2)_7CH_3$), and n-nonyl, and various branched isomers thereof. The alkyl may be substituted or unsubstituted. When the alkyl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Alkenyl" is an alkyl as defined herein containing at least one carbon-carbon double bond. In one example, the alkenyl contains 2 to 20 carbon atoms, preferably 2 to 12 carbon atoms, more preferably 2 to 8 carbon atoms, and still more preferably 2 to 6 carbon atoms. Non-limiting examples of the alkenyl include substituted or unsubstituted vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, or 4-decenyl, etc. When the alkenyl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Alkynyl" is an alkyl as defined herein containing at least one carbon-carbon triple bond. In one example, the alkynyl contains 2 to 20 carbon atoms, preferably 2 to 12 carbon atoms, more preferably 2 to 8 carbon atoms, and still more preferably 2 to 6 carbon atoms. Non-limiting examples of the alkynyl include substituted or unsubstituted ethynyl, 1-propynyl, 2-propynyl, 1-butynyl, 2-butynyl, 3-butynyl, 4-pentynyl, 3-pentynyl, 2-hexynyl, 3-hexynyl, 3-butynyl, 2-heptynyl, 3-heptynyl, 4-heptynyl, 3-octynyl, 3-nonynyl, or 4-decynyl, etc. When the alkynyl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Cycloalkyl" refers to a saturated or partially unsaturated monocyclic or polycyclic carbon-containing group. In one embodiment, the cycloalkyl is a 3- to 6-membered ($C_{3-6}$) monocyclic, 3- to 8-membered ($C_{3-8}$) monocyclic, 3- to 10-membered ($C_{3-10}$) monocyclic, 4- to 12-membered bicyclic ($C_{4-12}$), or 10- to 15-membered ($C_{10-15}$) tricyclic system. The carbocycle includes a bridged ring or a spiro ring. Non-limiting examples of the cycloalkyl include cyclopropyl, cyclobutyl, cyclopentyl, cyclohexyl, cyclohexenyl, cycloheptyl, cyclopentenyl, cyclohexadienyl, cycloheptatrienyl, etc. The cycloalkyl may be optionally substituted. When the cycloalkyl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Heterocyclyl" or "heterocycle" refers to a substituted or unsubstituted, saturated or partially unsaturated, monocyclic or polycyclic group containing a heteroatom selected from N, O, and S. In one embodiment, the heterocyclyl may be a 3- to 8-membered monocyclic, 4- to 12-membered bicyclic, or 10- to 15-membered tricyclic system. The heterocyclyl is preferably a 3- to 10-membered monocyclic or bicyclic heterocyclyl, more preferably a 5- to 8-membered monocyclic or bicyclic heterocyclyl, and contains at least one, preferably 1 to 4, 1 to 3, or 1 to 2 heteroatoms selected from N, O, or S. The heteroatom N or S in the heterocycle, if present, may be oxidized to various oxidation states to form, for example, N-oxides. The heterocycle may be attached to other moieties of the molecule via a heteroatom or a carbon atom. The heterocycle includes a bridged ring or a spiro ring. Non-limiting examples of the monocyclic heterocycle include oxirane, aziridinyl, oxetanyl, azetidinyl, 1,3-dioxolanyl, dihydrofuranyl, tetrahydrofuranyl, tetrahydropyrrolyl, tetrahydroimidazolyl, tetrahydrothiazolyl, dithiolanyl, oxacyclohexyl, thiacyclohexyl, azacyclohexyl, azepanyl, diazepanyl, morpholinyl, thiomorpholinyl, dihydropyranyl, tetrahydropyranyl, dihydropyridyl, tetrahydrothienyl, thiooxidized tetrahydrothienyl, etc. Non-limiting examples of the bicyclic heterocyclyl include benzodihydrofuran, tetrahydroquinolinyl, tetrahydroisoquinolinyl, indolinyl, octahydrocyclopentadienopyrrole, octahydropyrrolopyrrolyl, octahydrocyclopentadienyl, etc.

When the heterocyclyl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Aryl" refers to a substituted or unsubstituted all-carbon monocyclic or fused polycyclic unsaturated group having a conjugated π electron system. In one embodiment, the aryl is a 6- to 14-membered aromatic ring, preferably a 6- to 10-membered aromatic ring. Non-limiting examples of the aryl include phenyl or naphthyl. The aryl may be fused to a heteroaryl, heterocyclyl, or cycloalkyl, and the site of attachment to the moiety of the molecule is on the aryl. Non-limiting examples of the aryl include benzene. When the aryl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Heteroaryl" refers to a substituted or unsubstituted monocyclic or fused polycyclic unsaturated group containing at least one heteroatom selected from N, O, and S. In one embodiment, the heteroaryl is a 5- to 15-membered heteroaromatic ring, a 5- to 14-membered heteroaryl, or preferably a 5- to 10-membered heteroaromatic ring, or more preferably a 5- to 6-membered heteroaryl, wherein the number of heteroatoms is 1 to 4, preferably 1 to 3, and more preferably 1 to 2. Non-limiting examples of the heteroaryl include pyrrolyl, furanyl, thienyl, N-alkylpyrrolyl, imidazolyl, pyridinyl, pyrimidinyl, pyrazinyl, pyridazinyl, benzofuran, benzimidazole, benzopyridine, or pyrrolopyridine, etc. When the heteroaryl is substituted, unless otherwise defined, there are preferably 1 to 5 substituents, and the substituents are independently selected from F, Cl, Br, I, ═O, an alkyl, an alkenyl, an alkynyl, an alkoxy, a hydroxy, a nitro, a cyano, and an amino.

"Halogen" means F, Cl, Br, or I. "Halogenated" refers to replacement of one or more hydrogen atoms in a molecule or group with a halogen selected from F, Cl, Br, or I.

In various sections of the present invention, linking substituents are described. When a structure clearly requires a linking group, Markush variables listed for that group should be understood as linking groups. For example, if a structure requires a linking group, and a Markush group definition for this variable lists "alkyl" or "aryl", it should be understood that the "alkyl" or "aryl" respectively represents a linking alkylene group or arylene group. In some specific structures, when the alkyl group is explicitly expressed as a linking group, the alkyl group represents a linking alkylene group, for example, the alkyl in the group "—$C_1$-$C_3$ haloalkyl" should be understood as an alkylene.

"Pharmaceutically acceptable salt" refers to a pharmaceutically acceptable salt of a non-toxic acid or base, including salts formed with inorganic acids or bases, or salts formed with organic acids and organic bases. Salts derived from inorganic bases include, but are not limited to, metal salts formed with Al, Ca, Li, Mg, K, Na, and Zn. Salts derived from organic bases include, but are not limited to, salts formed with primary, secondary, or tertiary amines. The primary, secondary, or tertiary amines include naturally occurring substituted or unsubstituted amines, cyclic amines, and basic ion exchange resins, such as ammonia, isopropylamine, trimethylamine, diethylamine, triethylamine, tripropylamine, diethanolamine, ethanolamine, dimethylethanolamine, 2-dimethylaminoethanol, 2-diethylaminoethanol, dicyclohexylamine, caffeine, procaine, choline, betaine, benethamine penicillin, ethylene diamine, glucosamine, methylglucosamine, theobromine, triethanolamine, trometamol, purine, piperizine, piperidine, N-ethylpiperidine, or polyamine resins. Salts derived from inorganic and organic acids include, but are not limited to, salts formed with the following acids: sulfuric acid, phosphoric acid, nitric acid, hydrobromic acid, hydrochloric acid, formic acid, acetic acid, propionic acid, benzenesulfonic acid, benzoic acid, phenylacetic acid, salicylic acid, alginic acid, anthranilic acid, camphoric acid, citric acid, vinyl sulfonic acid, formic acid, fumaric acid, furoic acid, gluconic acid, glucuronic acid, glutamic acid, glycolic acid, isethionic acid, lactic acid, maleic acid, malic acid, mandelic acid, mucic acid, pamoic acid, pantothenic acid, stearic acid, succinic acid, sulfanilic acid, tartaric acid, p-toluenesulfonic acid, malonic acid, 2-hydroxypropionic acid, oxalic acid, glycolic acid, glucuronic acid, galacturonic acid, citric acid, lysine, arginine, aspartic acid, cinnamic acid, p-toluenesulfonic acid, methanesulfonic acid, ethanesulfonic acid, or trifluoromethanesulfonic acid, etc.

The term "solvate", which may also be referred to as "solvent compound", refers to a compound that contains a solvent molecule, which may be bound to the compound molecule in ways including coordination bonds, covalent bonds, van der Waals forces, ionic bonds, hydrogen bonds, etc. Common solvents include water, methanol, ethanol, acetic acid, DMSO, THF, diethyl ether, etc. The compounds described herein can be prepared, e.g., in crystalline forms, and can be solvated. Suitable solvates include pharmaceutically acceptable solvates and further include stoichiometric and non-stoichiometric solvates. In some cases, the solvate will be capable of being isolated, for example, when one or more solvent molecules are incorporated into crystal lattices of a crystalline solid. The "solvate" includes solvates in solution and isolatable solvates. Representative solvates include hydrates, ethanolates, and methanolates.

The term "hydrate" refers to a compound that is bound to water. In general, the ratio of the number of water molecules contained in a hydrate of a compound to the number of compound molecules in the hydrate is determinate. Thus, a hydrate of a compound may be represented by a general formula such as R·x $H_2O$, where R is the compound and x is a number greater than 0. A given compound may form more than one type of hydrate, including, for example, a monohydrate (x is 1), a lower hydrate (x is a number greater than 0 and less than 1, e.g., a hemihydrate (R·0.5 $H_2O$)), and a polyhydrate (x is a number greater than 1, e.g., a dihydrate (R·2 $H_2O$) and a hexahydrate (R·6 $H_2O$)).

The term "prodrug" refers to any compound that when administered to an organism generates a drug substance, i.e., an active ingredient, as a result of a spontaneous chemical reaction, an enzyme catalyzed chemical reaction, photolysis, and/or a metabolic chemical reaction. A prodrug is thus a covalently modified analog or latent form of a therapeutically active compound. Suitable examples include, but are not limited to, the following forms of a compound: carboxylate ester, carbonate ester, phosphate ester, nitrate ester, sulfate ester, sulfone ester, sulfoxide ester, amino compound, carbamate salt, azo compound, phosphoramide, glucoside, ether, acetal, etc.

The present invention also includes isotopically labeled compounds (isotopic variants), which are equivalent to those general formula compounds or particular compounds in the present application except that one or more atoms are replaced by atoms having an atomic mass or mass number different from the atomic mass or mass number usually found in nature. Examples of isotopes that can be incorporated into the compounds of the present invention include isotopes of hydrogen, carbon, nitrogen, oxygen, phosphorous, sulfur, fluorine, and chloride, such as $^{2}H$, $^{3}H$, $^{13}C$, $^{11}C$, $^{14}C$, $^{15}N$, $^{1}$80, $^{17}$, $^{31}P$, $^{32}P$, $^{35}S$, i$^{8}$F, and $^{36}Cl$, respectively, and preferably $^{2}H$ (that is, deuterium, D). The compounds of the present invention which contain the aforementioned isotopes and/or other isotopes of other atoms, prodrugs thereof, and pharmaceutically acceptable salts of the compounds or the prodrugs are all within the scope of the present invention. Certain isotopically labeled compounds of the present invention, for example those into which radioactive isotopes (such as $^{3}H$ and $^{14}C$) are incorporated, are useful in drug and/or substrate tissue distribution assays. Tritium, i.e., 3H and carbon-14, i.e., $^{14}C$ isotopes are particularly preferred due to their ease of preparation and detectability. Further, substitution with heavier isotopes such as deuterium (i.e., $^{2}H$) may be preferred in some cases since substituted compounds may afford certain therapeutic advantages by virtue of greater metabolic stability, for example prolonged in-vivo half-life or reduced dosage requirements. The isotopically labeled compounds of the present invention and prodrugs thereof can generally be prepared by substituting a readily available isotopically labeled reagent for a non-isotopically labeled reagent when carrying out the processes disclosed in the following procedures and/or examples and preparative examples.

The compounds of the present invention include one or more asymmetric centers, and thus may have multiple stereoisomer forms, e.g., enantiomer and/or diastereomer forms. For example, the compounds of the present invention may be a separate enantiomer, diastereomer, or geometric isomer (e.g., cis- and trans-isomers), or may be in the form of a mixture of stereoisomers, including a mixture of racemates and a mixture rich in one or more stereoisomers. The isomers may be separated from the mixture by methods known to those skilled in the art, including: chiral high pressure liquid chromatography (HPLC) and formation and crystallization of chiral salts. Alternatively, preferred isomers may be prepared by asymmetric synthesis.

"Optional" or "optionally" means that a subsequently described event or circumstance may, but not necessarily, occur, including cases where the event or circumstance does or does not occur. For example, "an aryl is optionally substituted with an alkyl" means that the alkyl may, but not necessarily, be present, and the term includes instances where the aryl is substituted with an alkyl and instances where the aryl is not substituted with an alkyl.

"Pharmaceutically acceptable excipient" refers to a pharmaceutically acceptable material, composition, or agent, such as a liquid or solid filler, a diluent, an excipient, a solvent, or an encapsulating material. As used herein, the term "pharmaceutically acceptable excipient" includes buffers, sterile water for injection, solvents, dispersion media, coatings, antibacterial and antifungal agents, isotonicity agents, and absorption retarders, etc., compatible with pharmaceutical administration. Each excipient needs to be "pharmaceutically acceptable" in the sense of being compatible with other ingredients in a formulation and not harmful to a patient. Suitable examples include, but are not limited to: (1) sugars such as lactose, glucose, and sucrose; (2) starches such as corn starch, potato starch, and substituted or unsubstituted β-cyclodextrin; (3) cellulose and its derivatives such as sodium carboxymethyl cellulose, ethyl cellulose, and cellulose acetate; (4) powdered tragacanth; (5) malt; (6) gelatin; (7) talc; (8) excipients such as cocoa butter and suppository wax; (9) oils such as peanut oil, cottonseed oil, safflower oil, sesame oil, olive oil, corn oil, and soybean oil; (10) diols, such as propylene glycol; (11) polyols such as glycerin, sorbitol, mannitol, and polyethylene glycol; (12) esters such as ethyl oleate and ethyl laurate; (13) agar; (14) buffering agents such as magnesium hydroxide and aluminum hydroxide; (15) alginic acid; (16) pyrogen-free water; (17) isotonic saline; (18) Ringer's solution; (19) ethanol; (20) phosphate buffers; and (21) other non-toxic compatible substances used in drug formulations.

The term “polymorph” refers to a crystalline form of a compound (or a salt, hydrate, or solvate thereof) of a particular crystal packing arrangement. All polymorphs have the same elemental composition. Different crystalline forms typically have different X-ray diffraction patterns, infrared spectra, melting points, densities, hardness, crystal shapes, optoelectronic properties, stability, and solubility. Recrystallization solvent, rate of crystallization, storage temperature, and other factors can cause one crystalline form to dominate. Various polymorphs of a compound can be prepared by crystallization under different conditions.

Unless otherwise specified, all technical terms and scientific terms used herein have the standard meanings in the field to which the claimed subject matter belongs. In the event that there are multiple definitions for a term, the definition herein shall prevail. It should be understood that the singular forms used in the present invention, such as “a”, “an”, and “one”, include plural referents, unless otherwise specified.

Furthermore, the terms “comprise” and “include” are open-ended rather than closed-ended limitations, that is, they include the content specified in the present invention, but do not exclude the content of other aspects.

Unless otherwise indicated, the present invention uses conventional methods such as mass spectrometry, nuclear magnetic spectrometry, etc., to identify compounds, and for steps and conditions, reference can be made to conventional operating steps and conditions in the art.

Unless otherwise specified, the present invention employs standard nomenclature and standard laboratory steps and techniques in analytical chemistry, organic synthetic chemistry, and optics. In some cases, standard techniques are used for chemical synthesis, chemical analysis, and testing of the performance of light-emitting devices.

In addition, it should be noted that unless explicitly stated otherwise, the expression “ . . . respectively independently” used in the present invention should be understood in a broad sense, meaning that the entities described are independent of each other, and may independently be the same specific group or different specific groups. In more detail, the expression “ . . . respectively independently” may mean that in different groups, specific options expressed by the same symbols do not affect each other, or may mean that in the same group, specific options expressed by the same symbols do not affect each other.

The dosage form and administration route of the compounds of the present invention or the compositions thereof are not particularly limited.

Representative administration routes include, but are not limited to: oral, intratumoral, rectal, parenteral (intravenous, intraperitoneal, intramuscular, or subcutaneous) injection, and/or topical administration.

Solid dosage forms for oral administration include capsules, tablets, pills, powders, and granules. In these solid dosage forms, the active compound is mixed with at least one conventional inert excipient (or carrier), such as sodium citrate or dicalcium phosphate, or is mixed with the following components: (a) a filler or compatilizer, for example, starch, lactose, sucrose, glucose, mannitol, and silicic acid; (b) a binder, for example, hydroxymethylcellulose, alginate, gelatin, polyvinylpyrrolidone, sucrose, and gum arabic; (c) a humectant, for example, glycerin; (d) a disintegrant, for example, agar, calcium carbonate, potato or tapioca starch, alginic acid, complex silicate. and sodium carbonate; (e) a solvent, for example, paraffin; (f) an absorption accelerator, for example, a quaternary ammonium compound; (g) a wetting agent, for example, cetyl alcohol and glyceryl monostearate; (h) an adsorbent, for example, kaolin; and (i) a lubricant, for example, talc, calcium stearate, magnesium stearate, solid polyethylene glycol, sodium lauryl sulfate, or mixtures thereof.

Liquid dosage forms for oral administration include pharmaceutically acceptable emulsions, solutions, suspensions, syrups, or tinctures. In addition to the active compounds, liquid dosage forms can contain inert diluents (e.g., water or other solvents), solubilizers, and emulsifiers conventionally used in the art. Specific examples are, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil, and sesame oil, or mixtures of these substances. Besides inert diluents, the compositions may further contain adjuvants such as wetting agents, suspending agents, sweeteners, flavors, and perfuming agents. For example, suspensions may contain suspending agents. Specific examples are, for example, ethoxylated isostearyl alcohol, polyoxyethylene sorbitol and sorbitan esters, microcrystalline cellulose, aluminum methoxide and agar, or mixtures thereof.

Compositions for parenteral injection may include physiologically acceptable sterile aqueous or anhydrous solutions, dispersions, suspensions, or emulsions, and sterile powders for reconstitution into sterile injectable solutions or dispersions. Suitable aqueous or non-aqueous carriers, diluents, solvents, or excipients are selected from water, ethanol and polyols, or suitable mixtures thereof.

Dosage forms for topical administration include ointments, powders, patches, sprays, and inhalants, which are prepared by mixing active ingredients with a pharmaceutically acceptable carrier together with a preservative, a buffer, and/or a propellant as required under sterile conditions.

The present invention relates to the following embodiments.

In one embodiment, the present invention relates to a compound represented by general formula (I'), or a pharmaceutically acceptable salt, enantiomer, diastereomer, racemate, solvate, hydrate, polymorph, prodrug, or isotopic variant thereof:

(I')

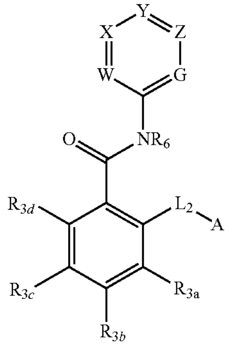

wherein:

X is N or $CR_x$;

Y is N or $CR_y$;

Z is N or $CR_z$;

W is N or $CR_w$;

G is N or $CR_g$;

with the proviso that at most two of X, Y, and Z are simultaneously N;

$R_x$, $R_y$, and $R_z$ are each independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, and -$L_1$-$R_1$, wherein at least one of $R_x$, $R_y$, and $R_z$ is -$L_1$-$R_1$, and the groups are optionally substituted with one or more deuteriums until fully deuterated;

$R_w$ and $R_g$ are each independently selected from H, D, a halogen, CN, a $C_{1-6}$ alkyl, a $C_{2-6}$ alkenyl, a $C_{2-6}$ alkynyl, a $C_{1-6}$ haloalkyl, and —$OR_{s1}$, and the groups are optionally substituted with one or more deuteriums until fully deuterated;

-$L_1$- is —$(CR_aR_b)_m$—, and, where valence allows, any methylene unit in —$(CR_aR_b)_m$— is optionally and independently replaced by —NR'—, —O—, —S—, and —C(O)—, and/or $R_a$ and $R_b$ together with the carbon atom to which they are attached form a $C_{3-8}$ cycloalkyl or a 3- to 10-membered heterocyclyl;

$R_1$ is —$S(O)_q$NR'R", —S(O)(=NR')$R_4$, or —N=S(O)$R_4R_4$';

A is selected from a $C_{3-8}$ cycloalkyl, a 3- to 10-membered heterocyclyl, a $C_{6-10}$ aryl, and a 5- to 10-membered heteroaryl, and is optionally substituted with s $R_2$ substituents;

-$L_2$- is selected from a bond, —O—, —NR'—, —S—, —C(O)—, and —$(CR_cR_d)_n$—, and, where valence allows, any methylene unit in —$(CR_cR_d)_n$— is optionally and independently replaced by —NR'—, —O—, —S—, and —C(O)—, and/or $R_c$ and $R_d$ together with the carbon atom to which they are attached form a $C_{3-8}$ cycloalkyl or a 3- to 10-membered heterocyclyl;

R' is selected from H, a $C_{1-6}$ alkyl, a $C_{2-6}$ alkenyl, a $C_{2-6}$ alkynyl, and a $C_{1-6}$ haloalkyl, and the group is optionally substituted with one or more deuteriums until fully deuterated;

R" is -$L_3$-B;

B is selected from a $C_{3-8}$ cycloalkyl, a 3- to 10-membered heterocyclyl, a $C_{6-10}$ aryl, and a 5- to 10-membered heteroaryl, and is optionally substituted with t $R_5$ substituents;

-$L_3$- is —$(CR_eR_f)_p$—, and, where valence allows, any methylene unit in —$(CR_eR_f)_p$ is optionally and independently replaced by —NR'—, —O—, —S—, and —C(O)—, and/or $R_e$ and $R_f$ together with the carbon atom to which they are attached form a $C_{3-8}$ cycloalkyl or a 3- to 10-membered heterocyclyl;

$R_2$, $R_{3a}$, $R_{3b}$, $R_{3c}$, and $R_{3d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, $NR_{s1}R_{s2}$, —C(O)$R_{s1}$, —C(O)$OR_{s1}$, —C(O)$NR_{s1}R_{s2}$, —$SOR_{s1}$, and —$SO_2R_{s1}$, and the groups are optionally substituted with one or more deuteriums until fully deuterated;

$R_4$ and $R_4$' are each independently selected from H, a $C_{1-6}$ alkyl, a $C_{2-6}$ alkenyl, a $C_{2-6}$ alkynyl, and a $C_{1-6}$ haloalkyl, and the groups are optionally substituted with one or more deuteriums until fully deuterated;

each $R_5$ is independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, NRs$R_{s2}$, —C(O)$R_{s1}$, —C(O)$OR_{s1}$, —C(O)$NR_{s1}R_{s2}$, —$SOR_{s1}$, and —$SO_2R_{s1}$, and the group is optionally substituted with one or more deuteriums until fully deuterated;

$R_6$ is selected from H, a $C_{1-6}$ alkyl, and a $C_{1-6}$ haloalkyl, and the group is optionally substituted with one or more deuteriums until fully deuterated;

$R_a$, $R_b$, $R_c$, $R_d$, $R_e$, and $R_f$ are independently selected from H, D, a halogen, CN, a $C_{1-6}$ alkyl, a $C_{2-6}$ alkenyl, a $C_{2-6}$ alkynyl, and a $C_{1-6}$ haloalkyl, and the groups are optionally substituted with one or more deuteriums until fully deuterated;

$R_{s1}$ and $R_{s2}$ are independently selected from H, a $C_{1-6}$ alkyl, and a $C_{1-6}$ haloalkyl, and the groups are optionally substituted with one or more deuteriums until fully deuterated;

m is 0, 1, 2, 3, 4, 5, or 6;

n is 0, 1, 2, 3, 4, 5, or 6;

p is 0, 1, 2, 3, 4, 5, or 6;

t is 1, 2, 3, 4, or 5;

s is 1, 2, 3, 4, 5, 6, 7, or 8; and q is 1 or 2.

In one embodiment, the present invention relates to a compound represented by general formula (I), or a pharmaceutically acceptable salt, enantiomer, diastereomer, racemate, solvate, hydrate, polymorph, prodrug, or isotopic variant thereof:

(I)

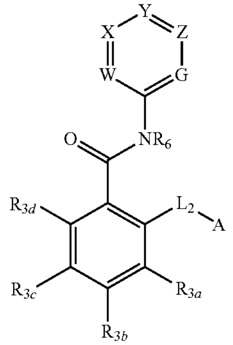

wherein:

X is N or $CR_x$;

Y is N or $CR_y$;

Z is N or $CR_z$;

W is N or $CR_w$;

G is N or $CR_g$;

with the proviso that at most two of X, Y, and Z are simultaneously N;

$R_x$, $R_y$, and $R_z$ are each independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, and -$L_1$-$R_1$, wherein at least one of $R_x$, $R_y$, and $R_z$ is -$L_1$-$R_1$, and the groups are optionally substituted with one or more deuteriums until fully deuterated;

$R_w$ and $R_g$ are each independently selected from H, D, a halogen, CN, a $C_{1-6}$ alkyl, a $C_{2-6}$ alkenyl, a $C_{2-6}$ alkynyl, a $C_{1-6}$ haloalkyl, and —$OR_{s1}$, and the groups are optionally substituted with one or more deuteriums until fully deuterated;

-$L_1$- is —$(CR_aR_b)_m$—, and, where valence allows, any methylene unit in —$(CR_aR_b)_m$— is optionally and independently replaced by —NR'—, —O—, —S—, and —C(O)—, and/or $R_a$ and $R_b$ together with the carbon atom to which they are attached form a $C_{3-8}$ cycloalkyl or a 3- to 10-membered heterocyclyl;

$R_1$ is —$S(O)_qNR'R''$ or —S(O)(=NR')$R_1$;

A is selected from a $C_{3-8}$ cycloalkyl, a 3- to 10-membered heterocyclyl, a $C_{6-10}$ aryl, and a 5- to 10-membered heteroaryl, and is optionally substituted with s $R_2$ substituents;

-$L_2$- is selected from a bond, —O—, —NR'—, —S—, —C(O)—, and —$(CR_cR_d)_n$—, and, where valence allows, any methylene unit in —$(CR_eR_d)_n$— is optionally and independently replaced by —NR'—, —O—, —S—, and —C(O)—, and/or $R_c$ and $R_d$ together with the carbon atom to which they are attached form a $C_{3-8}$ cycloalkyl or a 3- to 10-membered heterocyclyl;

R' is selected from H, a $C_{1-6}$ alkyl, a $C_{2-6}$ alkenyl, a $C_{2-6}$ alkynyl, and a $C_{1-6}$ haloalkyl, and the group is optionally substituted with one or more deuteriums until fully deuterated;

R'' is -$L_3$-B;

B is selected from a $C_{3-8}$ cycloalkyl, a 3- to 10-membered heterocyclyl, a $C_{6-10}$ aryl, and a 5- to 10-membered heteroaryl, and is optionally substituted with t $R_5$ substituents;

-$L_3$- is —$(CR_eR_f)_p$—, and, where valence allows, any methylene unit in —$(CR_eR_f)_p$— is optionally and independently replaced by —NR'—, —O—, —S—, and —C(O)—, and/or $R_e$ and $R_f$ together with the carbon atom to which they are attached form a $C_{3-8}$ cycloalkyl or a 3- to 10-membered heterocyclyl;

$R_2$, $R_{3a}$, $R_{3b}$, $R_{3c}$, and $R_{3d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, $NR_{s1}R_{s2}$, —C(O)$R_{s1}$, —C(O)$OR_{s1}$, —C(O)$NR_{s1}R_{s2}$, —$SOR_{s1}$, and —$SO_2R_{s1}$, and the groups are optionally substituted with one or more deuteriums until fully deuterated;

$R_4$ is selected from H, a $C_{1-6}$ alkyl, a $C_{2-6}$ alkenyl, a $C_{2-6}$ alkynyl, and a $C_{1-6}$ haloalkyl, and the group is optionally substituted with one or more deuteriums until fully deuterated;

each $R_5$ is independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, $NR_{s1}R_{s2}$, —C(O)$R_{s1}$, —C(O)$OR_{s1}$, —C(O)$NR_{s1}R_{s2}$, —$SOR_{s1}$, and —$SO_2R_{s1}$, and the group is optionally substituted with one or more deuteriums until fully deuterated;

$R_6$ is selected from H, a $C_{1-6}$ alkyl, and a $C_{1-6}$ haloalkyl, and the group is optionally substituted with one or more deuteriums until fully deuterated;

$R_a$, $R_b$, $R_c$, $R_d$, $R_e$, and $R_f$ are independently selected from H, D, a halogen, CN, a $C_{1-6}$ alkyl, a $C_{2-6}$ alkenyl, a $C_{2-6}$ alkynyl, and a $C_{1-6}$ haloalkyl, and the groups are optionally substituted with one or more deuteriums until fully deuterated;

$R_{s1}$ and $R_{s2}$ are independently selected from H, a $C_{1-6}$ alkyl, and a $C_{1-6}$ haloalkyl, and the groups are optionally substituted with one or more deuteriums until fully deuterated;

m is 0, 1, 2, 3, 4, 5, or 6;

n is 0, 1, 2, 3, 4, 5, or 6;

p is 0, 1, 2, 3, 4, 5, or 6;

t is 1, 2, 3, 4, or 5;

s is 1, 2, 3, 4, 5, 6, 7, or 8; and q is 1 or 2.

In one embodiment, the present invention relates to the compound represented by formula (I) or (I') above, or the pharmaceutically acceptable salt, enantiomer, diastereomer, racemate, solvate, hydrate, polymorph, prodrug, or isotopic variant thereof, which is formula (II), (II)

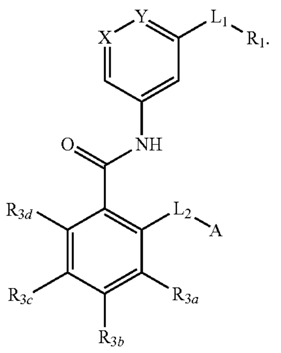

In one embodiment, the present invention relates to the compound represented by formula (I) or (II) above, or the pharmaceutically acceptable salt, enantiomer, diastereomer, racemate, solvate, hydrate, polymorph, prodrug, or isotopic variant thereof, wherein -$L_2$- is —O—.

In one embodiment, the present invention relates to the compound represented by formula (I) or (II) above, or the pharmaceutically acceptable salt, enantiomer, diastereomer, racemate, solvate, hydrate, polymorph, prodrug, or isotopic variant thereof, wherein -$L_2$- is a bond.

In one embodiment, the present invention relates to the compound described above, or the pharmaceutically acceptable salt, enantiomer, diastereomer, racemate, solvate, hydrate, polymorph, prodrug, or isotopic variant thereof, wherein A is selected from phenyl, a $C_{3-6}$ cycloalkyl, a 5- to 6-membered heteroaryl, and a 5- to 10-membered heterocyclyl.

In one embodiment, the present invention relates to the compound described above, or the pharmaceutically acceptable salt, enantiomer, diastereomer, racemate, solvate, hydrate, polymorph, prodrug, or isotopic variant thereof, wherein A is selected from cyclopentyl, cyclohexyl, azacyclohexyl, oxacyclohexyl, thiacyclohexyl, azepanyl, diazepanyl, octahydrocyclopentadienopyrrole, octahydropyrrolopyrrolyl, octahydrocyclopentadienyl, phenyl, pyrrolyl, furanyl, thienyl, pyridyl, pyrimidinyl, and pyridazinyl.

In one embodiment, the present invention relates to the compound described above, or the pharmaceutically acceptable salt, enantiomer, diastereomer, racemate, solvate, hydrate, polymorph, prodrug, or isotopic variant thereof, wherein m is 0.

In one embodiment, the present invention relates to the compound described above, or the pharmaceutically acceptable salt, enantiomer, diastereomer, racemate, solvate, hydrate, polymorph, prodrug, or isotopic variant thereof, wherein:

m is 1, 2, 3, 4, or 5, any methylene unit in —$(CR_aR_b)_m$— is optionally and independently replaced by —O—, —S—, and —C(O)—; and/or $R_a$ and $R_b$ together with the carbon atom to which they are attached form a $C_{3-6}$ cycloalkyl and a 3- to 5-membered heterocyclyl;

$R_a$ is selected from H, a $C_{1-6}$ alkyl, and a $C_{1-6}$ haloalkyl; and $R_b$ is selected from H, a $C_{1-6}$ alkyl, and a $C_{1-6}$ haloalkyl.

In one embodiment, the present invention relates to the compound represented by formula (I) above, or the pharmaceutically acceptable salt, enantiomer, diastereomer, racemate, solvate, hydrate, polymorph, prodrug, or isotopic variant thereof, which is formula (III), (III)

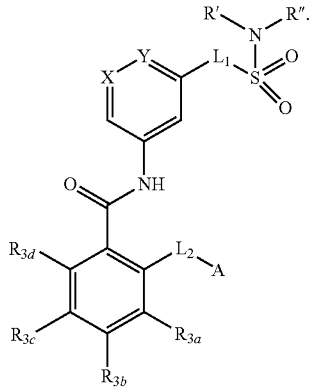

In one embodiment, the present invention relates to the compound represented by formula (I) above, or the pharmaceutically acceptable salt, enantiomer, diastereomer, racemate, solvate, hydrate, polymorph, prodrug, or isotopic variant thereof, which is formula (IV), (IV)

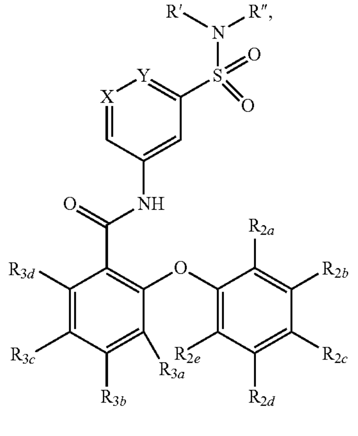

wherein:

X is N or $CR_x$;

Y is N or $CR_y$;

$R_x$ and $R_y$ are each independently selected from H, D, a halogen, a $C_{1-6}$ alkyl, or a $C_{1-6}$ haloalkyl, and the groups are optionally substituted with one or more deuteriums until fully deuterated;

R' is selected from H, a $C_{1-6}$ alkyl, and a $C_{1-6}$ haloalkyl, and the group is optionally substituted with one or more deuteriums until fully deuterated;

R" is $-L_3$-B;

B is a 5- to 7-membered heterocyclyl, and is optionally substituted with t $R_5$ substituents;

$-L_3-$ is —$(CR_eR_f)_p$—, and, where valence allows, any methylene unit in —$(CR_eR_f)_p$— is optionally and independently replaced by —O—, —S—, and —C(O)—;

$R_{2a}$, $R_{2b}$, $R_{2c}$, $R_{2d}$, $R_{2e}$, $R_{3a}$, $R_{3b}$, $R_{3c}$, and $R_{3d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, $NR_{s1}R_{s2}$, —$C(O)R_{s1}$, —$C(O)OR_{s1}$, —$C(O)NR_{s1}R_{s2}$, —$SOR_{s1}$, and —$SO_2R_{s1}$, and the groups are optionally substituted with one or more deuteriums until fully deuterated;

each $R_5$ is independently selected from H, a $C_{1-6}$ alkyl, and a $C_{1-6}$ haloalkyl, and the group is optionally substituted with one or more deuteriums until fully deuterated;

$R_e$ and $R_f$ are independently selected from H, D, a $C_{1-6}$ alkyl, and a $C_{1-6}$ haloalkyl, and the groups are optionally substituted with one or more deuteriums until fully deuterated;

$R_{s1}$ and $R_{s2}$ are independently selected from H, a $C_{1-6}$ alkyl, or a $C_{1-6}$ haloalkyl, and the groups are optionally substituted with one or more deuteriums until fully deuterated;

p is 0, 1, 2, or 3; and t is 1, 2, or 3.

In one embodiment, the present invention relates to the compound represented by formula (IV) above, or the pharmaceutically acceptable salt, enantiomer, diastereomer, racemate, solvate, hydrate, polymorph, prodrug, or isotopic variant thereof, wherein:

X is $CR_x$;

Y is N;

$R_x$ is selected from H, D, a $C_{1-6}$ alkyl, and a $C_{1-6}$ haloalkyl, and the group is optionally substituted with one or more deuteriums until fully deuterated;

R' is selected from H, a $C_{1-6}$ alkyl, and a $C_{1-6}$ haloalkyl, and the group is optionally substituted with one or more deuteriums until fully deuterated;

R" is $-L_3$-B;

B is a 5- to 6-membered heterocyclyl, and is optionally substituted with t $R_5$ substituents;

$-L_3-$ is —$(CR_eR_f)_p$—;

$R_{2a}$, $R_{2b}$, $R_{2c}$, $R_{2d}$, $R_{2e}$, $R_{3a}$, $R_{3b}$, $R_{3c}$, and $R_{3d}$ are independently selected from H, D, a halogen, a $C_{1-6}$ alkyl, and a $C_{1-6}$ haloalkyl, and the groups are optionally substituted with one or more deuteriums until fully deuterated;

each $R_5$ is independently selected from H, D, a $C_{1-6}$ alkyl, and a $C_{1-6}$ haloalkyl, and the group is optionally substituted with one or more deuteriums until fully deuterated;

$R_e$ and $R_f$ are independently selected from H, D, a $C_{1-6}$ alkyl, and a $C_{1-6}$ haloalkyl, and the groups are optionally substituted with one or more deuteriums until fully deuterated;

p is 0, 1, 2, or 3;

t is 1, 2, or 3; and preferably, $-L_3$-B is selected from

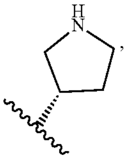,
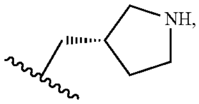
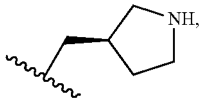

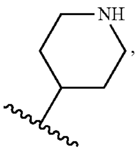
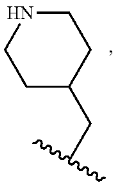,
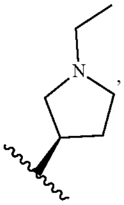,
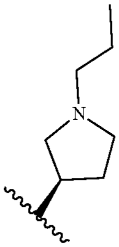,

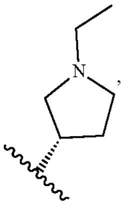,
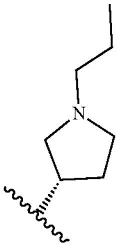, or
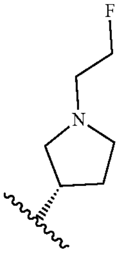.

In one embodiment, the present invention relates to the compound represented by formula (IV) above, or the pharmaceutically acceptable salt, enantiomer, diastereomer, racemate, solvate, hydrate, polymorph, prodrug, or isotopic variant thereof, wherein:

X is $CR_x$;

Y is N;

$R_x$ is H or D;

R' is H;

R" is $-L_3$-B;

B is a 5- to 6-membered heterocyclyl, preferably azacyclopentyl or azacyclohexyl;

$-L_3$- is $-(CR_eR_f)_p-$, and p is 0 or 1;

$R_{2a}$ is a $C_{1-6}$ alkyl, preferably methyl;

$R_{2b}$ is H or D;

$R_{2c}$ is a halogen, preferably F;

$R_{2d}$ is H or D;

$R_{2e}$ is H or D;

$R_{3a}$ is H or D;

$R_{3e}$ is a $C_{1-6}$ haloalkyl, preferably $-CF_3$;

$R_{3c}$ is a halogen, preferably Cl;

$R_{3d}$ is H or D;

$R_e$ is selected from H, D, and a $C_{1-6}$ alkyl;

$R_f$ is selected from H, D, and a $C_{1-6}$ alkyl; and preferably, $-L_3$-B is selected from

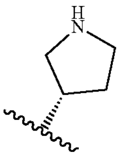,
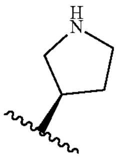,
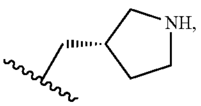

-continued

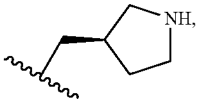
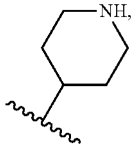 and
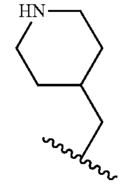.

In one embodiment, the present invention relates to the compound represented by general formula (I) above, or the pharmaceutically acceptable salt, enantiomer, diastereomer, racemate, solvate, hydrate, polymorph, prodrug, or isotopic variant thereof, which is formula (V), (V)

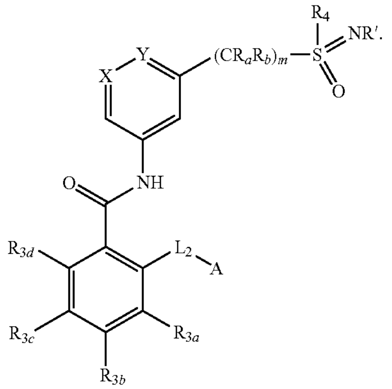

In one embodiment, the present invention relates to the compound represented by formula (V) above, or the pharmaceutically acceptable salt, enantiomer, diastereomer, racemate, solvate, hydrate, polymorph, prodrug, or isotopic variant thereof, wherein:

X is N or $CR_x$;

Y is N or $CR_y$;

$R_x$ and $R_y$ are each independently selected from H, D, a halogen, a $C_{1-6}$ alkyl, a $C_{2-6}$ alkenyl, a $C_{2-6}$ alkynyl, a $C_{1-6}$ haloalkyl, and $-OR_{s1}$, and the groups are optionally substituted with one or more deuteriums until fully deuterated;

$-L_2$- is a bond, —O—, —S—, or —NH—;

A is selected from phenyl, a $C_{3-8}$ cycloalkyl, a 5- to 6-membered heteroaryl, and a 5- to 10-membered heterocyclyl, and is optionally substituted with s $R_2$ substituents;

where valence allows, any methylene unit in $-(CR_aR_b)_m-$ is optionally and independently replaced by —O—, —S—, and —C(O)—;

R' is selected from H, a $C_{1-6}$ alkyl, and a $C_{1-6}$ haloalkyl, and the group is optionally substituted with one or more deuteriums until fully deuterated;

$R_2$, $R_{3a}$, $R_{3b}$, $R_{3c}$, and $R_{3d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, $-OR_{s1}$, $-SR_{s1}$, $NR_{s1}R_{s2}$, $-C(O)R_{s1}$, $-C(O)OR_{s1}$, $-C(O)NR_{s1}R_{s2}$, $-SOR_{s1}$, and $-SO_2R_{s1}$, and the groups are optionally substituted with one or more deuteriums until fully deuterated;

$R_4$ is selected from H, a $C_{1-6}$ alkyl, and a $C_{1-6}$ haloalkyl, and the group is optionally substituted with one or more deuteriums until fully deuterated;

$R_a$ and $R_b$ are selected from H, D, a halogen, a $C_{1-6}$ alkyl, or a $C_{1-6}$ haloalkyl, and the groups are optionally substituted with one or more deuteriums until fully deuterated;

or $R_a$ and $R_b$ together with the carbon atom to which they are attached form a $C_{3-6}$ cycloalkyl and a 3- to 5-membered heterocyclyl;

$R_{s1}$ and $R_{s2}$ are independently selected from H, a $C_{1-6}$ alkyl, or a $C_{1-6}$ haloalkyl, and the groups are optionally substituted with one or more deuteriums until fully deuterated;

m is 0, 1, 2, 3 or 4; and s is 1, 2, 3, 4, 5, 6, 7, or 8.

In one embodiment, the present invention relates to the compound represented by formula (IV) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ and $R_y$ are each independently selected from H, D, a halogen, and a $C_{1-6}$ alkyl, and the groups are optionally substituted with one or more deuteriums until fully deuterated;

A is selected from

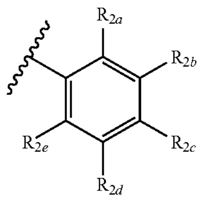

and a 5- to 8-membered heterocyclyl, and is optionally substituted with s $R_2$ substituents;

where valence allows, any methylene unit in —$(CR_aR_b)_m$— is optionally and independently replaced by —O—;

-$L_2$- is a bond or —O—;

R' is selected from H, a $C_{1-6}$ alkyl, and a $C_{1-6}$ haloalkyl, and the group is optionally substituted with one or more deuteriums until fully deuterated;

each $R_2$ is independently selected from H, D, a halogen, a $C_{1-6}$ alkyl, a $C_{1-6}$ haloalkyl, and —$OR_{s1}$, and the group is optionally substituted with one or more deuteriums until fully deuterated;

$R_{2a}$ is selected from H, D, a halogen, a $C_{1-6}$ alkyl, a $C_{1-6}$ haloalkyl, —$OR_{s1a}$, and —$SR_{s1a}$, and the group is optionally substituted with one or more deuteriums until fully deuterated;

$R_{2b}$ is H or D;

$R_{2c}$ is H, D, a halogen, —$OR_{s1c}$, or —$SR_{s1c}$;

$R_{2d}$ is H or D;

$R_{2e}$ is H or D;

$R_{3a}$ is H or D;

$R_{3b}$ is a $C_{1-6}$ haloalkyl, and the group is optionally substituted with one or more deuteriums until fully deuterated;

$R_{3c}$ is a halogen;

$R_{3d}$ is H or D;

$R_4$ is selected from a $C_{1-6}$ alkyl and a $C_{1-6}$ haloalkyl, and the group is optionally substituted with one or more deuteriums until fully deuterated;

$R_a$ and $R_b$ are selected from H, D, a halogen, and a $C_{1-6}$ alkyl, and the groups are optionally substituted with one or more deuteriums until fully deuterated;

or $R_a$ and $R_b$ together with the carbon atom to which they are attached form a $C_{3-6}$ cycloalkyl;

each $R_{s1}$ is independently selected from H, a $C_{1-6}$ alkyl, or a $C_{1-6}$ haloalkyl, and the group is optionally substituted with one or more deuteriums until fully deuterated;

$R_{s1a}$ is selected from H, a $C_{1-6}$ alkyl, or a $C_{1-6}$ haloalkyl, and the group is optionally substituted with one or more deuteriums until fully deuterated;

$R_{s1c}$ is selected from H, a $C_{1-6}$ alkyl, or a $C_{1-6}$ haloalkyl, and the group is optionally substituted with one or more deuteriums until fully deuterated;

m is 1, 2 or 3; and s is 1 or 2.

In one embodiment, the present invention relates to the compound represented by formula (IV) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ is H;

$R_y$ is a halogen;

A is selected from

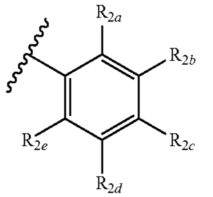

and azepanyl, and is substituted with s $R_2$;

—$(CR_aR_b)_m$— is selected from —$CH_2$—, —O—$CH_2$—$CH_2$—,

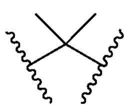
, and
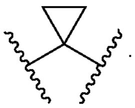
.

-$L_2$- is a bond or —O—;

R' is H;

each $R_2$ is independently selected from H and a halogen, preferably F, and the group is optionally substituted with one or more deuteriums until fully deuterated;

$R_{2a}$ is H or a $C_{1-6}$ alkyl, preferably methyl, and the group is optionally substituted with one or more deuteriums until fully deuterated;

$R_{2b}$ is H;

$R_{2c}$ is a halogen or —$OR_{s1c}$;

$R_{2d}$ is H;

$R_{2e}$ is H;

$R_{3a}$ is H;

$R_{3e}$ is a $C_{1-6}$ haloalkyl, preferably —$CF_3$;

$R_{3c}$ is a halogen, preferably Cl;

$R_{3d}$ is H;

$R_4$ is a $C_{1-6}$ alkyl, preferably methyl;

$R_{s1c}$ is H, a $C_{1-6}$ alkyl, or a $C_{1-6}$ haloalkyl, preferably —$CF_3$; and s is 1 or 2.

In one embodiment, the present invention relates to the compound represented by formula (I) above, or the pharmaceutically acceptable salt, enantiomer, diastereomer, racemate, solvate, hydrate, polymorph, prodrug, or isotopic variant thereof, which is formula (VI):

(VI)

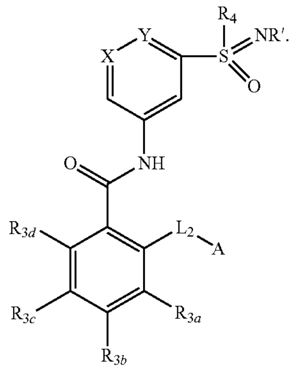

In one embodiment, the present invention relates to the compound represented by formula (VI) above, or the pharmaceutically acceptable salt, enantiomer, diastereomer, racemate, solvate, hydrate, polymorph, prodrug, or isotopic variant thereof, wherein:

X is N or $CR_x$;

Y is N or $CR_y$;

$R_x$ and $R_y$ are each independently selected from H, D, a halogen, a $C_{1-6}$ alkyl, a $C_{2-6}$ alkenyl, a $C_{2-6}$ alkynyl, a $C_{1-6}$ haloalkyl, and —$OR_{s1}$, and the groups are optionally substituted with one or more deuteriums until fully deuterated;

-$L_2$- is a bond, —O—, —S—, or —NH—;

A is selected from phenyl, a $C_{3-8}$ cycloalkyl, a 5- to 10-membered heteroaryl, and a 5- to 10-membered heterocyclyl, and is optionally substituted with s $R_2$ substituents;

R' is selected from H, a $C_{1-6}$ alkyl, and a $C_{1-6}$ haloalkyl, and the group is optionally substituted with one or more deuteriums until fully deuterated;

$R_2$, $R_{3a}$, $R_{3b}$, $R_{3c}$, and $R_{3d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, $OR_{s1}$, $SR_{s1}$, $NR_{s1}R_{s2}$, —$C(O)R_{s1}$, —$C(O)OR_{s1}$, —$C(O)NR_{s1}R_{s2}$, —$SOR_{s1}$, and —$SO_2R_{s1}$, and the groups are optionally substituted with one or more deuteriums until fully deuterated;

$R_4$ is selected from H, a $C_{1-6}$ alkyl, and a $C_{1-6}$ haloalkyl, and the group is optionally substituted with one or more deuteriums until fully deuterated;

$R_{s1}$ and $R_{s2}$ are independently selected from H, a $C_{1-6}$ alkyl, or a $C_{1-6}$ haloalkyl, and the groups are optionally substituted with one or more deuteriums until fully deuterated; and s is 1, 2, 3, 4, 5, 6, 7, or 8.

In one embodiment, the present invention relates to the compound represented by formula (VI) above, or the pharmaceutically acceptable salt, enantiomer, diastereomer, racemate, solvate, hydrate, polymorph, prodrug, or isotopic variant thereof, wherein:

A is selected from cyclopentyl, cyclohexyl, azacyclohexyl, oxacyclohexyl, thiacyclohexyl, azepanyl, diazepanyl, octahydrocyclopentadienopyrrole, octahydropyrrolopyrrolyl, octahydrocyclopentadienyl, phenyl, pyrrolyl, furanyl, thienyl, pyridyl, pyrimidinyl and pyridazinyl, and preferably, A and substituents thereon are selected from:

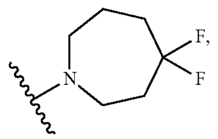

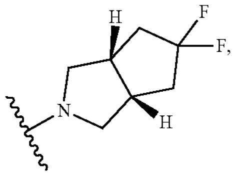

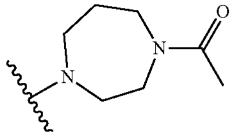

,

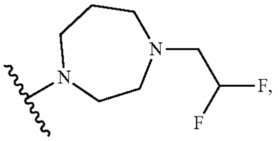

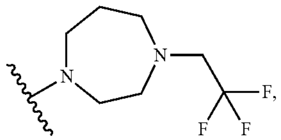

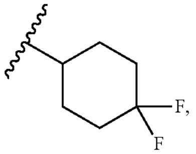

and

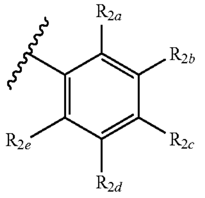

wherein $R_{2a}$, $R_{2b}$, $R_{2c}$, and $R_{2d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, $NR_{s1}R_{s2}$, —$C(O)R_{s1}$, —$C(O)OR_{s1}$, —$C(O)NR_{s1}R_{s2}$, —$SOR_{s1}$, and —$SO_2R_{s1}$, and the groups are optionally substituted with one or more deuteriums until fully deuterated.

In one embodiment, the present invention relates to the compound represented by formula (VI) above, or the pharmaceutically acceptable salt, enantiomer, diastereomer, racemate, solvate, hydrate, polymorph, prodrug, or isotopic variant thereof, wherein:

-$L_2$- is —O—; and

A is selected from cyclopentyl and cyclohexyl, preferably cyclohexyl.

In one embodiment, the present invention relates to the compound represented by formula (VI) above, or the pharmaceutically acceptable salt, enantiomer, diastereomer, racemate, solvate, hydrate, polymorph, prodrug, or isotopic variant thereof, wherein:

-$L_2$- is a bond; and

A is selected from azepanyl, diazepanyl, octahydrocyclopentadienopyrrole, octahydropyrrolopyrrolyl, and octahydrocyclopentadienyl, and preferably, in the case that A is a nitrogen-containing heterocycle, A is connected to the phenyl via a nitrogen atom.

In one embodiment, the present invention relates to the compound represented by formula (I) above, or the pharmaceutically acceptable salt, enantiomer, diastereomer, racemate, solvate, hydrate, polymorph, prodrug, or isotopic variant thereof, which is formula (VII), (VII)

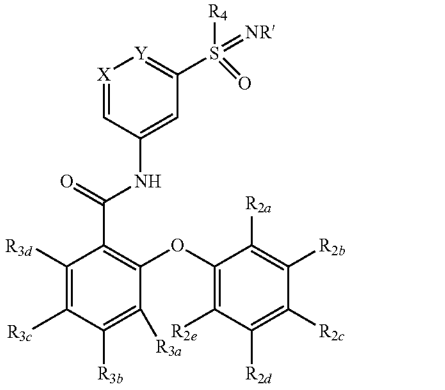

wherein:

X is N or $CR_x$;

Y is N or $CR_y$;

$R_x$ and $R_y$ are each independently selected from H, D, a halogen, a $C_{1-6}$ alkyl, a $C_{2-6}$ alkenyl, a $C_{2-6}$ alkynyl, or a $C_{1-6}$ haloalkyl, and the groups are optionally substituted with one or more deuteriums until fully deuterated;

R' is selected from H, a $C_{1-6}$ alkyl, and a $C_{1-6}$ haloalkyl, and the group is optionally substituted with one or more deuteriums until fully deuterated;

$R_{2a}$, $R_{2b}$, $R_{2c}$, $R_{2d}$, $R_{2e}$, $R_{3a}$, $R_{3b}$, $R_{3c}$, and $R_{3d}$ are independently selected from H, D, a halogen, CN, a $C_{1-6}$ alkyl, a $C_{2-6}$ alkenyl, a $C_{2-6}$ alkynyl, a $C_{1-6}$ haloalkyl, —$OR_{s1}$, —$SR_{s1}$, $NR_{s1}R_{s2}$, —C(O)$R_{s1}$, —C(O)$OR_{s1}$, —C(O)$NR_{s1}R_{s2}$, —$SOR_{s1}$, and —$SO_2R_{s1}$, and the groups are optionally substituted with one or more deuteriums until fully deuterated;

$R_4$ is selected from H, a $C_{1-6}$ alkyl, and a $C_{1-6}$ haloalkyl, and the group is optionally substituted with one or more deuteriums until fully deuterated; and $R_{s1}$ and $R_{s2}$ are independently selected from H, a $C_{1-6}$ alkyl, or a $C_{1-6}$ haloalkyl, and the groups are optionally substituted with one or more deuteriums until fully deuterated.

In one embodiment, the present invention relates to the compound represented by formula (VII) above, or the pharmaceutically acceptable salt, enantiomer, diastereomer, racemate, solvate, hydrate, polymorph, prodrug, or isotopic variant thereof, wherein:

X is N or $CR_x$;

Y is N or $CR_y$;

$R_x$ and $R_y$ are each independently selected from H, D, a halogen, a $C_{1-6}$ alkyl, or a $C_{1-6}$ haloalkyl, and the groups are optionally substituted with one or more deuteriums until fully deuterated;

R' is selected from H, a $C_{1-6}$ alkyl, and a $C_{1-6}$ haloalkyl, and the group is optionally substituted with one or more deuteriums until fully deuterated;

$R_{2a}$ is selected from H, D, a halogen, —$OR_{s1a}$, —$SR_{s1a}$, $NR_{s1a}R_{s2a}$, a $C_{1-6}$ alkyl, and a $C_{1-6}$ haloalkyl, and the group is optionally substituted with one or more deuteriums until fully deuterated;

$R_{2b}$ is H, D, a halogen, a $C_{1-6}$ alkyl, or a $C_{1-6}$ haloalkyl, and the group is optionally substituted with one or more deuteriums until fully deuterated;

$R_{2c}$ is selected from H, D, a halogen, —$OR_{s1c}$, —$SR_{s1c}$, $NR_{s1c}R_{s2c}$, a $C_{1-6}$ alkyl, and a $C_{1-6}$ haloalkyl, and the group is optionally substituted with one or more deuteriums until fully deuterated;

$R_{2d}$ is H, D, a halogen, a $C_{1-6}$ alkyl, and a $C_{1-6}$ haloalkyl, and the group is optionally substituted with one or more deuteriums until fully deuterated;

$R_{2e}$ is H, D, a halogen, a $C_{1-6}$ alkyl, and a $C_{1-6}$ haloalkyl, and the group is optionally substituted with one or more deuteriums until fully deuterated;

$R_{3a}$ is H, D, a halogen, a $C_{1-6}$ alkyl, and a $C_{1-6}$ haloalkyl, and the group is optionally substituted with one or more deuteriums until fully deuterated;

$R_{3b}$ is selected from H, D, a halogen, a $C_{1-6}$ alkyl, and a $C_{1-6}$ haloalkyl, and the group is optionally substituted with one or more deuteriums until fully deuterated;

$R_{3c}$ is selected from H, D, a halogen, a $C_{1-6}$ alkyl, and a $C_{1-6}$ haloalkyl, and the group is optionally substituted with one or more deuteriums until fully deuterated;

$R_{3d}$ is H, D, a halogen, a $C_{1-6}$ alkyl, and a $C_{1-6}$ haloalkyl, and the group is optionally substituted with one or more deuteriums until fully deuterated;

$R_4$ is selected from H, a $C_{1-6}$ alkyl, and a $C_{1-6}$ haloalkyl, and the group is optionally substituted with one or more deuteriums until fully deuterated; and $R_{s1a}$, $R_{s2a}$, $R_{s1c}$, and $R_{s2c}$ are each independently selected from H, a $C_{1-6}$ alkyl, or a $C_{1-6}$ haloalkyl, and the groups are optionally substituted with one or more deuteriums until fully deuterated.

In one embodiment, the present invention relates to the compound represented by formula (VII) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ and $R_y$ are independently selected from H, D, a halogen, a $C_{1-6}$ alkyl, or a $C_{1-6}$ haloalkyl, and the groups are optionally substituted with one or more deuteriums until fully deuterated;

R' is H, a $C_{1-6}$ alkyl, or a $C_{1-6}$ haloalkyl, and the group is optionally substituted with one or more deuteriums until fully deuterated;

$R_{2a}$ is —$OR_{s1a}$, —$SR_{s1a}$, $NR_{s1a}R_{s2}$a, a $C_{1-6}$ alkyl, or a $C_{1-6}$ haloalkyl, and the group is optionally substituted with one or more deuteriums until fully deuterated;

$R_{2b}$ is H, D, or a halogen;

$R_{2c}$ is H, D, a halogen, —$OR_{s1c}$, —$SR_{s1c}$, or $NR_{s1c}R_{s2c}$, and the group is optionally substituted with one or more deuteriums until fully deuterated;

$R_{2d}$ is H, D, or a halogen;

$R_{2e}$ is H, D, or a halogen;

$R_{3a}$ is H, D, or a halogen;

$R_{3e}$ is H, D, a halogen, a $C_{1-6}$ alkyl, or a $C_{1-6}$ haloalkyl, and the group is optionally substituted with one or more deuteriums until fully deuterated;

$R_{3c}$ is H, D, or a halogen;

$R_{3d}$ is H, D, or a halogen;

$R_4$ is H, a $C_{1-6}$ alkyl, or a $C_{1-6}$ haloalkyl, and the group is optionally substituted with one or more deuteriums until fully deuterated; and $R_{s1a}$, $R_{s2a}$, $R_{s1c}$, and $R_{s2c}$ are each independently selected from H, a $C_{1-6}$ alkyl, or a $C_{1-6}$ haloalkyl, and the groups are optionally substituted with one or more deuteriums until fully deuterated;

with the proviso that when Y is N, $R_{2a}$ is not a $C_{1-6}$ alkyl or a $C_{1-6}$ haloalkyl.

In one embodiment, the present invention relates to the compound represented by formula (VII) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ and $R_y$ are independently selected from H, D, or a halogen;

R' is H, a $C_{1-6}$ alkyl, or a $C_{1-6}$ haloalkyl; $R_{2a}$ is —$OR_{s1a}$, —$SR_{s1a}$, a $C_{1-6}$ alkyl, or a $C_{1-6}$ haloalkyl, and the group is optionally substituted with one or more deuteriums until fully deuterated;

$R_{2b}$ is H, D, or a halogen;

$R_{2c}$ is H, D, a halogen, —$OR_{s1c}$, or —$SR_{s1c}$, and the group is optionally substituted with one or more deuteriums until fully deuterated;

$R_{2d}$ is H or D;

$R_{2e}$ is H or D;

$R_{3a}$ is H or D;

$R_{3e}$ is a $C_{1-6}$ haloalkyl;

$R_{3c}$ is a halogen;

$R_{3d}$ is H or D;

$R_4$ is a $C_{1-6}$ alkyl or a $C_{1-6}$ haloalkyl; and $R_{s1a}$ and $R_{s1c}$ are independently selected from a $C_{1-6}$ alkyl or a $C_{1-6}$ haloalkyl; with the proviso that when Y is N, $R_{2a}$ is not a $C_{1-6}$ alkyl or a $C_{1-6}$ haloalkyl.

In one embodiment, the present invention relates to the compound represented by formula (VII) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ and $R_y$ are independently selected from H, D, or a halogen;

R' is H;

$R_{2a}$ is —$OR_{s1a}$, —$SR_{s1a}$, or a $C_{1-6}$ alkyl, and the group is optionally substituted with one or more deuteriums until fully deuterated;

$R_{2b}$ is H or D;

$R_{2c}$ is a halogen, —$OR_{s1c}$, or —$SR_{s1c}$, and the group is optionally substituted with one or more deuteriums until fully deuterated;

$R_{2d}$ is H or D;

$R_{2e}$ is H or D;

$R_{3a}$ is H or D;

$R_{3b}$ is a $C_{1-6}$ alkyl or a $C_{1-6}$ haloalkyl, and the group is optionally substituted with one or more deuteriums until fully deuterated;

$R_{3c}$ is a halogen;

$R_{3d}$ is H or D;

$R_4$ is a $C_{1-6}$ alkyl or a $C_{1-6}$ haloalkyl, and the group is optionally substituted with one or more deuteriums until fully deuterated; and $R_{s1a}$ and $R_{s1c}$ are each independently selected from H, a $C_{1-6}$ alkyl, or a $C_{1-6}$ haloalkyl, and the groups are optionally substituted with one or more deuteriums until fully deuterated.

In one embodiment, the present invention relates to the compound represented by formula (VII) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ is H or D;

$R_y$ is H, D, or a halogen;

R' is H;

$R_{2a}$ is —$OR_{s1a}$ or —$SR_{s1a}$, and the group is optionally substituted with one or more deuteriums until fully deuterated;

$R_{2b}$ is H or D;

$R_{2c}$ is a halogen, —$OR_{s1c}$, or —$SR_{s1c}$;

$R_{2d}$ is H or D;

$R_{2e}$ is H or D;

$R_{3a}$ is H or D;

$R_{3b}$ is a $C_{1-6}$ alkyl or a $C_{1-6}$ haloalkyl, and the group is optionally substituted with one or more deuteriums until fully deuterated;

$R_{3c}$ is a halogen;

$R_{3d}$ is H or D;

$R_4$ is a $C_{1-6}$ alkyl or a $C_{1-6}$ haloalkyl, and the group is optionally substituted with one or more deuteriums until fully deuterated; and $R_{s1a}$ and $R_{s1c}$ are independently selected from a $C_{1-6}$ alkyl or a $C_{1-6}$ haloalkyl, and the groups are optionally substituted with one or more deuteriums until fully deuterated.

In one embodiment, the present invention relates to the compound represented by formula (VII) above, or the pharmaceutically acceptable salt, enantiomer, diastereomer, racemate, solvate, hydrate, polymorph, prodrug, or isotopic variant thereof, wherein:

X is $CR_x$;

Y is N or $CR_y$;

$R_x$ is H;

$R_y$ is a halogen, preferably F;

R' is H;

$R_{2a}$ is —$OR_{s1a}$, and the group is optionally substituted with one or more deuteriums until fully deuterated, preferably —$OCD_3$;

$R_{2b}$ is H;

$R_{2c}$ is a halogen or —$OR_{s1c}$, preferably F or —$OCF_3$;

$R_{2d}$ is H;

$R_{2e}$ is H;

$R_{3a}$ is H;

$R_{3b}$ is a $C_{1-6}$ haloalkyl, preferably —$CF_3$;

$R_{3c}$ is a halogen, preferably Cl;

$R_{3d}$ is H;

$R_4$ is a $C_{1-6}$ alkyl;

$R_{s1a}$ is a $C_{1-6}$ alkyl; and $R_{s1c}$ is a $C_{1-6}$ haloalkyl.

In one specific embodiment, the compound is selected from the following structures:

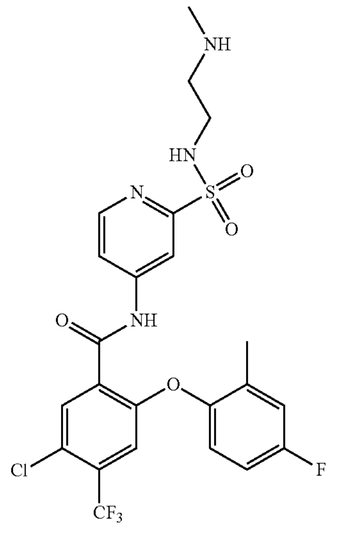

-continued
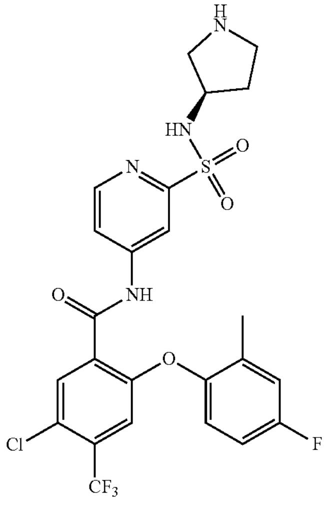
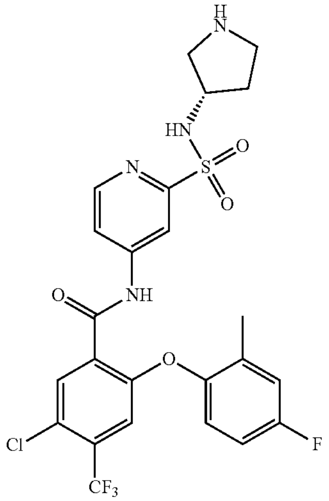
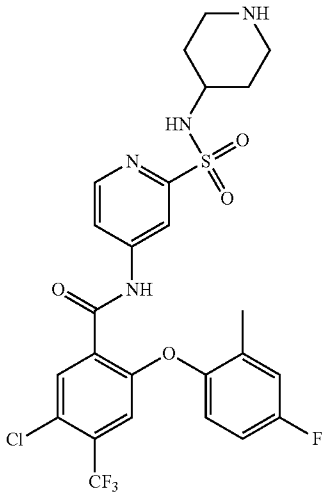
-continued
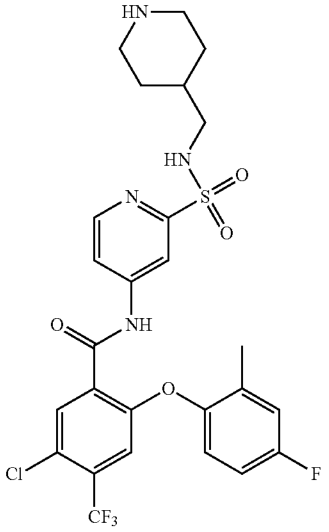
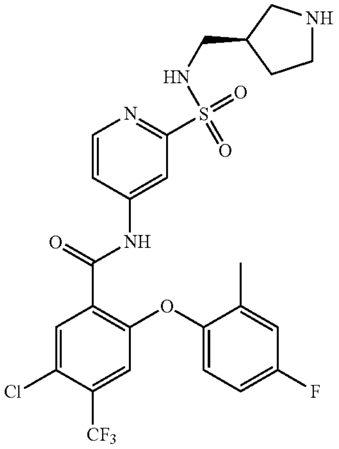
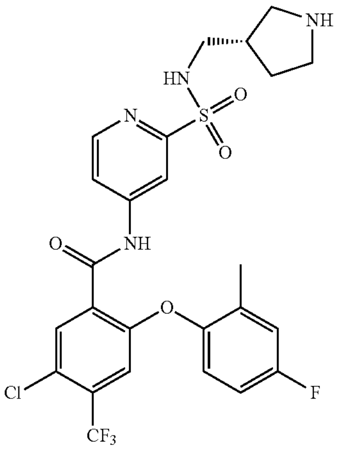

-continued
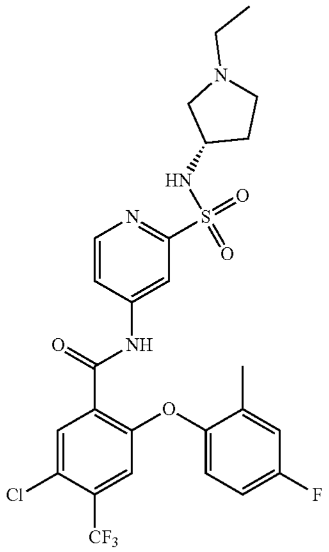
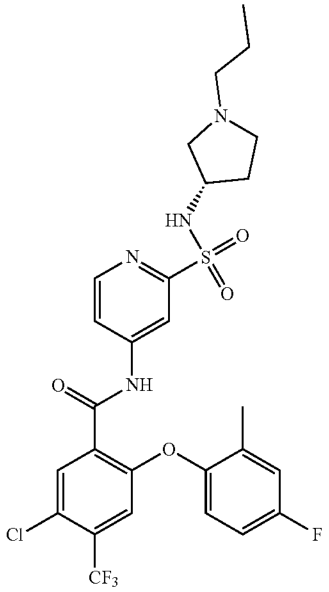
-continued
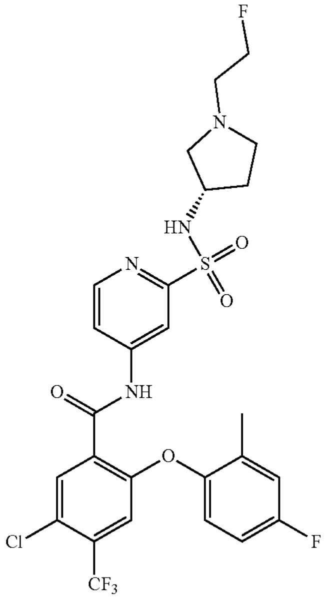
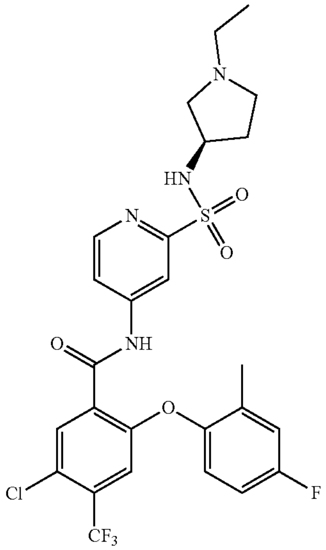

-continued
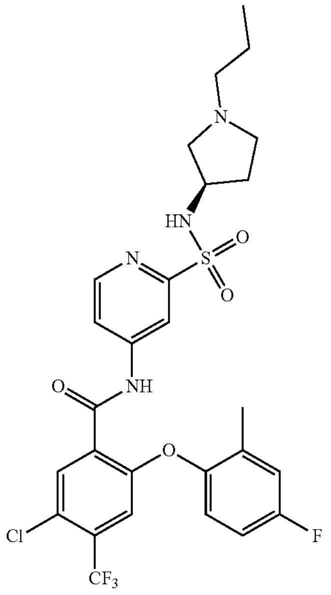
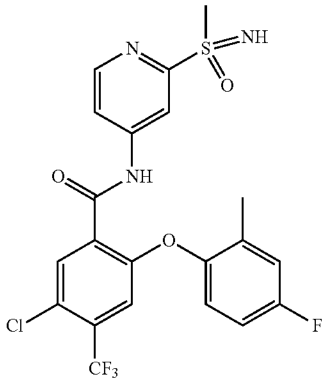
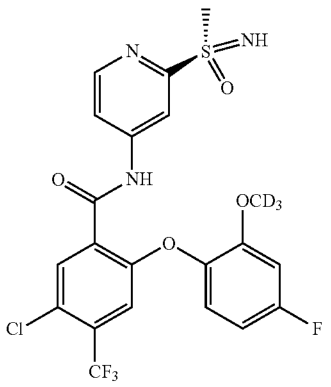
-continued
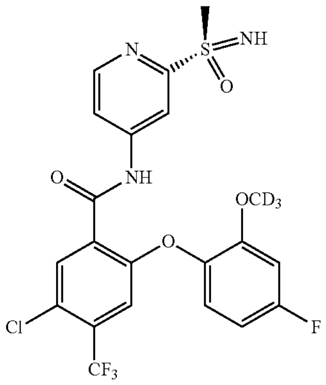
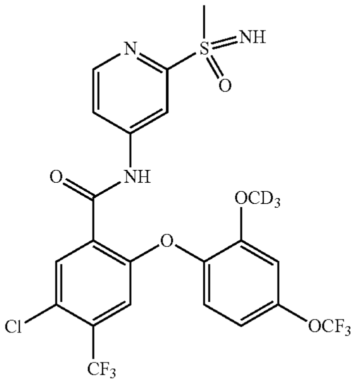
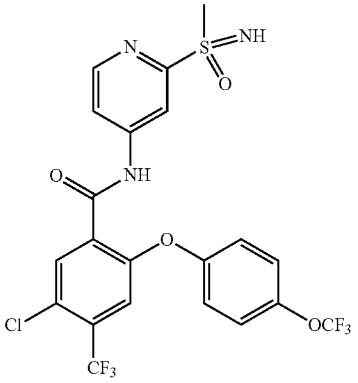
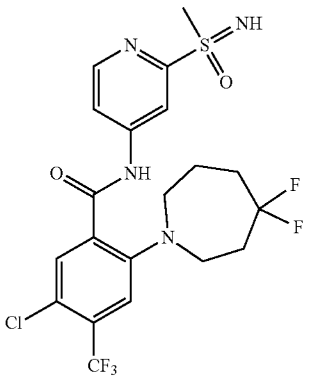

-continued
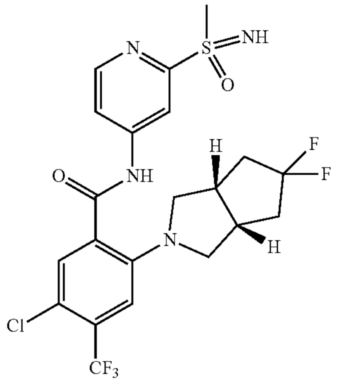
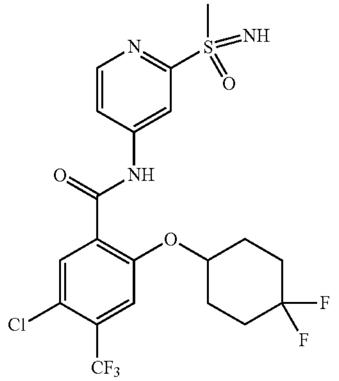
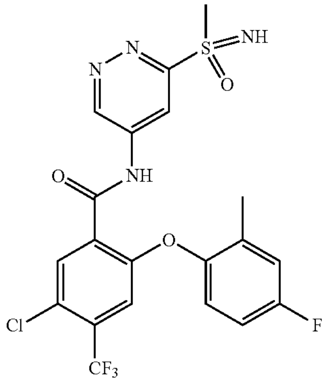
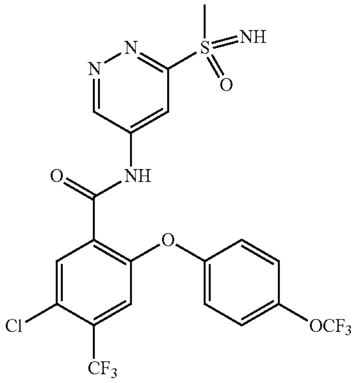
-continued
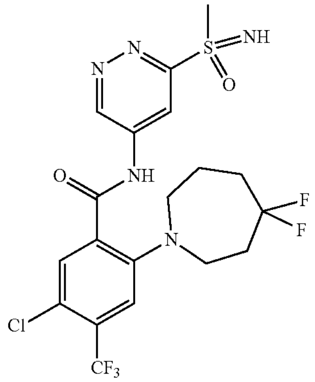
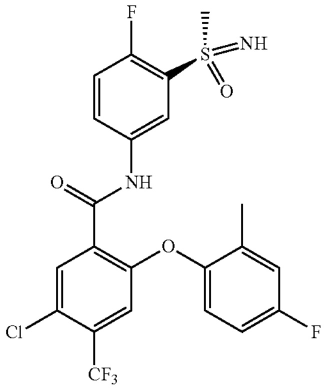
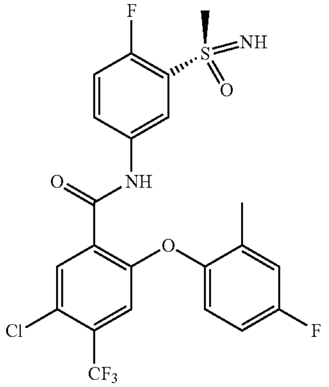
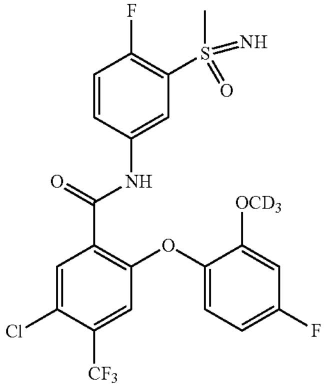

-continued
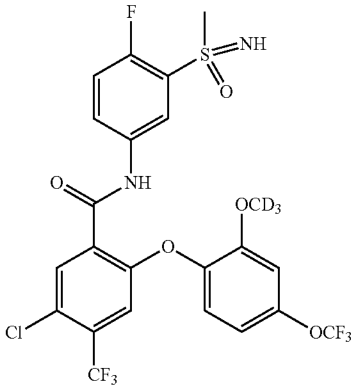
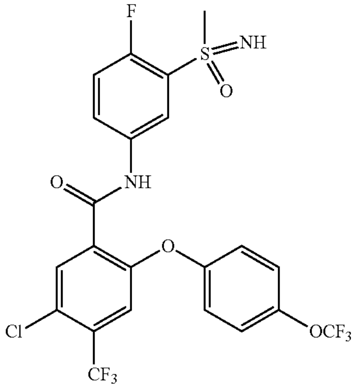
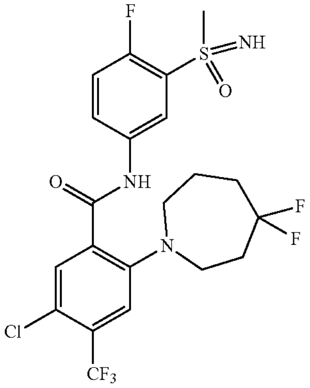
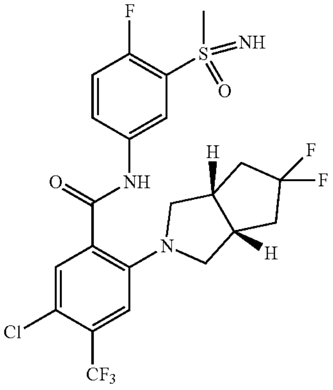
-continued
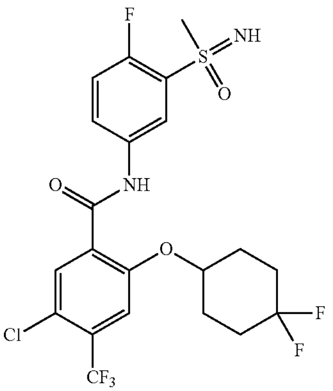
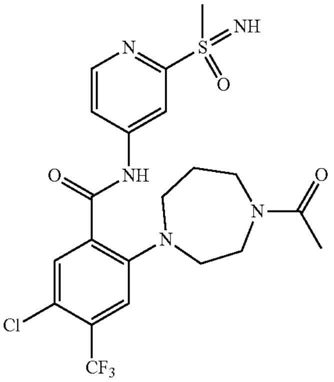
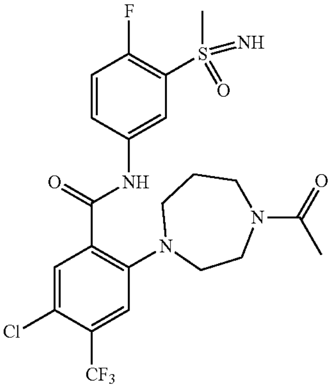
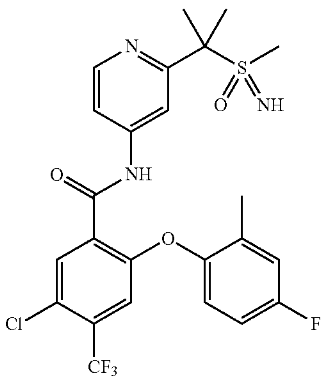

-continued
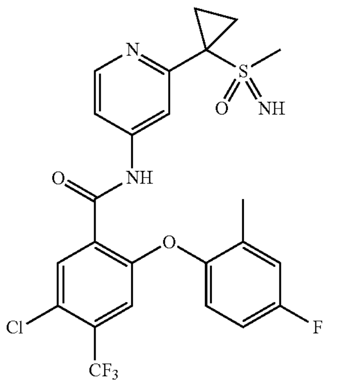
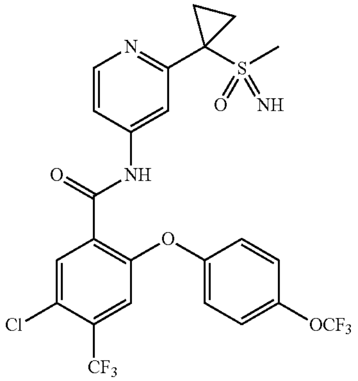
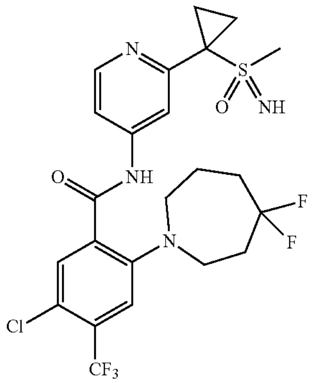
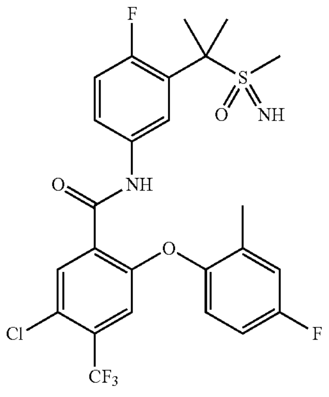
-continued
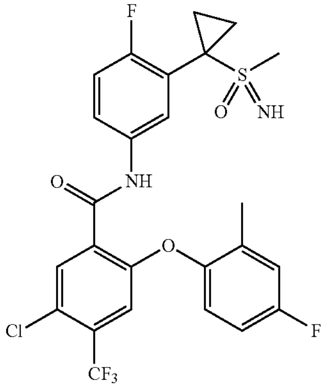
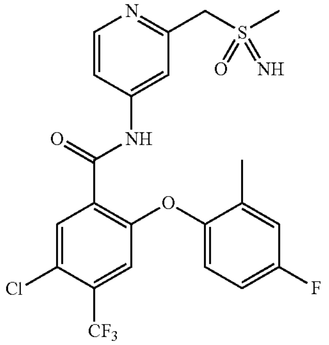
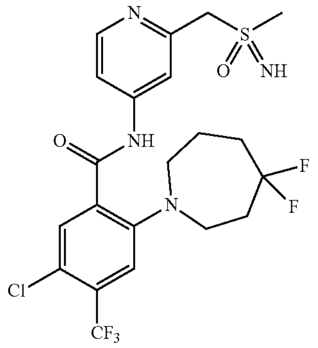
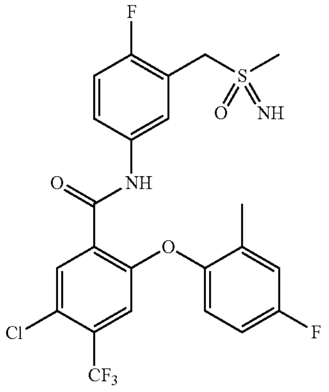

-continued
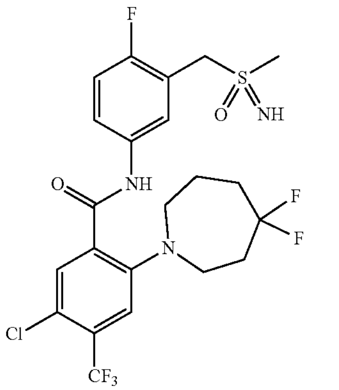
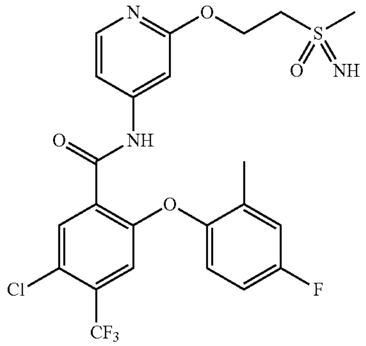
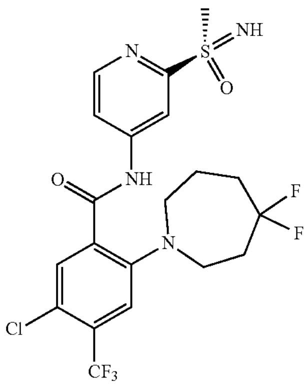
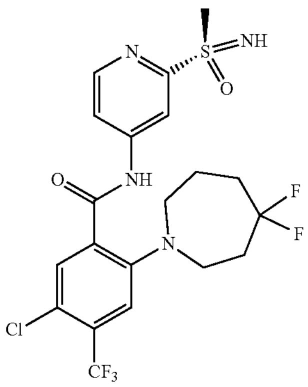
-continued
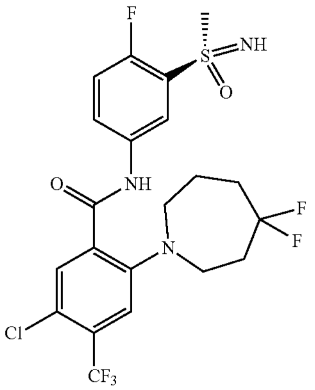
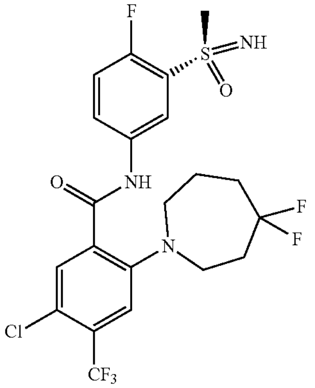
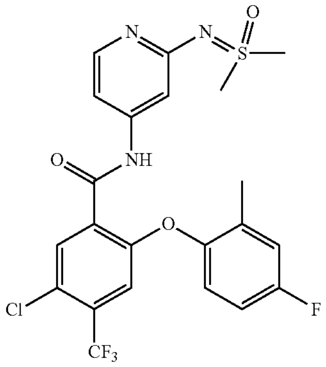
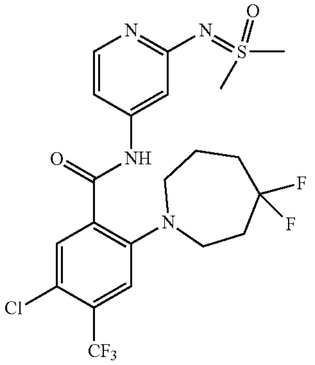

-continued

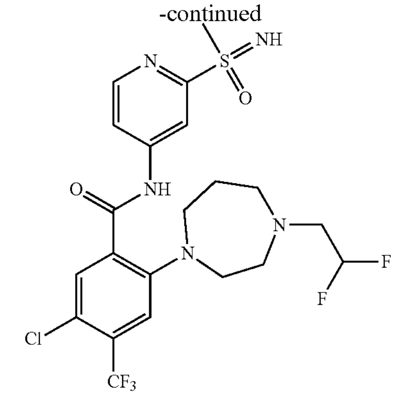

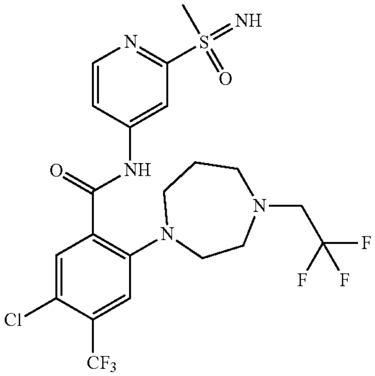

and

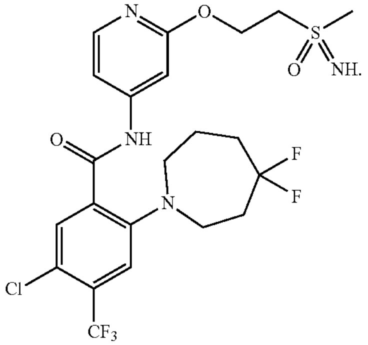

In one specific embodiment, the present invention relates to a pharmaceutical composition comprising the compound as defined herein or the pharmaceutically acceptable salt, enantiomer, diastereomer, racemate, solvate, hydrate, polymorph, prodrug, or isotopic variant thereof, and a mixture thereof, and a pharmaceutically acceptable excipient. Preferably, the pharmaceutical composition further comprises other therapeutic agents.

In one embodiment, the present invention provides a pharmaceutical composition comprising the compound as defined herein or the pharmaceutically acceptable salt, enantiomer, diastereomer, racemate, solvate, hydrate, polymorph, prodrug, or isotopic variant thereof, and a mixture thereof, and a pharmaceutically acceptable excipient. Preferably, the pharmaceutical composition further comprises other therapeutic agents.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same in the preparation of a medicament as a voltage-gated sodium channel inhibitor.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same in the preparation of a medicament as a sodium ion channel 1.8 (Nav1.8) inhibitor.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same as a voltage-gated sodium channel inhibitor.

In one embodiment, the present invention provides a use of the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same as a sodium ion channel 1.8 (Nav1.8) inhibitor.

In one embodiment, the present invention provides a method for inhibiting a voltage-gated sodium channel in a subject, comprising administering to the subject the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same.

In one embodiment, the present invention provides a method for inhibiting sodium ion channel 1.8 (Nav1.8) in a subject, comprising administering to the subject the compound as defined herein or the pharmaceutically acceptable salt, enantiomer, diastereomer, racemate, solvate, hydrate, polymorph, prodrug, or isotopic variant thereof, and a mixture thereof, or a pharmaceutical composition comprising the same.

The voltage-gated sodium channel inhibitor according to the present invention is useful in the treatment of a disease selected from: acute, chronic, neuropathic, or inflammatory pain, arthritis, migraine, cluster headache, trigeminal neuralgia, herpetic neuralgia, generalized neuralgia, epilepsy or epilepsy conditions, neurodegenerative diseases, psychiatric disorders such as anxiety and depression, bipolar disorder, muscular rigidity, arrhythmia, movement disorders, neuroendocrine disorders, ataxia, multiple sclerosis, irritable bowel syndrome, incontinence, visceral pain, osteoarthritic pain, postherpetic neuralgia, diabetic neuropathy, radiculalgia, sciatica, back pain, headache, neck pain, severe or intractable pain, nociceptive pain, penetrating pain, postoperative pain, cancer pain, stroke, cerebral ischemia, traumatic brain injury, amyotrophic lateral sclerosis, stress- or exercise-induced angina, heart palpitation, hypertension, migraine, or abnormal gastrointestinal activity.

In some embodiments, the disease relating to the present method is selected from radiculalgia, sciatica, back pain, headache, neck pain, intractable pain, acute pain, postoperative pain, back pain, tinnitus, or cancer pain.

EXAMPLES

The materials or reagents used herein were either commercially available or were prepared by synthetic methods generally known in the art.

Example 1
5-chloro-2-(4-fluoro-2-methylphenoxy)-N-(2-(N-(2-(methylamino)ethyl)sulfamoyl)pyridin-4-yl)-4-(trifluoromethyl)benzamide (Compound 1)
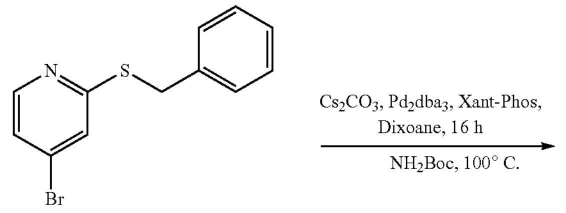
1A
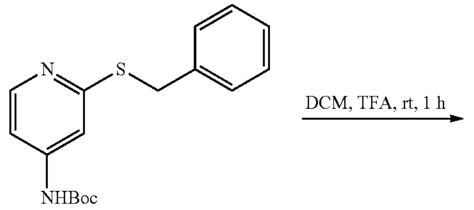
1B
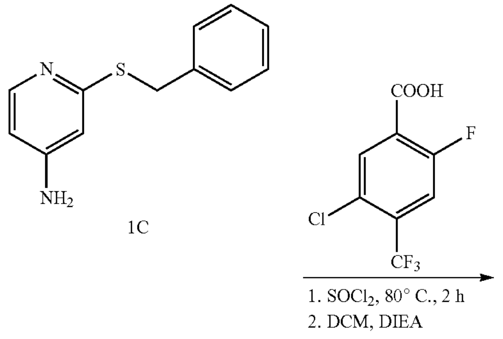
1C
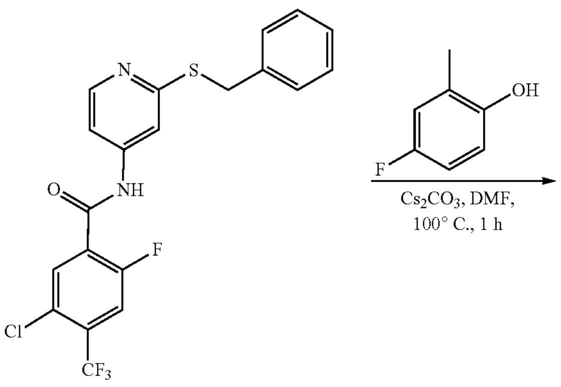
1D
-continued
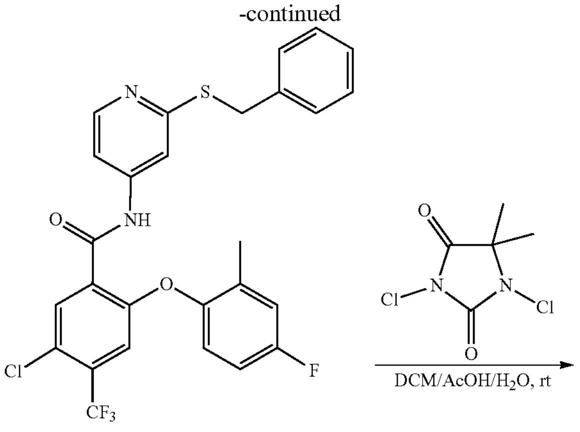
1E
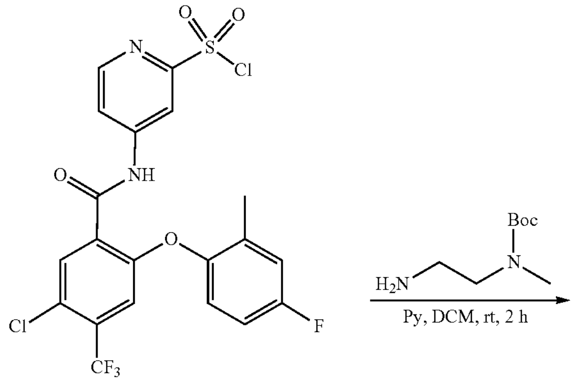
1F
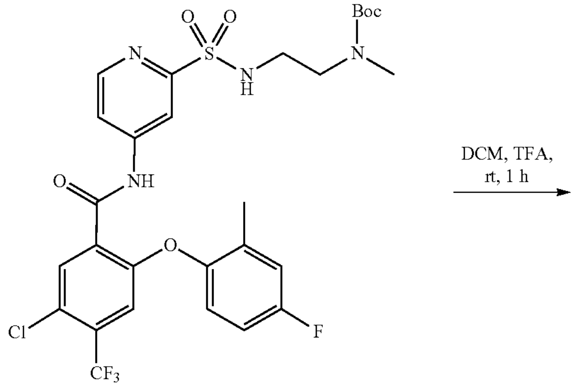
1G
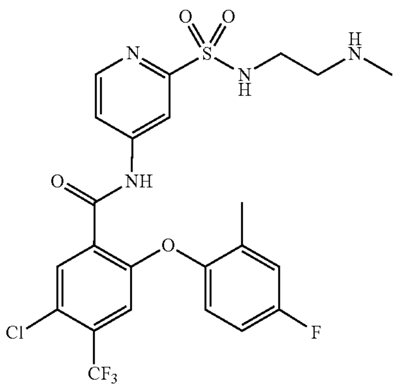
Compound 1

Step 1: Tert-butyl (2-(benzylthio)pyridin-4-yl)carbamate

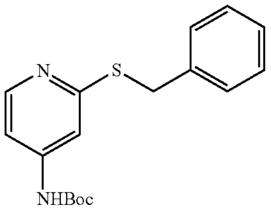 [SMILES: CC(C)(C)OC(=O)Nc1ccnc(SCc2ccccc2)c1]

2-(benzylthio)-4-bromopyridine (3.7 g, 13.214 mmol) was dissolved in ultra-dry dioxane (37 mL), and tert-butyl carbamate (3.1 g, 26.429 mmol), cesium carbonate (12.9 g, 39.643 mmol), tris(dibenzylideneacetone)dipalladium (Pd2dba3) (1.2 g, 1.321 mmol) and (9,9-dimethyl-9H-xanthene-4,5-diyl)bis(diphenylphosphine) (XantPhos) (1.5 g, 2.643 mmol) were added. Nitrogen replacement was performed, and the mixture was stirred in an oil bath at 100° C. for 16 hours. The reaction was stopped, and the reaction solution was spun dry in vacuo. The residue was dissolved in dichloroethane (40 ml), the resulting solution was subjected to suction filtration through a fritted funnel filled with diatomaceous earth, and the filter cake was rinsed using dichloroethane (80 ml). The filtrate was collected, spun dry, and adsorbed to silica gel to obtain a crude product. The crude product was separated and purified by silica gel column chromatography (mobile phase: petroleum ether: ethyl acetate=10:1) to obtain the title compound (3.7 g, yield: 77.6%, colorless oily matter).

MS (ESI): m/z 317.2 $[M+H]^+$;

Step 2: 2-(benzylthio)pyridin-4-amine

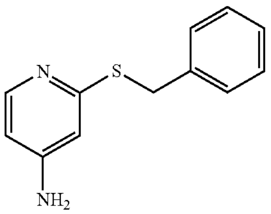 [SMILES: Nc1ccnc(SCc2ccccc2)c1]

Tert-butyl (2-(benzylthio)pyridin-4-yl)carbamate (1 g, 3.16 mmol) was dissolved in a dichloromethane solution (15 mL). Trifluoroacetic acid (5 mL) was added dropwise in an ice bath at 0° C., and the mixture was stirred at room temperature for 1 hour. The reaction was stopped, and the reaction solution was quenched by adding a saturated sodium bicarbonate solution (10 ml). The aqueous phase was extracted using ethyl acetate (15 ml×3). The organic phases were combined, washed with a saturated saline solution (10 ml×2), dried over anhydrous sodium sulfate, and filtered. The filtrate was spun dry in vacuo to obtain the title compound (680 mg, colorless oily matter), which was directly used in the next reaction.

MS (ESI): m/z 217.1 $[M+H]^+$;

Step 3: N-(2-(benzylthio)pyridin-4-yl)-5-chloro-2-fluoro-4-(trifluoromethyl)benzamide

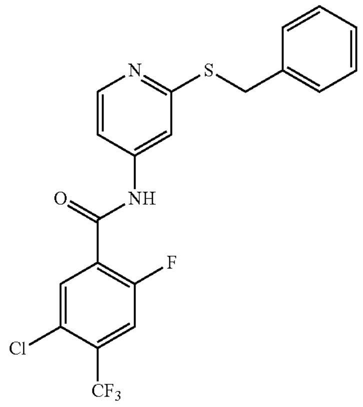

2-(benzylthio)pyridin-4-amine (680 mg, 3.148 mmol) was dissolved in thionyl chloride (1 mL). After replacement with nitrogen three times, the mixture was stirred at 80° C. for 2 hours, and spun dry for later use. 5-chloro-2-fluoro-4-(trifluoromethyl)benzoic acid (763.6 mg, 3.148 mmol) was dissolved in methylene chloride (8 mL), and N,N-diisopropylethylamine (1.63 g, 12.592 mmol) was added dropwise in an ice bath at 0° C. to obtain a reaction solution. The reaction solution which had been previously spun dry for later use was dissolved in methylene chloride (1 mL), and was added dropwise in an ice bath at 0° C. to the above obtained reaction solution. The resulting solution was stirred at room temperature for 16 hours. The reaction was stopped. The reaction solution was spun dry, and the residue was adsorbed to silica gel and separated and purified by silica gel column chromatography (mobile phase: petroleum ether: ethyl acetate=5:1) to obtain the title compound (370 mg, yield: 26.7%, colorless oily matter).

MS (ESI): m/z 441.1 $[M+H]^+$;

Step 4: N-(2-(benzylthio)pyridin-4-yl)-5-chloro-2-(4-fluoro-2-methylphenoxy)-4-(trifluoromethyl)benzamide

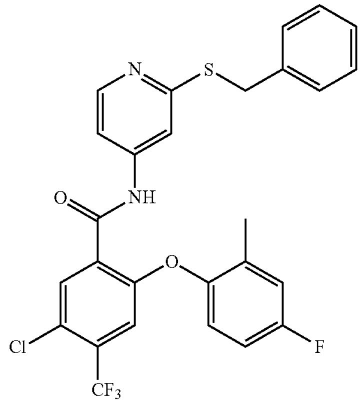 [SMILES: Cc1cc(F)ccc1Oc1cc(C(F)(F)F)c(Cl)cc1C(=O)Nc1ccnc(SCc2ccccc2)c1]

N-(2-(benzylthio)pyridin-4-yl)-5-chloro-2-fluoro-4-(trifluoromethyl)benzamide (330 mg, 0.749 mmol) was dissolved in N,N-dimethylformamide (3.3 mL), and 4-fluoro-2-methylphenol (94.3 mg, 0.749 mmol) and cesium carbonate (487.8 mg, 1.497 mmol) were added. The mixture was stirred in an oil bath at 100° C. for 1 hour. The reaction was stopped, and the reaction solution was quenched by adding water (5 ml). The aqueous phase was extracted using ethyl acetate (10 ml×3). The organic phases were combined, washed with a saturated saline solution (5 ml×2), dried over anhydrous sodium sulfate, and filtered. The filtrate was spun dry in vacuo to obtain a crude product, and the crude product was separated and purified by silica gel column chromatography (mobile phase: petroleum ether:ethyl acetate=5:1) to obtain the title compound (343 mg, yield: 83.9%, colorless oily matter).

MS (ESI): m/z 547.0 $[M+H]^+$;

Step 5: 4-(5-chloro-2-(4-fluoro-2-methylphenoxy)-4-(trifluoromethyl)benzamido)pyridine-2-sulfonyl chloride

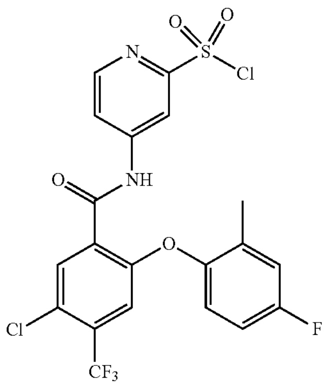 [SMILES: Cc1cc(F)ccc1Oc1cc(C(F)(F)F)c(Cl)cc1C(=O)Nc1ccnc(S(=O)(=O)Cl)c1]

N-(2-(benzylthio)pyridin-4-yl)-5-chloro-2-(4-fluoro-2-methylphenoxy)-4-(trifluoromethyl)benzamide (100 mg, 0.183 mmol) was placed in a three-necked flask, and nitrogen replacement was performed. To the flask was added (glacial acetic acid:water:dichloromethane=7:1:2) (2 mL), and 1,3-dichloro-5,5-dimethylimidazolidine-2,4-dione (108 mg, 0.548 mmol) was added. The mixture was stirred at room temperature for 3 hours. The reaction was stopped, and the reaction solution was quenched by adding water (3 ml). The aqueous phase was extracted using dichloromethane (5 ml×3). The organic phases were combined, washed with a saturated saline solution (3 ml×2), dried over anhydrous sodium sulfate, and filtered. The filtrate was spun dry in vacuo to obtain the title compound (80 mg, crude product, pale yellow solid).

MS (ESI): m/z 523.1 $[M+H]^+$;

Step 6: Tert-butyl (2-((4-(5-chloro-2-(4-fluoro-2-methylphenoxy)-4-(trifluoromethyl)benzamido)pyridine)-2-sulfonamido)ethyl)(methyl)carbamate

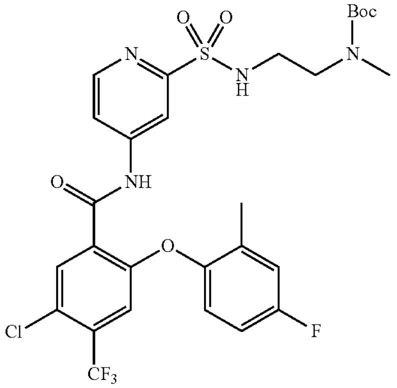 [SMILES: Cc1cc(F)ccc1Oc1cc(C(F)(F)F)c(Cl)cc1C(=O)Nc1ccnc(S(=O)(=O)NCCN(C)C(=O)OC(C)(C)C)c1]

4-(5-chloro-2-(4-fluoro-2-methylphenoxy)-4-(trifluoromethyl)benzamido)pyridine-2-sulfonyl chloride (120 mg, 0.229 mmol) was dissolved in dichloromethane (1 ml), and a solution of tert-butyl (2-aminoethyl)(methyl)carbamate (39.9 mg, 0.229 mmol) in pyridine (1 mL) was added dropwise at 0° C. The mixture was stirred at room temperature for 2 hours. The reaction was stopped, and the reaction solution was quenched by adding a saturated sodium bicarbonate solution (3 ml). The aqueous phase was extracted using ethyl acetate (5 ml×3). The organic phases were combined, washed with a saturated saline solution (2 ml×2), dried over anhydrous sodium sulfate, and filtered. The filtrate was spun dry in vacuo to obtain a crude product. The crude product was separated and purified by silica gel column chromatography (mobile phase: petroleum ether: ethyl acetate=1:1) to obtain the title compound (45 mg, yield: 29.8%, pale yellow solid).

MS (ESI): m/z 661.2 $[M+H]^+$;

Step 7: 5-chloro-2-(4-fluoro-2-methylphenoxy)-N-(2-(N-(2-(methylamino))ethyl)sulfamoyl)pyridin-4-yl)-4-(trifluoromethyl)benzamide (Compound 1)

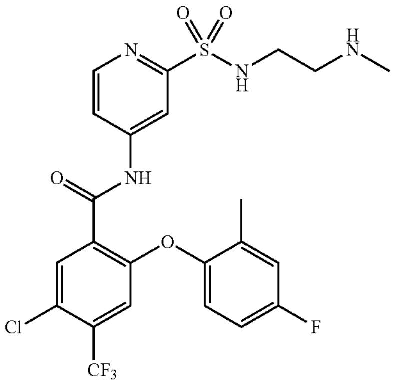 [SMILES: CNCCNS(=O)(=O)c1cc(NC(=O)c2cc(Cl)c(C(F)(F)F)cc2Oc2ccc(F)cc2C)ccn1]

Tert-butyl (2-((4-(5-chloro-2-(4-fluoro-2-methylphenoxy)-4-(trifluoromethyl)benzamido)pyridine)-2-sulfonamido)ethyl)(methyl)carbamate (59 mg, 0.089 mmol) was dissolved in dichloromethane (3 mL), and trifluoroacetic acid (1 mL) was added at 0° C. in an ice bath. The mixture was stirred at room temperature for 1 hour. The reaction was stopped, and the reaction solution was spun in vacuo to remove the solvent to obtain a crude product. The crude product was purified by reverse phase preparative chromatography (elution system: ammonia water, water, and acetonitrile) to obtain the title compound (18.7 mg, yield: 37.5%, brown-yellow solid).

MS (ESI): m/z 561.1 $[M+H]^+$;

$^1H$ NMR (400 MHz, DMSO-$d_6$) δ 11.41 (s, 1H), 8.62 (d, J=5.4 Hz, 1H), 8.26 (d, J=1.4 Hz, 1H), 8.12 (s, 1H), 7.77 (d, J=5.3 Hz, 1H), 7.23-7.17 (m, 1H), 7.10 (dd, J=7.1, 4.6 Hz, 3H), 2.96 (t, J=6.5 Hz, 2H), 2.47 (t, J=6.5 Hz, 2H), 2.17 (s, 3H), 2.16 (s, 3H).

Example 2

(R)-5-chloro-2-(4-fluoro-2-methylphenoxy)-N-(2-(N-(pyrrolidin-3-yl)sulfamoyl)pyridin-4-yl)-4-(trifluoromethyl)benzamide (Compound 2)

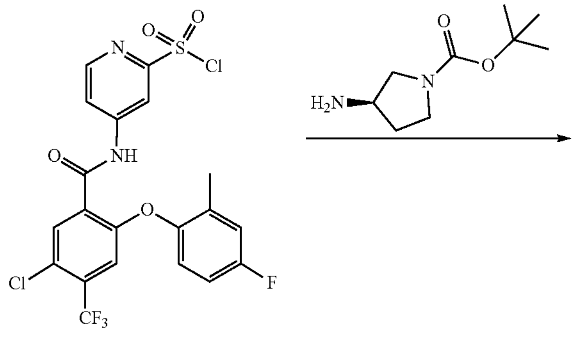

1F

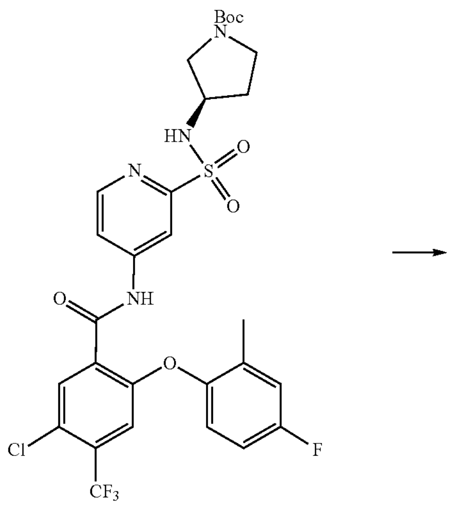

2A

-continued

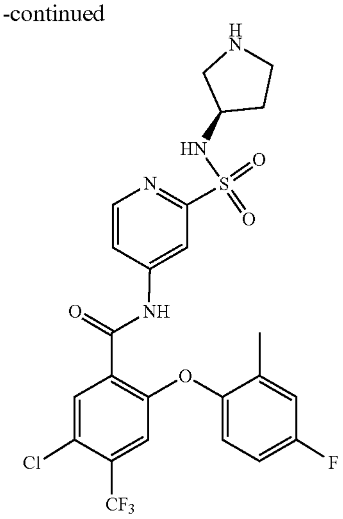

Compound 2

Step 1: Tert-butyl (R)-3-((4-(5-chloro-2-(4-fluoro-2-methylphenoxy)-4-(trifluoromethyl)-benzamido) pyridine)-2-sulfonamido)pyrrolidine-1-carboxylate

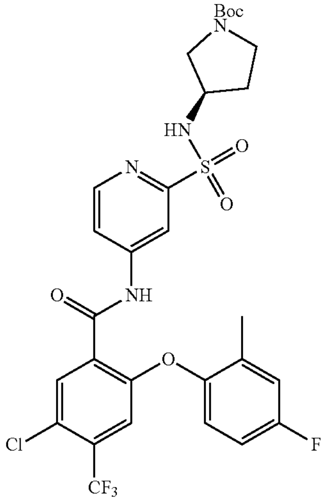 [SMILES: Cc1cc(F)ccc1Oc1cc(C(F)(F)F)c(Cl)cc1C(=O)Nc1ccnc(S(=O)(=O)N[C@@H]2CCN(C(=O)OC(C)(C)C)C2)c1]

4-(5-chloro-2-(4-fluoro-2-methylphenoxy)-4-(trifluoromethyl)benzamido)pyridine-2-sulfonyl chloride (300 mg, 0.57 mmol) and tert-butyl (R)-3-aminopyrrolidine-1-carboxylate (107 mg, 0.57 mmol) were dissolved in a mixed solution of pyridine (2 mL) and dichloromethane (4 mL), and were allowed to react at 0° C. for 2 hours. The reaction was stopped, and the mixture was spun in vacuo to remove the solvent. The residue was diluted by adding water (10 mL), neutralized using a 1 N hydrochloric acid solution, and extracted with ethyl acetate (20 mL×3). The extract was dried over anhydrous sodium sulfate, and filtered. The filtrate was spun dry under reduced pressure, and the residue was separated and purified by column chromatography (silica gel, petroleum ether:ethyl acetate=1:1) to obtain the title compound (222 mg, yield: 58%, yellow solid). MS (ESI): m/z 673.2 $[M+H]^+$;

Step 2: (R)-5-chloro-2-(4-fluoro-2-methylphenoxy)-N-(2-(N-(pyrrolidin-3-yl)sulfamoyl)pyridin-4-yl)-4-(trifluoromethyl)benzamide (Compound 2)

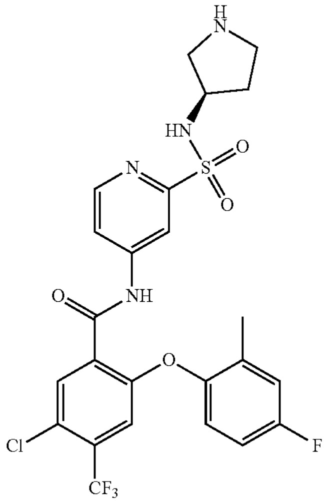 [SMILES: Cc1cc(F)ccc1Oc1cc(C(F)(F)F)c(Cl)cc1C(=O)Nc1ccnc(S(=O)(=O)N[C@@H]2CCNC2)c1]

Tert-butyl (R)-3-((4-(5-chloro-2-(4-fluoro-2-methylphenoxy)-4-(trifluoromethyl)-benzamido)pyridine)-2-sulfonylamino)pyrrolidine-1-carboxylate (210 mg, 0.312 mmol) was dissolved using a mixed solvent of trifluoroacetic acid (2 mL) and dichloromethane (6 mL), and was allowed to react at room temperature for 2 hours. The reaction was stopped, and the mixture was spun in vacuo to remove the solvent. The residue was diluted by adding water (10 mL), and extracted with ethyl acetate (20 mL×3). The extract was dried over anhydrous sodium sulfate. After filtration, the filtrate was spun dry under reduced pressure, and the residue was purified by preparative high performance liquid chromatography (elution system: formic acid, water, and acetonitrile) to obtain the title compound (122.14 mg, yield: 68%, white solid).

MS (ESI): m/z 573.0 $[M+H]^+$;

$^1H$ NMR (400 MHz, DMSO-$d_6$) δ 11.40 (s, 1H), 8.65 (d, J=5.4 Hz, 1H), 8.34 (d, J=1.7 Hz, 1H), 8.12 (s, 1H), 7.80 (dd, J=5.4, 1.9 Hz, 1H), 7.21 (dd, J=9.2, 2.3 Hz, 1H), 7.15-7.06 (m, 3H), 4.05-3.96 (m, 1H), 3.22 (dd, J=11.8, 6.6 Hz, 1H), 3.15 (dd, J=15.2, 7.8 Hz, 1H), 3.10-3.05 (m, 1H), 2.96 (dd, J=11.8, 5.4 Hz, 1H), 2.17 (s, 3H), 2.00-1.93 (m, 1H), 1.81-1.74 (m, 1H).

Example 3

(S)-5-chloro-2-(4-fluoro-2-methylphenoxy)-N-(2-(N-(pyrrolidin-3-yl)sulfamoyl)pyridin-4-yl)-4-(trifluoromethyl)benzamide (Compound 3)

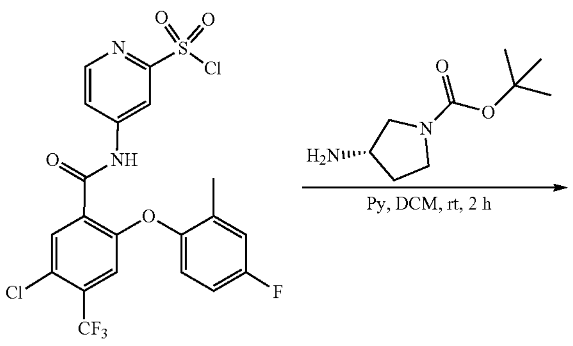

1F

-continued

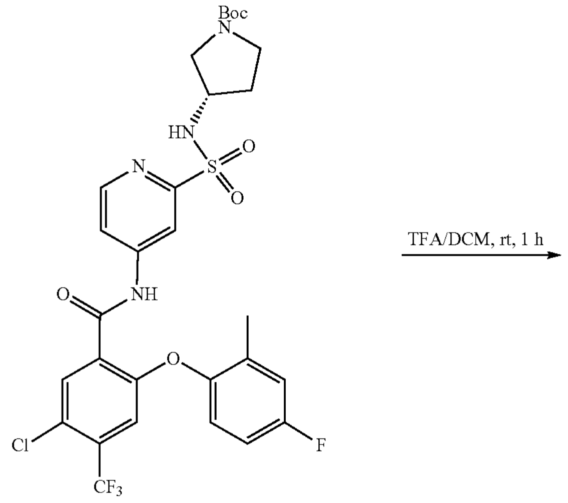

3A

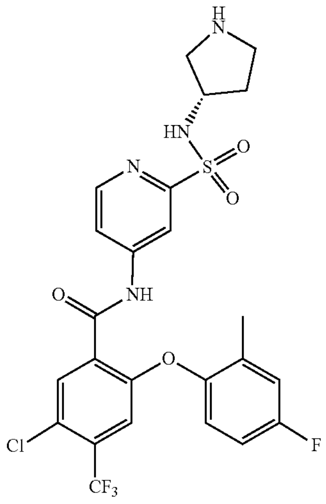

Compound 3

Step 1: Tert-butyl (S)-3-((4-(5-chloro-2-(4-fluoro-2-methylphenoxy)-4-(trifluoromethyl)benzamido)pyridine)-2-sulfonamido)pyrrolidine-1-carboxylate

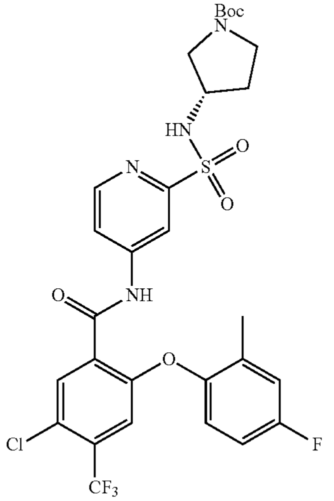 [SMILES: Cc1cc(F)ccc1Oc1cc(C(F)(F)F)c(Cl)cc1C(=O)Nc1ccnc(S(=O)(=O)N[C@H]2CCN(C(=O)OC(C)(C)C)C2)c1]

4-(5-chloro-2-(4-fluoro-2-methylphenoxy)-4-(trifluoromethyl)benzamido)pyridine-2-sulfonyl chloride (300 mg, 0.57 mmol) and tert-butyl (S)-3-aminopyrrolidine-1-carboxylate (107 mg, 0.57 mmol) were dissolved in a mixed solution of pyridine (2 mL) and dichloromethane (4 mL), and were allowed to react at 0° C. for 2 hours. The reaction was stopped, and the mixture was spun in vacuo to remove the solvent. The residue was diluted by adding water (10 mL), neutralized using a 1 N hydrochloric acid solution, and extracted with ethyl acetate (20 mL×3). The extract was dried over anhydrous sodium sulfate and filtered. The filtrate was spun dry under reduced pressure, and the residue was separated and purified by column chromatography (silica gel, petroleum ether:ethyl acetate=1:1) to obtain the title compound (210 mg, yield: 56%, yellow solid). MS (ESI): m/z 673.3 $[M+H]^+$;

Step 2: (S)-5-chloro-2-(4-fluoro-2-methylphenoxy)-N-(2-(N-(pyrrolidin-3-yl)sulfamoyl)pyridin-4-yl)-4-(trifluoromethyl)benzamide (Compound 3)

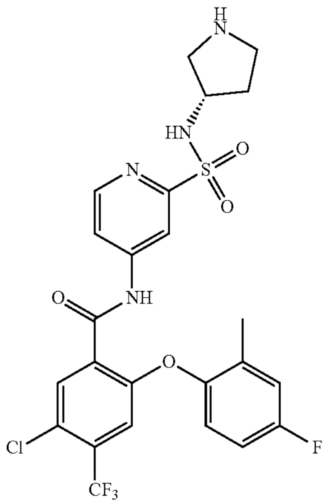 [SMILES: Cc1cc(F)ccc1Oc1cc(C(F)(F)F)c(Cl)cc1C(=O)Nc1ccnc(S(=O)(=O)N[C@H]2CCNC2)c1]

Tert-butyl (S)-3-((4-(5-chloro-2-(4-fluoro-2-methylphenoxy)-4-(trifluoromethyl)benzamido)pyridine)-2-sulfonylamino)pyrrolidine-1-carboxylate (210 mg, 0.312 mmol) was dissolved using a mixed solvent of trifluoroacetic acid (2 mL) and dichloromethane (6 mL), and was allowed to react at room temperature for 2 hours. The reaction was stopped, and the mixture was spun in vacuo to remove the solvent. The residue was diluted by adding water (10 mL), and extracted using ethyl acetate (20 mL×3). The extract was dried over anhydrous sodium sulfate. After preparation and purification by high performance liquid chromatography (elution system: formic acid, water, and acetonitrile), the title compound was obtained (71.26 mg, yield: 40.0%, white solid).

MS (ESI): m/z 572.9 $[M+H]^+$;

$^1H$ NMR (400 MHz, DMSO-$d_6$) δ 8.64 (d, J=5.4 Hz, 1H), 8.33 (s, 1H), 8.31 (d, J=1.8 Hz, 1H), 8.13 (s, 1H), 7.81 (dd, J=5.4, 2.0 Hz, 1H), 7.21 (dd, J=9.2, 2.7 Hz, 1H), 7.14-7.05 (m, 3H), 3.96-3.86 (m, 1H), 3.07-2.97 (m, 2H), 2.92 (d, J=6.6 Hz, 1H), 2.77 (dd, J=11.6, 4.9 Hz, 1H), 2.17 (s, 3H), 1.92-1.87 (m, 1H), 1.67-1.62 (m, 1H).

Example 4

5-chloro-2-(4-fluoro-2-methylphenoxy)-N-(2-(N-(piperidin-4-yl)sulfamoyl)pyridin-4-yl)-4-(trifluoromethyl)benzamide (Compound 4)

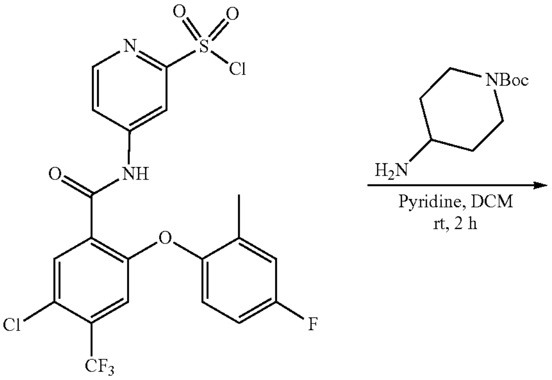

1F

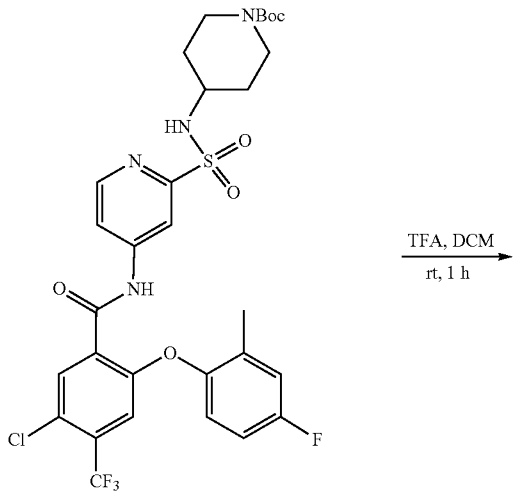

4A

-continued

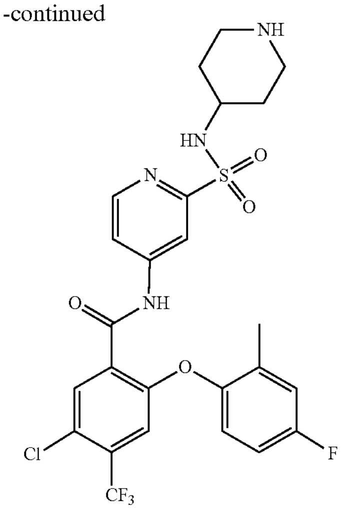

Compound 4

Step 1: Tert-butyl 4-((4-(5-chloro-2-(4-fluoro-2-methylphenoxy)-4-(trifluoromethyl)benzamido)pyridine)-2-sulfonamido)piperidine-1-carboxylate

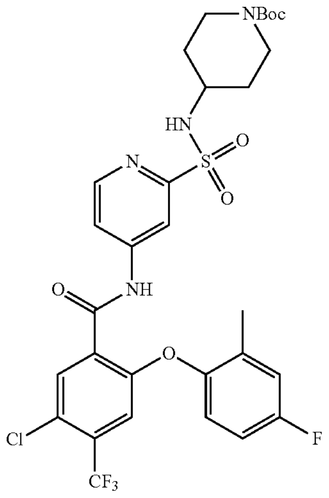 [SMILES: Cc1cc(F)ccc1Oc1cc(C(F)(F)F)c(Cl)cc1C(=O)Nc1ccnc(S(=O)(=O)NC2CCN(C(=O)OC(C)(C)C)CC2)c1]

Tert-butyl 4-aminopiperidine-1-carbamate (76.55 mg, 0.38 mmol) was dissolved in pyridine (2 mL) while stirring at room temperature. The temperature was decreased to 0° C., and 4-(5-chloro-2-(4-fluoro-2-methylphenoxy)-4-(trifluoromethyl)benzamido)pyridine-2-sulfonyl chloride (200 mg, 0.38 mmol) was dissolved in dichloromethane (4 mL) and was added dropwise to the reaction solution. The mixture was maintained at this temperature and was stirred and allowed to react for 2 hours. The reaction was stopped. The reaction solution was poured into water (10 mL), and was extracted using ethyl acetate (10 mL×3). The extracts were combined, washed using 1N HCl (5 mL×3), dried over anhydrous sodium sulfate, and filtered. The filtrate was concentrated under reduced pressure to obtain a crude product. The crude product was separated and purified by column chromatography (silica gel, ethyl acetate:petroleum ether=1:1) to obtain the title compound (120 mg, yield: 45.7%, white solid).

MS (ESI): m/z 687.2 $[M+H]^+$;

Step 2: 5-chloro-2-(4-fluoro-2-methylphenoxy)-N-(2-(N-(piperidin-4-yl)sulfamoyl)pyridin-4-yl)-4-(trifluoromethyl)benzamide (Compound 4)

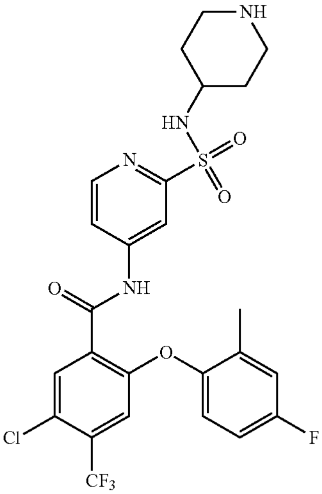 [SMILES: Cc1cc(F)ccc1Oc1cc(C(F)(F)F)c(Cl)cc1C(=O)Nc1ccnc(S(=O)(=O)NC2CCNCC2)c1]

While stirring at room temperature, tert-butyl 4-((4-(5-chloro-2-(4-fluoro-2-methylphenoxy)-4-(trifluoromethyl)benzamido)pyridine)-2-sulfonylamino)piperidine-1-carboxylate (120 mg, 0.17 mmol) was placed in a 25 ml one-neck flask, and was dissolved in dichloromethane (3 mL). Trifluoroacetic acid (1 mL) was added. The mixture was returned to room temperature, and was then stirred and allowed to react at room temperature for 1 hour. The reaction was stopped, and the reaction solution was concentrated under reduced pressure to obtain a crude product. The crude product was separated and purified by preparative high performance liquid chromatography (elution system: formic acid, water, and acetonitrile) to obtain the title compound (87.96 mg, yield: 85.8%, white solid).

MS (ESI): m/z 587.2 $[M+H]^+$;

Example 5

5-chloro-2-(4-fluoro-2-methylphenoxy)-N-(2-(N-(piperidin-4-ylmethyl)sulfamoyl)pyridin-4-yl)-4-(trifluoromethyl)benzamide (Compound 5)

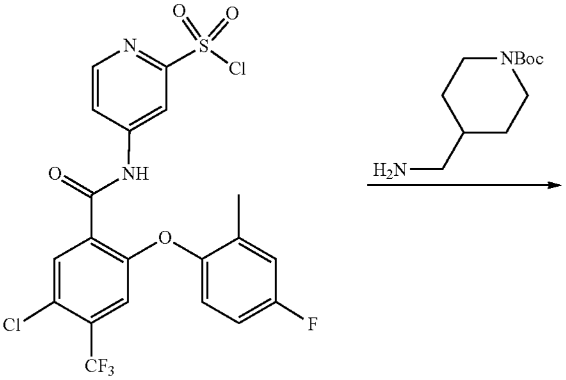

1F

-continued

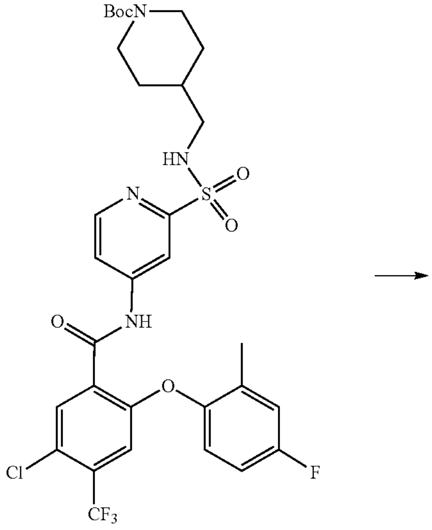

5A

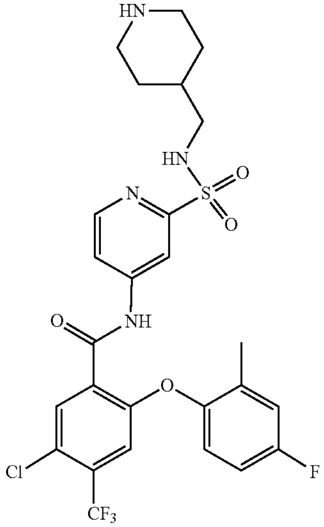

Compound 5

Step 1: Tert-butyl 4-(((4-(5-chloro-2-(4-fluoro-2-methylphenoxy)-4-(trifluoromethyl)benzamido)pyridine)-2-sulfonamido)methyl)piperidine-1-carboxylate

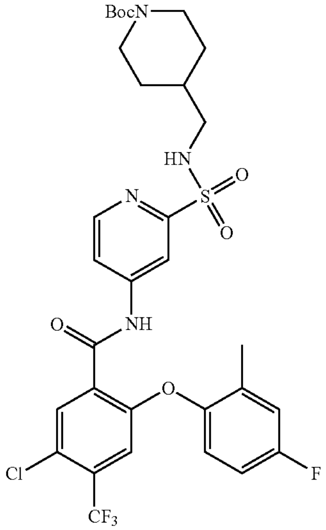 [SMILES: Cc1cc(F)ccc1Oc1cc(C(F)(F)F)c(Cl)cc1C(=O)Nc1ccnc(S(=O)(=O)NCC2CCN(C(=O)OC(C)(C)C)CC2)c1]

At 0° C., 4-(5-chloro-2-(4-fluoro-2-methylphenoxy)-4-(trifluoromethyl)benzamido)pyridine-2-sulfonyl chloride (200 mg, 0.38 mmol) and tert-butyl 4-(aminomethyl)piperidine-1-carboxylate (82 mg, 0.38 mmol) were sequentially added to a mixed solution of pyridine (2 mL) and dichloromethane (4 mL), and were allowed to react for 2 hours. The reaction was stopped, the mixture was spun in vacuo to remove the solvent. The residue was diluted by adding water (10 mL), neutralized using a 1 N hydrochloric acid solution, and extracted with ethyl acetate (20 mL×3). The extract was dried over anhydrous sodium sulfate and filtered. The filtrate was spun dry under reduced pressure, and the residue was separated and purified by column chromatography (silica gel, petroleum ether:ethyl acetate=1:1) to obtain the title compound (110 mg, yield: 41.2%, yellow solid).

MS (ESI): m/z 701.1 $[M+H]^+$;

Step 2: 5-chloro-2-(4-fluoro-2-methylphenoxy)-N-(2-(N-(piperidin-4-ylmethyl)sulfamoyl)pyridin-4-yl)-4-(trifluoromethyl)benzamide (Compound 5)

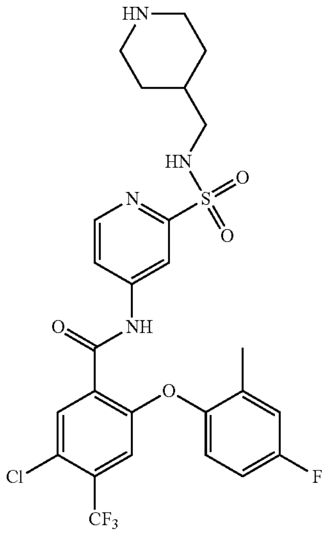 [SMILES: Cc1cc(F)ccc1Oc1cc(C(F)(F)F)c(Cl)cc1C(=O)Nc1ccnc(S(=O)(=O)NCC2CCNCC2)c1]

Tert-butyl 4-(((4-(5-chloro-2-(4-fluoro-2-methylphenoxy)-4-(trifluoromethyl)benzamido)pyridine)-2-sulfonylamino)methyl)piperidine-1-carboxylate (100 mg, 0.143 mmol) was dissolved using a mixed solvent of trifluoroacetic acid (1 mL) and dichloromethane (3 mL), and was allowed to react at room temperature for 2 hours. The reaction was stopped, and the mixture was spun in vacuo to remove the solvent. The residue was diluted by adding water (10 mL), and extracted using ethyl acetate (20 mL×3). The extract was dried over anhydrous sodium sulfate. After filtration, the filtrate was spun dry under reduced pressure, and the residue was purified by preparative high performance liquid chromatography (elution system: formic acid, water, and acetonitrile) to obtain the title compound (40.99 mg, yield: 48%, white solid).

MS (ESI): m/z 601.0 $[M+H]^+$;

$^1H$ NMR (400 MHz, DMSO-$d_6$) δ 11.39 (s, 1H), 8.63 (d, J=5.4 Hz, 1H), 8.29 (d, J=1.7 Hz, 1H), 8.12 (s, 1H), 7.77 (dd, J=5.4, 1.9 Hz, 1H), 7.21 (dd, J=9.2, 2.3 Hz, 1H), 7.14-7.06 (m, 3H), 3.19 (d, J=12.0 Hz, 2H), 2.81 (d, J=6.6 Hz, 2H), 2.74 (t, J=11.8 Hz, 2H), 2.16 (s, 3H), 1.76 (d, J=13.3 Hz, 2H), 1.63 (brs, 1H), 1.21 (dd, J=23.0, 10.9 Hz, 2H).

Example 6

(R)-5-chloro-2-(4-fluoro-2-methylphenoxy)-N-(2-(N-(pyrrolidin-3-ylmethyl)sulfamoyl)pyridin-4-yl)-4-(trifluoromethyl)benzamide (Compound 6)

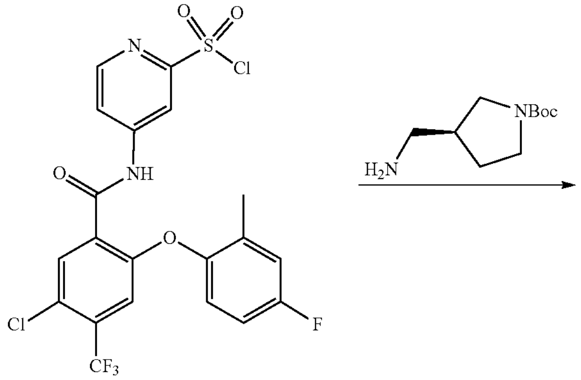

1F

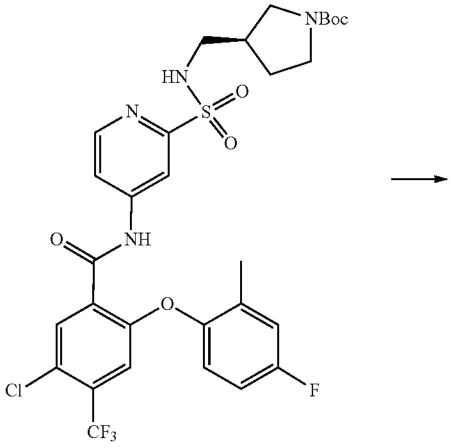

6A

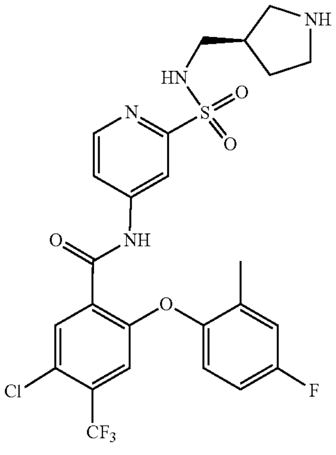

Compound 6

Step 1: Tert-butyl (R)-3-(((4-(5-chloro-2-(4-fluoro-2-methylphenoxy)-4-(trifluoromethyl)benzamido) pyridine)-2-sulfonamido)methyl)pyrrolidine-1-carboxylate

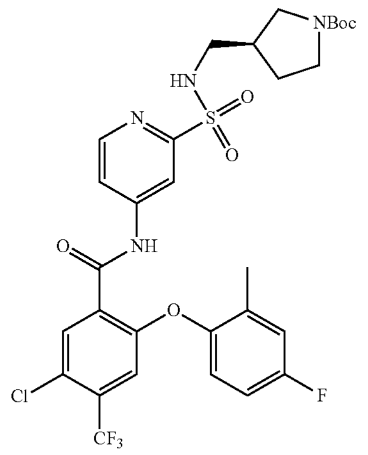 [SMILES: Cc1cc(F)ccc1Oc1cc(C(F)(F)F)c(Cl)cc1C(=O)Nc1ccnc(S(=O)(=O)NC[C@@H]2CCN(C(=O)OC(C)(C)C)C2)c1]

At 0° C., 4-(5-chloro-2-(4-fluoro-2-methylphenoxy)-4-(trifluoromethyl)benzamido)pyridine-2-sulfonyl chloride (300 mg, 0.57 mmol) and tert-butyl (S)-3-(aminomethyl) pyrrolidine-1-carboxylate (115 mg, 0.57 mmol) were dissolved in a mixed solution of pyridine (2 mL) and dichloromethane (4 mL), and were allowed to react for 2 hours. The reaction was stopped, the mixture was spun in vacuo to remove the solvent. The residue was diluted by adding water (10 mL), neutralized using a 1 N hydrochloric acid solution, and extracted with ethyl acetate (20 mL×3). The extract was dried over anhydrous sodium sulfate and filtered. The filtrate was spun dry under reduced pressure, and the residue was separated and purified by column chromatography (silica gel, petroleum ether:ethyl acetate=1:1) to obtain the title compound (256 mg, yield: 65.4%, yellow solid).

MS (ESI): m/z 687.3 $[M+H]^+$;

Step 2: (R)-5-chloro-2-(4-fluoro-2-methylphenoxy)-N-(2-(N-(pyrrolidin-3-ylmethyl)sulfamoyl)pyridin-4-yl)-4-(trifluoromethyl)benzamide (Compound 6)

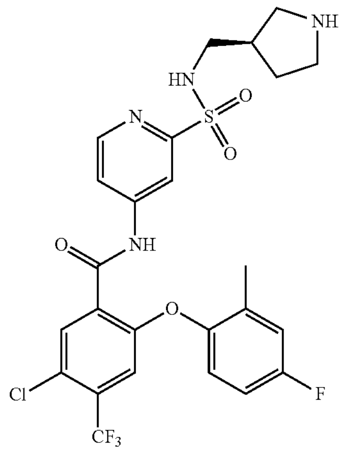 [SMILES: Cc1cc(F)ccc1Oc1cc(C(F)(F)F)c(Cl)cc1C(=O)Nc1ccnc(S(=O)(=O)NC[C@@H]2CCNC2)c1]

Tert-butyl (R)-3-(((4-(5-chloro-2-(4-fluoro-2-methylphenoxy)-4-(trifluoromethyl)benzamido)pyridine)-2-sulfonamido)methyl)pyrrolidine-1-carboxylate (240 mg, 0.35 mmol) was dissolved using a mixed solvent of trifluoroacetic acid (2 mL) and dichloromethane (6 mL), and was stirred and allowed to react at room temperature for 2 hours. The reaction was stopped, and the mixture was spun in vacuo to remove the solvent. The residue was diluted by adding water (10 mL), and extracted using ethyl acetate (20 mL×3). The extract was dried over anhydrous sodium sulfate. After filtration, the filtrate was spun dry under reduced pressure, and the residue was purified by preparative high performance liquid chromatography (elution system: formic acid, water, and acetonitrile) to obtain the title compound (112.26 mg, yield: 54.6%, white solid).

MS (ESI): m/z 587.0 $[M+H]^+$;

$^1H$ NMR (400 MHz, DMSO-$d_6$) δ 11.31 (s, 1H), 8.64 (d, J=5.5 Hz, 1H), 8.31 (d, J=1.7 Hz, 1H), 8.11 (s, 1H), 7.77 (dd, J=5.4, 1.9 Hz, 1H), 7.21 (dd, J=9.2, 2.4 Hz, 1H), 7.14-7.06 (m, 3H), 3.23-3.09 (m, 2H), 3.08-3.02 (m, 1H), 2.98 (d, J=7.0 Hz, 2H), 2.81 (dd, J=11.6, 7.7 Hz, 1H), 2.36 (dt, J=15.3, 7.6 Hz, 1H), 2.16 (s, 3H), 1.97-1.92 (m, 1H), 1.61-1.56 (m, 1H).

Example 7

(S)-5-chloro-2-(4-fluoro-2-methylphenoxy)-N-(2-(N-(pyrrolidin-3-ylmethyl)sulfamoyl)pyridin-4-yl)-4-(trifluoromethyl)benzamide (Compound 7)

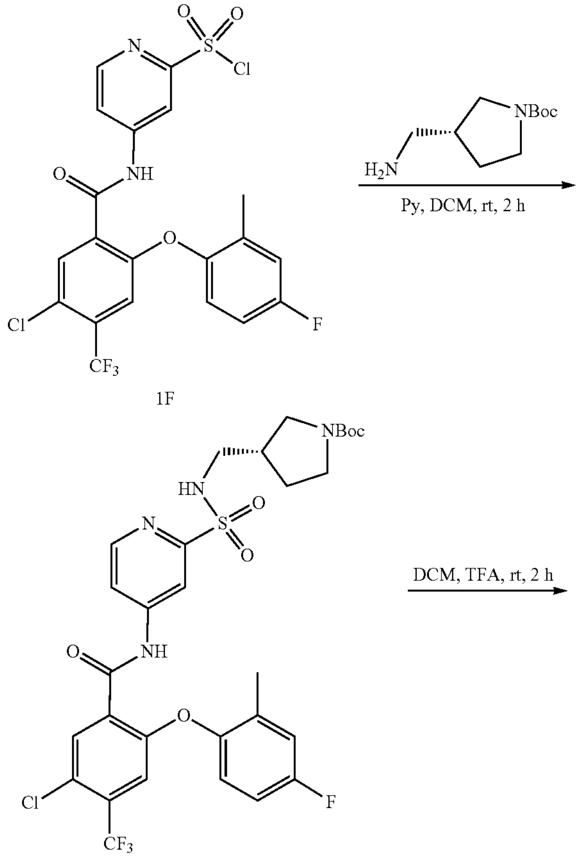

1F

7A

-continued

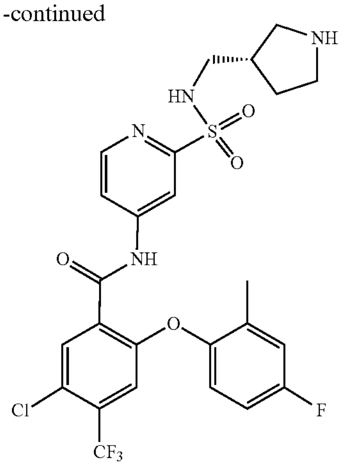

Compound 7

Step 1: Tert-butyl (S)-3-(((4-(5-chloro-2-(4-fluoro-2-methylphenoxy)-4-(trifluoromethyl)benzamido) pyridine)-2-sulfonamido)methyl)pyrrolidine-1-carboxylate

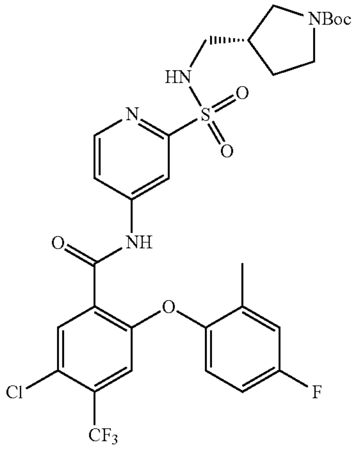 [SMILES: Cc1cc(F)ccc1Oc1cc(C(F)(F)F)c(Cl)cc1C(=O)Nc1ccnc(S(=O)(=O)NC[C@H]2CCN(C(=O)OC(C)(C)C)C2)c1]

At 0° C., 4-(5-chloro-2-(4-fluoro-2-methylphenoxy)-4-(trifluoromethyl)benzamido)pyridine-2-sulfonyl chloride (300 mg, 0.57 mmol) and tert-butyl (R)-3-(aminomethyl) pyrrolidine-1-carboxylate (115 mg, 0.57 mmol) were dissolved in a mixed solution of pyridine (2 mL) and dichloromethane (4 mL), and were allowed to react for 2 hours. The reaction was stopped, and the mixture was spun in vacuo to remove the solvent. The residue was diluted by adding water (10 mL), neutralized using a 1 N hydrochloric acid solution, and extracted with ethyl acetate (20 mL×3). The extract was dried over anhydrous sodium sulfate and filtered. The filtrate was spun dry under reduced pressure, and the residue was separated and purified by column chromatography (silica gel, petroleum ether:ethyl acetate=1:1) to obtain the title compound (256 mg, yield: 65.4%, yellow solid).

MS (ESI): m/z 687.2 $[M+H]^+$;

Step 2: (S)-5-chloro-2-(4-fluoro-2-methylphenoxy)-N-(2-(N-(pyrrolidin-3-ylmethyl)sulfamoyl)pyridin-4-yl)-4-(trifluoromethyl)benzamide (Compound 7)

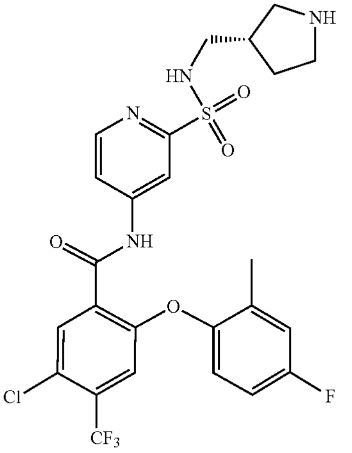 [SMILES: Cc1cc(F)ccc1Oc1cc(C(F)(F)F)c(Cl)cc1C(=O)Nc1ccnc(S(=O)(=O)NC[C@H]2CCNC2)c1]

Tert-butyl (S)-3-(((4-(5-chloro-2-(4-fluoro-2-methylphenoxy)-4-(trifluoromethyl)benzamido)pyridine)-2-sulfonamido)methyl)pyrrolidine-1-carboxylate (240 mg, 0.35 mmol) was dissolved using a mixed solvent of trifluoroacetic acid (2 mL) and dichloromethane (6 mL), and was allowed to react at room temperature for 2 hours. The reaction was stopped, and the mixture was spun in vacuo to remove the solvent. The residue was diluted by adding water (10 mL), and extracted using ethyl acetate (20 mL×3). The extract was dried over anhydrous sodium sulfate. After filtration, the filtrate was spun dry under reduced pressure, and the residue was purified by preparative high performance liquid chromatography (elution system: formic acid, water, and acetonitrile) to obtain the title compound (63.06 mg, yield: 30.7%, white solid).

MS (ESI): m/z 586.9 $[M+H]^+$;

$^1$H NMR (400 MHz, DMSO-$d_6$) δ 8.63 (d, J=5.5 Hz, 1H), 8.36 (s, 1H), 8.29 (d, J=1.7 Hz, 1H), 8.12 (s, 1H), 7.79 (dd, J=5.4, 1.9 Hz, 1H), 7.21 (dd, J=9.2, 2.6 Hz, 1H), 7.15-7.05 (m, 3H), 3.12 (dd, J=11.3, 7.8 Hz, 1H), 3.09-3.03 (m, 1H), 2.99 (d, J=7.8 Hz, 1H), 2.95 (d, J=7.1 Hz, 2H), 2.74 (dd, J=11.3, 7.3 Hz, 1H), 2.31 (dd, J=14.7, 7.3 Hz, 1H), 2.16 (s, 3H), 1.88 (dt, J=13.0, 6.5 Hz, 1H), 1.53 (dq, J=15.4, 7.8 Hz, 1H).

Example 8

(S)-5-chloro-N-(2-(N-(1-ethylpyrrolidin-3-yl)sulfamoyl)pyridin-4-yl)-2-(4-fluoro-2-methylphenoxy)-4-(trifluoromethyl))benzamide (Compound 8)

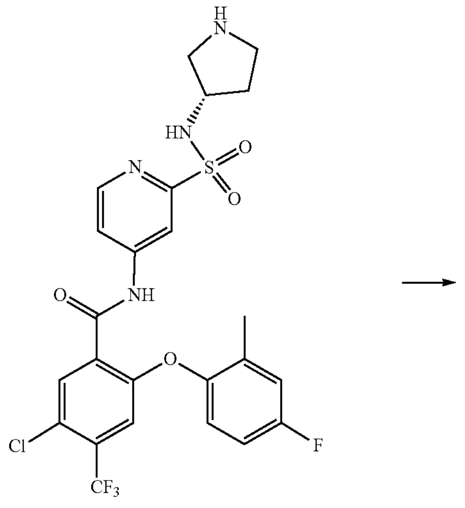

Compound 3

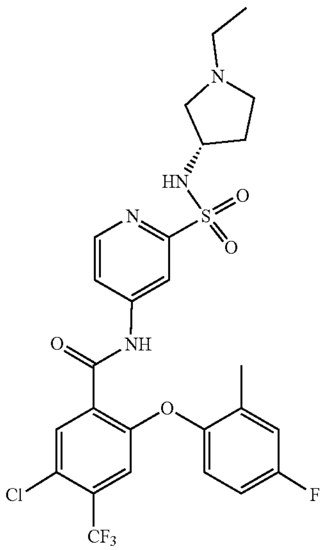

Compound 8

(S)-5-chloro-2-(4-fluoro-2-methylphenoxy)-N-(2-(N-(pyrrolidin-3-yl)sulfamoyl)pyridin-4-yl)-4-(trifluoromethyl)benzamide (102 mg, 0.178 mmol) was dissolved using tetrahydrofuran (1.5 mL), and triethylamine (54 mg, 0.535 mmol) and iodoethane (28 mg, 0.178 mmol) were added. The mixture was sealed and then allowed to react at 70° C. in an oil bath for 16 hours. The reaction was stopped. The reaction solution was adjusted to be slightly acidic by adding 1 N dilute hydrochloric acid, and was extracted using ethyl acetate (30 mL×3). The combined organic phase was washed with a saturated saline solution (20 mL×3), dried over anhydrous sodium sulfate, and filtered. The filtrate was spun dry under reduced pressure. The residue was separated and purified by column chromatography (silica gel, dichloromethane:methanol=10:1), and was then purified by preparative high performance liquid chromatography (elution system: ammonia water, water, and acetonitrile) to obtain the title compound (21.24 mg, yield: 19.9%, white solid)

MS (ESI): m/z 601.2 $[M+H]^+$;

$^1$H NMR (400 MHz, DMSO-$d_6$) δ 11.33 (s, 1H), 8.63 (d, J=5.4 Hz, 1H), 8.27 (d, J=1.8 Hz, 1H), 8.13 (s, 1H), 8.07 (d, J=6.8 Hz, 1H), 7.78 (dd, J=5.4, 1.9 Hz, 1H), 7.20 (dd, J=9.1, 2.2 Hz, 1H), 7.14-7.05 (m, 3H), 3.77 (brs, 1H), 2.59 (dd, J=9.3, 7.3 Hz, 1H), 2.42-2.25 (m, 4H), 2.22-2.14 (m, 4H), 1.94-1.85 (m, 1H), 1.52 (dq, J=8.0, 5.9 Hz, 1H), 0.93 (t, J=7.2 Hz, 3H).

Example 9

(S)-5-chloro-2-(4-fluoro-2-methylphenoxy)-N-(2-(N-(1-propylpyrrolidin-3-yl)sulfonamido)pyridin-4-yl)-4-(trifluoromethyl)benzamide (Compound 9)

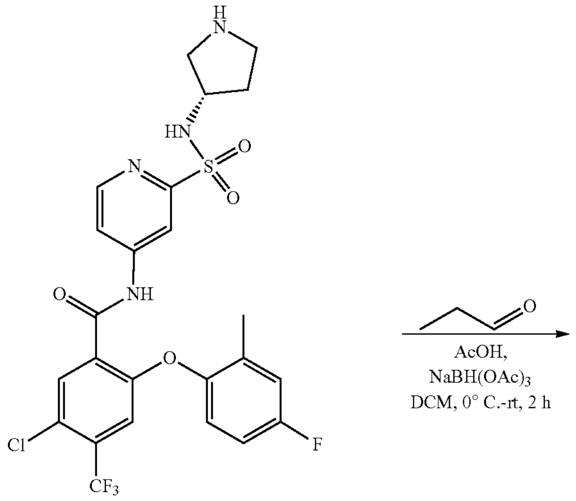

Compound 3

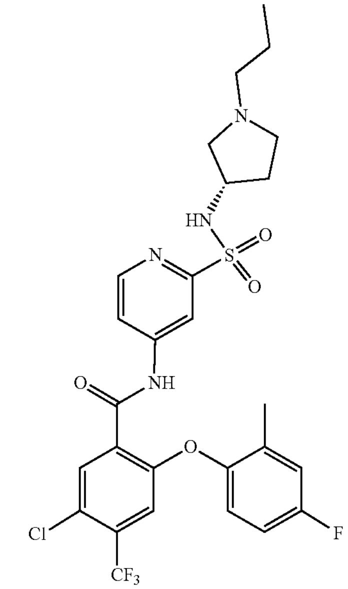

Compound 9

At room temperature, (S)-5-chloro-2-(4-fluoro-2-methylphenoxy)-N-(2-(N-(pyrrolidin-3-yl)sulfamoyl)pyridin-4-yl)-4-(trifluoromethyl)benzamide (80 mg, 0.14 mmol) and propanal (24.33 mg, 0.42 mmol) were dissolved in dichloromethane (2 mL). Acetic acid (25.13 mg, 0.42 mmol) was added, and the mixture was stirred and allowed to react at room temperature for 2 hours. Then, sodium triacetoxyborohydride ($NaBH(OAc)_3$) (88.77 mg, 0.42 mmol) was added, and the mixture was stirred and allowed to react at room temperature for another 2 hours. After the reaction ended, the reaction solution was concentrated under reduced pressure to obtain a crude product. The crude product was separated and purified by preparative high performance liquid chromatography (elution system: formic acid, water, and acetonitrile) to obtain the title compound (27.16 mg, yield: 28.1%, white solid).

MS (ESI): m/z 615.2 $[M+H]^+$;

-continued

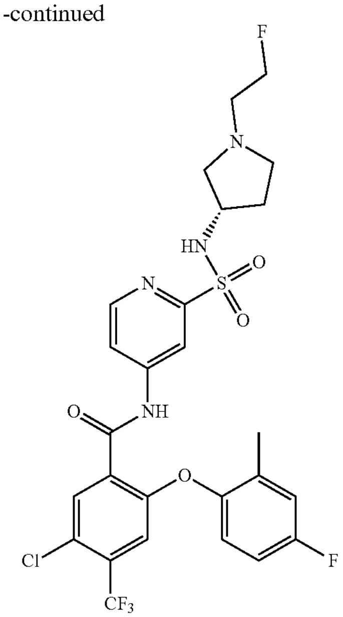

Compound 10

Example 10

(S)-5-chloro-2-(4-fluoro-2-methylphenoxy)-N-(2-(N-(1-(2-fluoroethyl)pyrrolidin-3-yl)sulfamoyl)pyridin-4-yl)-4-(trifluoromethyl)benzamide (Compound 10)

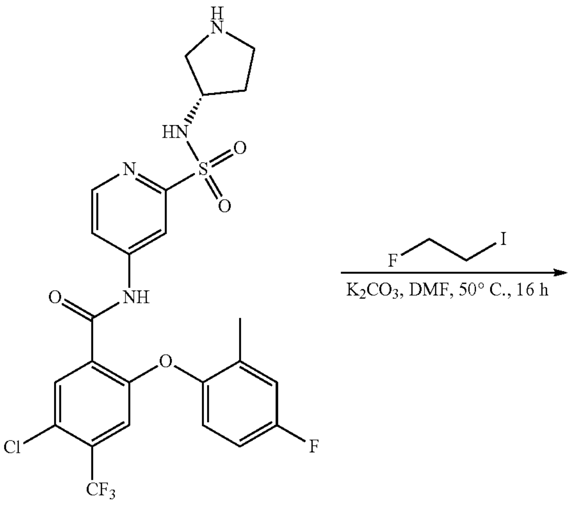

Compound 3

(S)-5-chloro-2-(4-fluoro-2-methylphenoxy)-N-(2-(N-(pyrrolidin-3-yl)sulfamoyl)pyridin-4-yl)-4-(trifluoromethyl)benzamide (70 mg, 0.12 mmol) was dissolved in N,N-dimethylformamide (1 mL), and 1-fluoro-2-iodoethane (21.25 mg, 0.12 mmol) and potassium carbonate (33.7 mg, 0.24 mmol) were added. The mixture was allowed to react at 50° C. in an oil bath for 16 hours. The reaction was stopped. The reaction solution was quenched by adding water (10 mL), and was extracted using ethyl acetate (20 mL×3). The combined organic phases was washed with a saturated saline solution (10 mL×3), dried over anhydrous sodium sulfate, and filtered. The filtrate was spun dry under reduced pressure, and the residue was purified by preparative high performance liquid chromatography (elution system: ammonia water, water, and acetonitrile) to obtain the title compound (28.51 mg, yield: 37.7%, white solid)

MS (ESI): m/z 618.9 $[M]^+$;

$^1H$ NMR (400 MHz, DMSO-$d_6$) δ 11.33 (s, 1H), 8.63 (d, J=5.4 Hz, 1H), 8.27 (s, 1H), 8.15-8.07 (m, 2H), 7.78 (dd, J=5.4, 1.7 Hz, 1H), 7.23-7.17 (m, 1H), 7.13-7.09 (m, 3H), 4.44 (dt, J=44.0, 4.9 Hz, 2H), 3.79 (dd, J=14.4, 6.6 Hz, 1H), 2.72-2.58 (m, 5H), 2.34-2.26 (m, 1H), 2.16 (s, 3H), 1.98-1.83 (m, 1H), 1.58-1.51 (m, 1H).

Example 11

(R)-5-chloro-N-(2-(N-(1-ethylpyrrolidin-3-yl)sulfamoyl)pyridin-4-yl)-2-(4-fluoro-2-methylphenoxy)-4-(trifluoromethyl))benzamide (Compound 11)

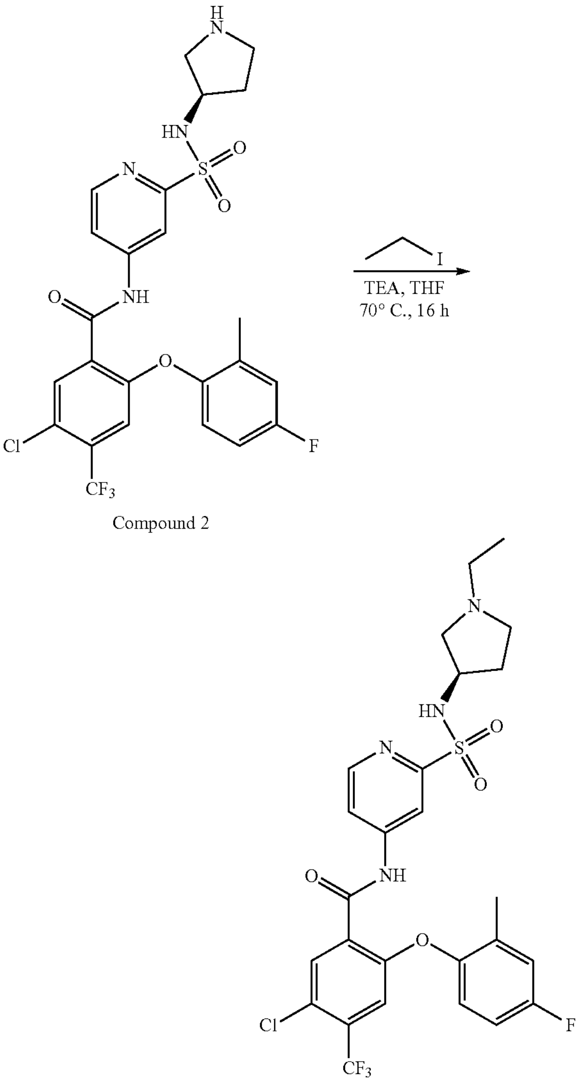

Compound 2

Compound 11

(R)-5-chloro-2-(4-fluoro-2-methylphenoxy)-N-(2-(N-(pyrrolidin-3-yl)sulfamoyl)pyridin-4-yl)-4-(trifluoromethyl)benzamide (80 mg, 0.14 mmol) was dissolved using tetrahydrofuran (2.0 mL), and triethylamine (42.38 mg, 0.42 mmol) and iodoethane (21.78 mg, 0.14 mmol) were added. The mixture was sealed and then allowed to react in an oil bath at 70° C. for 16 hours. The reaction was stopped. The reaction solution was adjusted to be slightly acidic by adding 1 N dilute hydrochloric acid, and was extracted using ethyl acetate (30 mL×3). The combined organic phases was washed with a saturated saline solution (20 mL×3), and dried over anhydrous sodium sulfate. After separation and purification by column chromatography (silica gel, dichloromethane:methanol=10:1) followed by preparation and purification by high performance liquid chromatography (elution system: formic acid, water, and acetonitrile), the title compound (44.72 mg, yield: 42.6%, white solid) was obtained.

MS (ESI): m/z 601.1 $[M+H]^+$;

Example 12

(R)-5-chloro-2-(4-fluoro-2-methylphenoxy)-N-(2-(N-(1-propylpyrrolidin-3-yl)sulfamoyl)pyridin-4-yl)-4-(trifluoromethyl)benzamide (Compound 12)

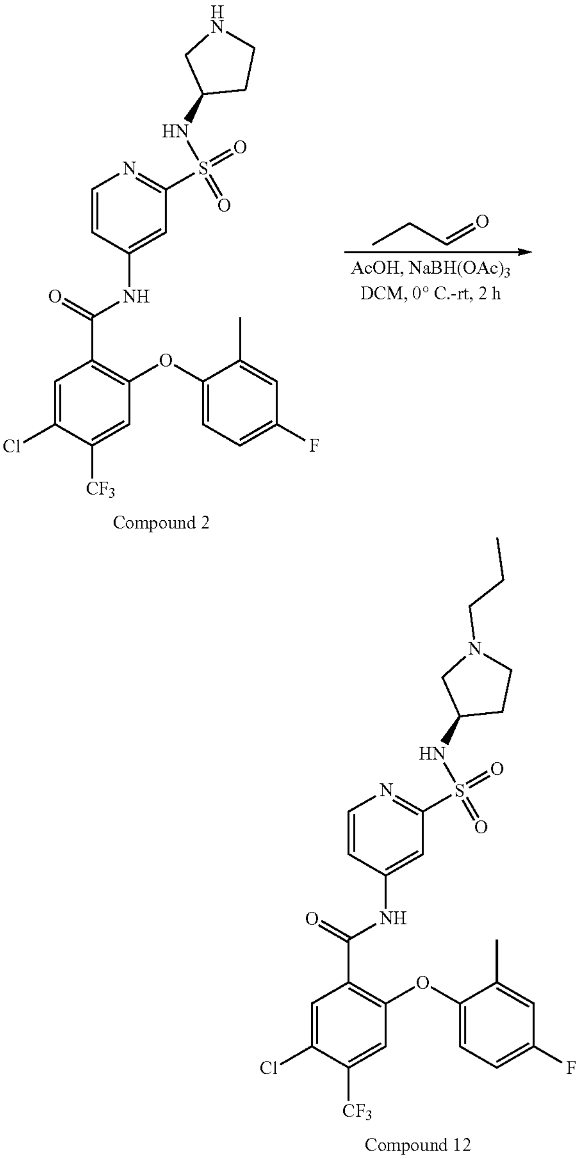

Compound 2

Compound 12

At room temperature, (R)-5-chloro-2-(4-fluoro-2-methylphenoxy)-N-(2-(N-(pyrrolidin-3-yl)sulfamoyl)pyridin-4-yl)-4-(trifluoromethyl)benzamide (80 mg, 0.14 mmol) and propanal (24.32 mg, 0.42 mmol) were dissolved in dichloromethane (2 mL). Acetic acid (25.13 mg, 0.42 mmol) was added, and the mixture was stirred and allowed to react at room temperature for 2 hours. Then, sodium triacetoxyborohydride (88.77 mg, 0.42 mmol) was added, and the mixture was stirred and allowed to react at room temperature for another 2 hours. After the reaction ended, the reaction solution was concentrated under reduced pressure to obtain a crude product. The crude product was separated and purified by preparative high performance liquid chromatography (elution system: formic acid, water, and acetonitrile) to obtain the title compound (27.36 mg, yield: 25.5%, white solid).

MS (ESI): m/z 615.2 $[M+H]^+$;

$^1H$ NMR (400 MHz, DMSO-$d_6$) δ 11.35 (s, 1H), 8.64-8.62 (m, 1H), 8.28-8.27 (m, 1H), 8.15-8.08 (m, 2H), 7.79-7.77 (m, 1H), 7.21-7.19 (m, 1H), 7.13-7.05 (m, 3H), 3.83-3.76 (m, 1H), 2.69-2.64 (m, 1H), 2.46-2.26 (m, 5H), 2.16 (s, 3H), 1.95-1.86 (m, 1H), 1.59-1.50 (m, 1H), 1.40-1.31 (m, 2H), 0.83-0.78 (m, 3H).

Example 13

5-chloro-2-(4-fluoro-2-methylphenoxy)-N-(2-(S-methyliminosulfonyl)pyridin-4-yl)-4-(trifluoromethyl)benzamide (Compound 13)

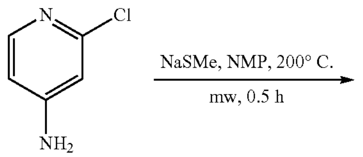

13A

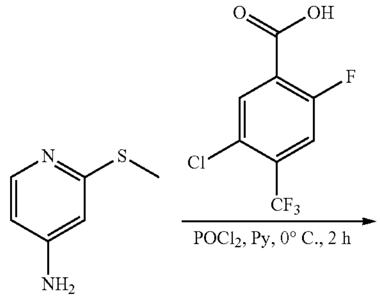

13B

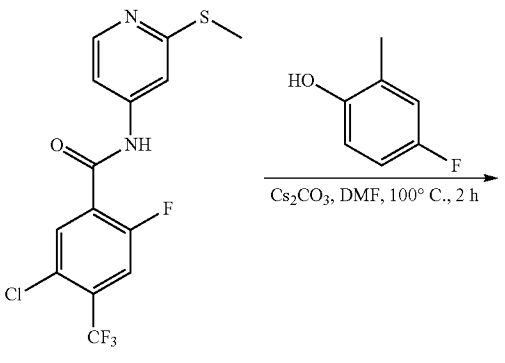

13C

-continued

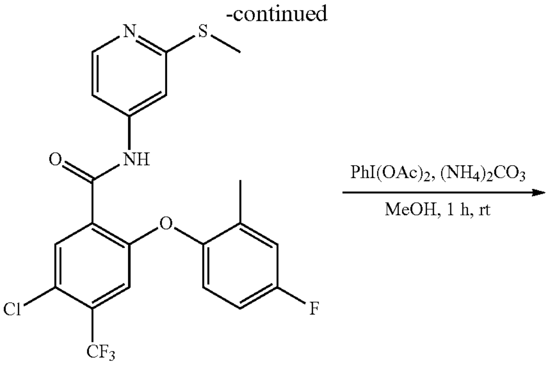

13D

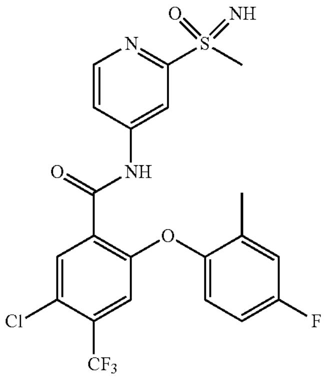

Compound 13

Step 1: 2-(methylthio)pyridin-4-amine

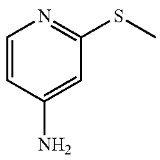

2-chloropyridin-4-amine (1 g, 7.8 mmol) was dissolved in NMP (10 mL), and sodium thiomethoxide (1.12 g, 15.6 mmol) was added. The mixture was allowed to react under microwave at 200° C. for 0.5 hours. The reaction was stopped, and the reaction solution was quenched by adding water (30 ml). The aqueous phase was extracted using chloroform/isopropanol (v:v=3:1) (40 ml×3). The organic phases were combined, dried over anhydrous sodium sulfate, spun dry, and adsorbed to silica gel. After separation and purification by silica gel column chromatography (mobile phase: petroleum ether:ethyl acetate=1:1), the title compound (900 mg, crude product) was obtained, which was directly used in the next reaction.

MS (ESI): m/z 141.2 $[M+H]^+$;

Step 2: 5-chloro-2-fluoro-N-(2-(methylthio)pyridin-4-yl)-4-(trifluoromethyl)benzamide

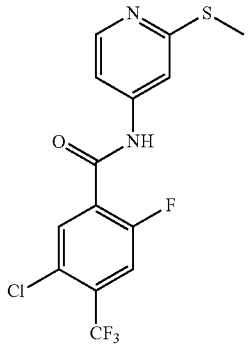 [SMILES: CSc1cc(NC(=O)c2cc(Cl)c(C(F)(F)F)cc2F)ccn1]

2-(methylthio)pyridin-4-amine (400 mg, 2.85 mmol) was dissolved in pyridine (6 mL), 5-chloro-2-fluoro-4-(trifluoromethyl)benzoic acid (691 mg, 2.85 mmol) was added, and phosphorus oxychloride (1.31 g, 8.55 mmol) was added dropwise at 0° C. Then the mixture was stirred and allowed to react for 2 hours. The reaction was stopped. The reaction solution was slowly added dropwise to ice-water (30 ml), and was adjusted to a pH of 5-6 using 1 N hydrochloric acid. The aqueous phase was extracted using ethyl acetate (30 ml×3). The organic phases were combined, washed with a saturated saline solution (5 ml×2), dried over anhydrous sodium sulfate, and filtered. The filtrate was spun dry in vacuo to obtain a crude product, and the crude product was separated and purified by silica gel column chromatography (mobile phase: petroleum ether:ethyl acetate=4:1) to obtain the title compound (720 mg, yield: 69.2%, colorless oily matter).

MS (ESI): m/z 364.9 $[M+H]^+$;

Step 3: 5-chloro-2-(4-fluoro-2-methylphenoxy)-N-(2-(methylthio)pyridin-4-yl)-4-(trifluoromethyl)benzamide

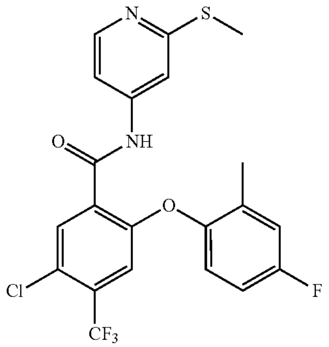 [SMILES: CSc1cc(NC(=O)c2cc(Cl)c(C(F)(F)F)cc2Oc2ccc(F)cc2C)ccn1]

5-chloro-2-fluoro-N-(2-(methylthio)pyridin-4-yl)-4-(trifluoromethyl)benzamide (200 mg, 0.55 mmol) was dissolved in DMF (2 mL), 4-fluoro-2-methylphenol (138 mg, 1.097 mmol) was added, and cesium carbonate (357 mg, 1.097 mmol) was added. The mixture was stirred and allowed to react in an oil bath at 100° C. for 2 hours. The reaction solution was quenched by adding water (10 ml). The aqueous phase was extracted using ethyl acetate (15 ml×3). The organic phases were combined, washed with a saturated saline solution (5 ml×2), dried over anhydrous sodium sulfate, and spun dry in vacuo to obtain a crude product. The crude product was separated and purified by silica gel column chromatography (mobile phase: petroleum ether: ethyl acetate=4:1) to obtain the title compound (273 mg, yield: 92.5%, white solid).

MS (ESI): m/z 471.1 $[M+H]^+$;

Step 4: 5-chloro-2-(4-fluoro-2-methylphenoxy)-N-(2-(S-methyliminosulfonyl)pyridin-4-yl)-4-(trifluoromethyl)benzamide (Compound 13)

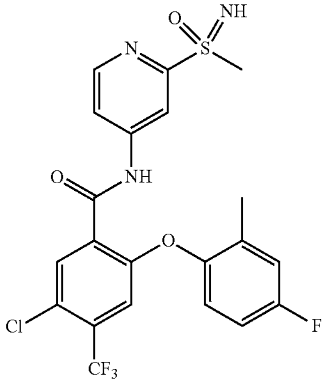 [SMILES: Cc1cc(F)ccc1Oc1cc(C(F)(F)F)c(Cl)cc1C(=O)Nc1ccnc(S(C)(=N)=O)c1]

5-chloro-2-(4-fluoro-2-methylphenoxy)-N-(2-(methylthio)pyridin-4-yl)-4-(trifluoromethyl)benzamide (250 mg, 0.53 mmol) was dissolved in methanol (3 mL), and ammonium carbonate (153 mg, 1.59 mMol) and iodobenzene diacetate (683 mg, 2.12 mMol) were added. The mixture was stirred at room temperature for 1 hour. The reaction was stopped. The reaction solution was spun dry, and the residue was adsorbed to silica gel and separated by silica gel column chromatography (mobile phase: petroleum ether:ethyl acetate=1:1) to obtain a crude product. The crude product was dissolved using DMF, and was purified by reverse phase preparative chromatography (elution system: formic acid, water, and acetonitrile) to obtain the title compound (75.41 mg, yield: 28.2%, white solid).

MS (ESI): m/z 502.1 $[M+H]^+$;

$^1$H NMR (400 MHz, DMSO-$d_6$) δ 8.61 (d, J=5.5 Hz, 1H), 8.41 (s, 1H), 8.38 (s, 1H), 8.10 (s, 1H), 7.77 (d, J=5.3 Hz, 1H), 7.20 (d, J=10.0 Hz, 1H), 7.14-7.04 (m, 3H), 3.12 (s, 3H), 2.15 (s, 3H).

Example 14

5-chloro-2-(4-fluoro-2-(methoxy-$d_3$)phenoxy)-N-(2-(S-methyliminosulfonyl)pyridin-4-yl)-4-(trifluoromethyl)benzamide (Compound 14)

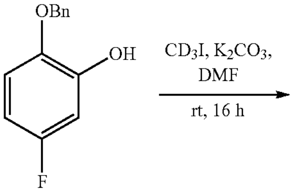

14A

-continued

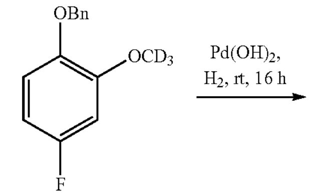

14B

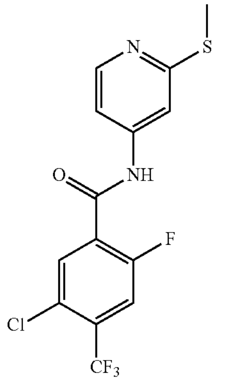

13C

Cs2CO3, DMF, 100° C., 2 h

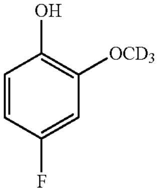

14C

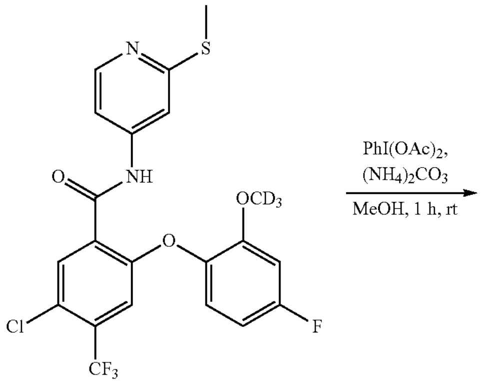

14D

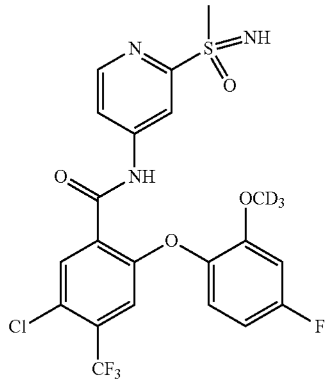

Compound 14

Step 1: 1-(benzyloxy)-4-fluoro-2-(methoxy-$d_3$)benzene

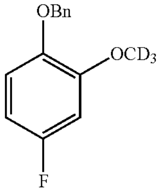

2-(benzyloxy)-5-fluorophenol (400 mg, 1.83 mmol) was dissolved in DMF (4 mL), potassium carbonate (506 mg, 3.66 mmol) was added, and deuterated methyl iodide (319 mg, 2.20 mmol) was added at 0° C. The mixture was stirred and allowed to react at room temperature for 16 hours in a sealed tube. The reaction was stopped, and the reaction solution was quenched by adding water (10 ml). The aqueous phase was extracted using ethyl acetate (15 mL×3). The organic phases were combined, dried over anhydrous sodium sulfate, and filtered. The filtrate was spun dry, and the residue was adsorbed to silica gel and separated and purified by silica gel column chromatography (mobile phase: petroleum ether:ethyl acetate=30:1) to obtain the title compound (340 mg, white solid, yield: 79.1%).

$^1$H NMR (400 MHz, $CDCl_3$) δ 7.44-7.29 (m, 5H), 6.80 (dd, J=8.8, 5.5 Hz, 1H), 6.65 (dd, J=10.2, 2.9 Hz, 1H), 6.52 (td, J=8.5, 2.9 Hz, 1H), 5.10 (s, 2H).

Step 2: 4-fluoro-2-(methoxy-$d_3$)phenol

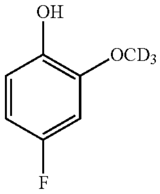

1-(benzyloxy)-4-fluoro-2-(methoxy-$d_3$)benzene (300 mg, 1.275 mmol) was dissolved in methanol (9 mL), and $Pd(OH)_2$ (60 mg) was added. The mixture was stirred at room temperature for 16 h. The reaction was stopped. The reaction solution was filtered, and the filter cake was rinsed using methanol (9 mL×3). The filtrate was spun dry to obtain the title compound (136 mg, yield: 73.5%, brown oily matter).

Step 3: 5-chloro-2-(4-fluoro-2-(methoxy-$d_3$)phenoxy)-N-(2-(methylthio)pyridin-4-yl)-4-(trifluoromethyl)benzamide

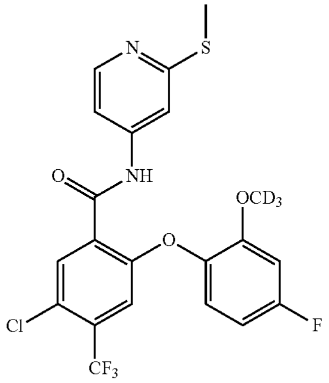

4-fluoro-2-(methoxy-$d_3$)phenol (50 mg, 0.34 mmol) was dissolved in DMF (1 mL), 5-chloro-2-fluoro-N-(2-(methylthio)pyridin-4-yl)-4-(trifluoromethyl)benzamide (62.8 mg, 0.17 mmol) was added, and potassium carbonate (47.5 mg, 0.34 mmol) was added. The mixture was stirred and allowed to react at 100° C. for 2 hours in a sealed tube. The reaction was stopped, and the reaction solution was quenched by adding water (10 ml). The aqueous phase was extracted using ethyl acetate (15 ml×3). The organic phases were combined, washed with a saturated saline solution (5 ml×2), dried over anhydrous sodium sulfate, and filtered. The filtrate was spun dry in vacuo to obtain a crude product. The crude product was separated and purified by silica gel column chromatography (mobile phase: petroleum ether: ethyl acetate=1:1) to obtain the title compound (100 mg, yield: 97.7%, white solid).

MS (ESI): m/z 490.1 $[M+H]^+$;

Step 4: 5-chloro-2-(4-fluoro-2-(methoxy-$d_3$)phenoxy)-N-(2-(S-methyliminosulfonyl)pyridin-4-yl)-4-(trifluoromethyl)benzamide (Compound 14)

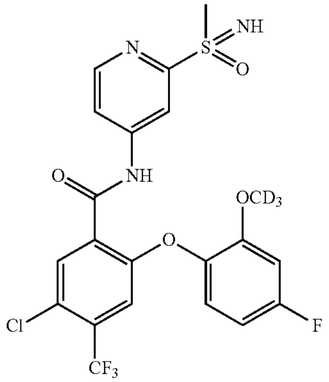

5-chloro-2-(4-fluoro-2-(methoxy-d3)phenoxy)-N-(2-(methylthio)pyridin-4-yl)-4-(trifluoromethyl)benzamide (85 mg, 0.17 mmol) was dissolved in methanol (1 mL), ammonium carbonate (50 mg, 0.52 mmol) was added, and iodobenzene diacetate (224 mg, 0.70 mmol) was added. The mixture was stirred at room temperature for 0.5 hours. The reaction solution was spun dry, and the residue was adsorbed to silica gel and separated by silica gel column chromatography (mobile phase: petroleum ether:ethyl acetate=1:1) to obtain a crude product. The crude product was purified by reverse phase preparative chromatography (elution system: formic acid, water, and acetonitrile) to obtain 5-chloro-2-(4-fluoro-2-(methoxy-$d_3$)phenoxy)-N-(2-(S-methyliminosulfonyl)pyridin-4-yl)-4-(trifluoromethyl)benzamide (FZ008-114) (47.93 mg, yield: 52.9%, white solid).

MS (ESI): m/z 521.1 $[M+H]^+$;

$^1H$ NMR (400 MHz, DMSO-$d_6$) δ 11.31 (s, 1H), 8.63 (d, J=5.4 Hz, 1H), 8.40 (s, 1H), 8.07 (s, 1H), 7.82 (d, J=3.6 Hz, 1H), 7.29 (dd, J=8.8, 5.8 Hz, 1H), 7.14 (dd, J=10.6, 2.8 Hz, 1H), 7.00 (s, 1H), 6.85 (td, J=8.6, 2.9 Hz, 1H), 4.37 (s, 1H), 3.14 (s, 3H).

Resolution of Chiral Isomers of Compound 14:

(S)-5-chloro-2-(4-fluoro-2-(methoxy-$d_3$)phenoxy)-N-(2-(S-methyliminosulfonyl)pyridin-4-yl)-4-(trifluoromethyl) benzamide (R)-5-chloro-2-(4-fluoro-2-(methoxy-$d_3$)phenoxy)-N-(2-(S-methyliminosulfonyl)pyridin-4-yl)-4-(trifluoromethyl) benzamide

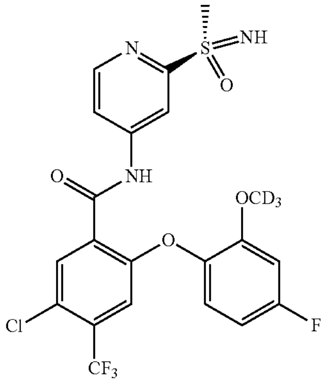

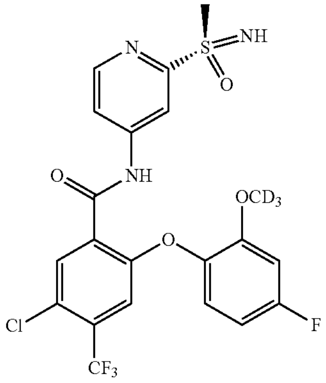

Compound 14 was separated by a chiral preparative separation column (chromatography column: DAICEL CHIRALPAK® IC, 250*25 mm, 10 μm; mobile phase: A—Supercritical $CO_2$; B—MEOH (+0.1% 7.0 mol/1 Ammonia in MEOH), 50% B proportional elution, flow-rate: 100 mL/min, column temperature: room temperature) to obtain single-configuration compound 14E1 (having a shorter retention time) and compound 14E2 (having a longer retention time).

Example 15

5-chloro-2-(2-(methoxy-$d_3$)-4-(trifluoromethoxy) phenoxy)-N-(2-(S-methyliminosulfonyl)pyridin-4-yl)-4-(trifluoromethyl)benzamide (Compound 15)

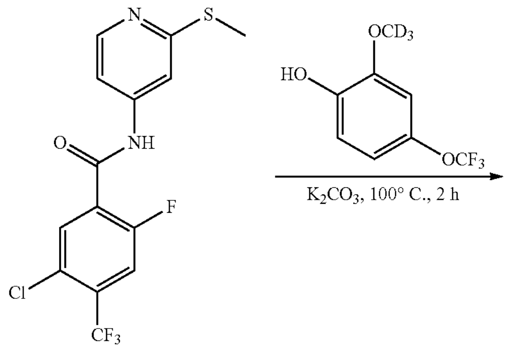

13C

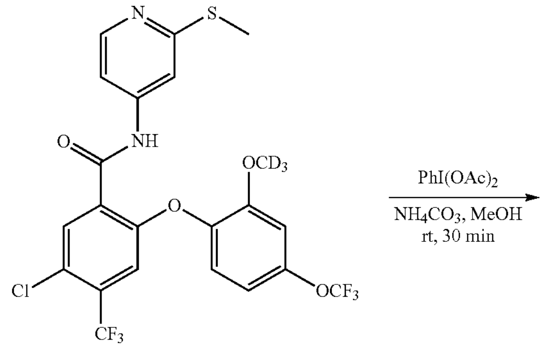

15A

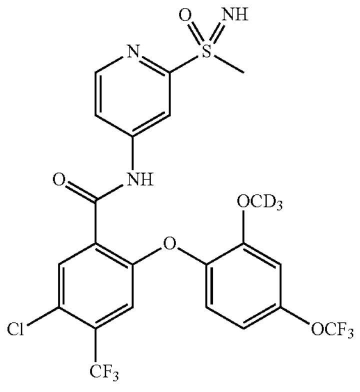

Compound 15

Step 1: 5-chloro-2-(2-(methoxy-$d_3$)-4-(trifluoromethoxy)phenoxy)-N-(2-(methylthio)pyridin-4-yl)-4-(trifluoromethyl)benzamide

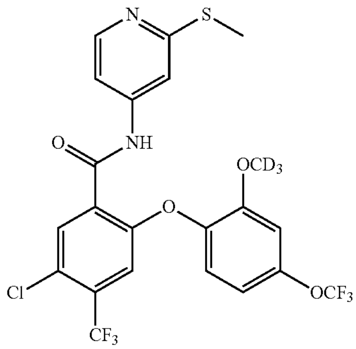

5-chloro-2-fluoro-N-(2-(methylthio)pyridin-4-yl)-4-(trifluoromethyl)benzamide (78 mg, 0.21 mmol) was dissolved in DMF (1 mL), 2-(methoxy-$d_3$)-4-(trifluoromethoxy)phenol (90 mg, 0.43 mmol) was added, and potassium carbonate (59 mg, 0.43 mmol) was added. The mixture was stirred and allowed to react in an oil bath at 100° C. for 2 hours. The reaction was stopped, and the reaction solution was quenched by adding water (10 ml). The aqueous phase was extracted using ethyl acetate (15 ml×3). The organic phases were combined, washed with a saturated saline solution (5 ml×2), dried over anhydrous sodium sulfate, and spun dry in vacuo to obtain a crude product. The crude product was separated and purified by silica gel column chromatography (mobile phase: petroleum ether:ethyl acetate=3:1) to obtain the title compound (100 mg, yield: 84.7%, white solid).

MS (ESI): m/z 556.1 $[M+H]^+$;

Step 2: 5-chloro-2-(2-(methoxy-$d_3$)-4-(trifluoromethoxy)phenoxy)-N-(2-(S-methyliminosulfonyl) pyridin-4-yl)-4-(trifluoromethyl)benzamide (Compound 15)

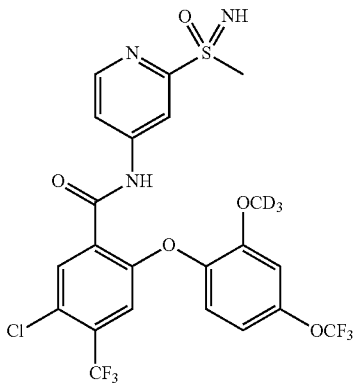

5-chloro-2-(2-(methoxy-d3)-4-(trifluoromethoxy)phenoxy)-N-(2-(methylthio)pyridin-4-yl)-4-(trifluoromethyl) benzamide (88 mg, 0.16 mmol) was dissolved in methanol (1 mL), ammonium carbonate (45.6 mg, 0.48 mmol) was added, and iodobenzene diacetate (204 mg, 0.63 mmol) was added. The mixture was stirred at room temperature for 0.5 hours. The reaction was stopped. The reaction solution was spun dry, and the residue was adsorbed to silica gel and separated by silica gel column chromatography (mobile phase: petroleum ether:ethyl acetate=1:1) to obtain a crude product. The crude product was purified by reverse phase preparative chromatography (elution system: formic acid, water, and acetonitrile) to obtain the title compound (57.30 mg, yield: 61.3%, white solid).

MS (ESI): m/z 587.1 $[M+H]^+$;

$^1H$ NMR (400 MHz, DMSO-$d_6$) δ 11.31 (s, 1H), 8.62 (d, J=5.5 Hz, 1H), 8.38 (s, 1H), 8.09 (s, 1H), 7.80 (dd, J=5.4, 1.8 Hz, 1H), 7.30 (d, J=8.8 Hz, 1H), 7.23-7.12 (m, 2H), 7.00 (d, J=8.8 Hz, 1H), 3.14 (s, 3H).

Example 16

5-chloro-N-(2-(S-methyliminosulfonyl)pyridin-4-yl)-2-(4-(trifluoromethoxy)phenoxy)-4-(trifluoromethyl)benzamide (Compound 16)

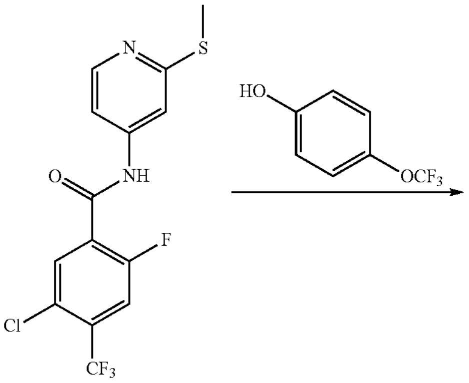

13C

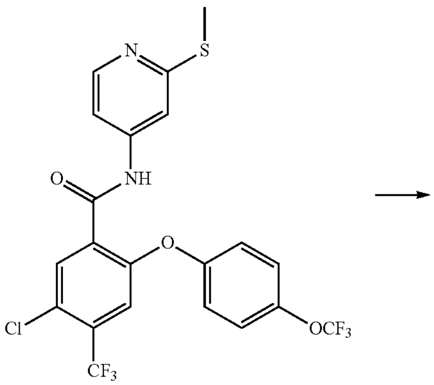

16A

-continued

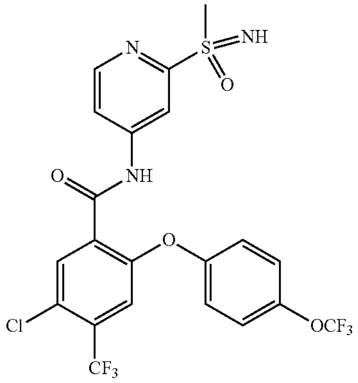

Compound 16

Step 1: 5-chloro-N-(2-(methylthio)pyridin-4-yl)-2-(4-(trifluoromethoxy)phenoxy)-4-(trifluoromethyl) benzamide

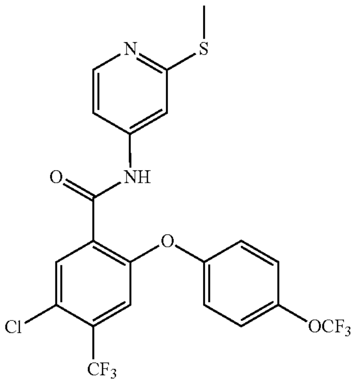 [SMILES: CSc1cc(NC(=O)c2cc(Cl)c(C(F)(F)F)cc2Oc2ccc(OC(F)(F)F)cc2)ccn1]

5-chloro-2-fluoro-N-(2-(methylthio)pyridin-4-yl)-4-(trifluoromethyl)benzamide (70 mg, 0.192 mmol) and 4-(trifluoromethoxy)phenol (68.5 mg, 0.385 mmol) were dissolved in N,N-dimethylformamide (2 mL), and potassium carbonate (54 mg, 0.385 mmol) was added. The mixture was allowed to react in an oil bath at 70° C. for 16 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), and dried over anhydrous sodium sulfate. After separation and purification by column chromatography (silica gel, petroleum ether:ethyl acetate=1:1), the title compound (120 mg, yield: 93.02%, white solid) was obtained.

MS (ESI): m/z 523.2 $[M+H]^+$;

Step 2: 5-chloro-N-(2-(S-methyliminosulfonyl)pyridin-4-yl)-2-(4-(trifluoromethoxy)phenoxy)-4-(trifluoromethyl)benzamide (Compound 16)

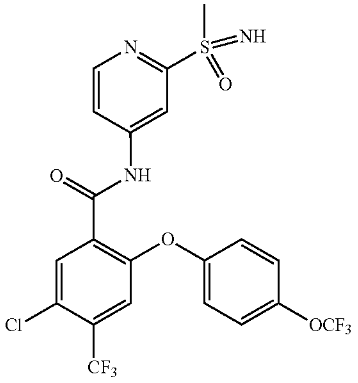 [SMILES: CS(=N)(=O)c1cc(NC(=O)c2cc(Cl)c(C(F)(F)F)cc2Oc2ccc(OC(F)(F)F)cc2)ccn1]

5-chloro-N-(2-(methylthio)pyridin-4-yl)-2-(4-(trifluoromethoxy)phenoxy)-4-(trifluoromethyl)benzamide (100 mg, 0.192 mmol) was dissolved using methanol (2 mL), and ammonium carbonate (55.3 mg, 0.575 mmol) and iodobenzene diacetate (247 mg, 0.767 mmol) were added. The mixture was allowed to react at room temperature for 1 hour. The reaction was stopped, and the mixture was spun in vacuo to remove the solvent. After separation and purification by column chromatography (silica gel, petroleum ether: ethyl acetate=1:9) followed by preparation and purification by high performance liquid chromatography (elution system: ammonium bicarbonate, water, and acetonitrile), the title compound (68.69 mg, yield: 64.8%, white solid) was obtained.

MS (ESI): m/z 554.0 $[M+H]^+$;

$^1$H NMR (400 MHz, DMSO-$d_6$) δ 11.34 (s, 1H), 8.60 (d, J=5.5 Hz, 1H), 8.34 (d, J=1.9 Hz, 1H), 8.15 (s, 1H), 7.76 (dd, J=5.4, 2.0 Hz, 1H), 7.52 (s, 1H), 7.40 (d, J=8.4 Hz, 2H), 7.24-7.20 (m, 2H), 4.36 (s, 1H), 3.13 (s, 3H).

Example 17

5-chloro-2-(4,4-difluoroazepan-1-yl)-N-(2-(S-methyliminosulfonyl)pyridin-4-yl)-4-(trifluoromethyl) benzamide (Compound 17)

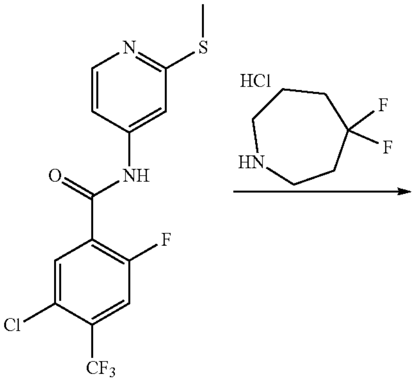

13C

-continued

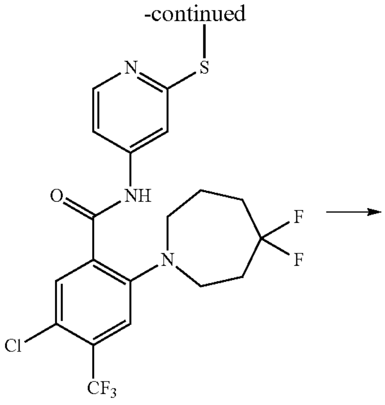

17A

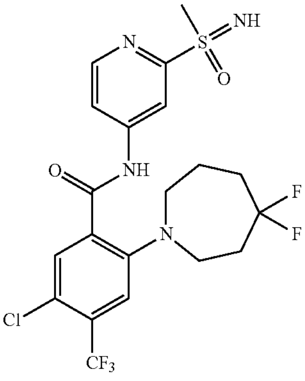

Compound 17

Step 1: 5-chloro-2-(4,4-difluoroazepan-1-yl)-N-(2-(methylthio)pyridin-4-yl)-4-trifluoromethyl)benzamide

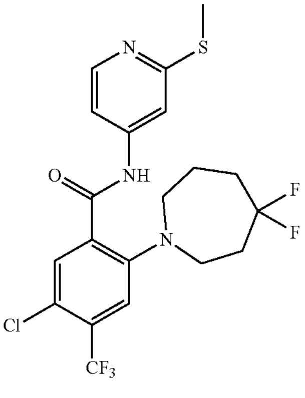 [SMILES: CSc1cc(NC(=O)c2cc(Cl)c(C(F)(F)F)cc2N2CCCC(F)(F)CC2)ccn1]

5-chloro-2-fluoro-N-(2-(methylthio)pyridin-4-yl)-4-(trifluoromethyl)benzamide (100 mg, 0.274 mmol) and 4,4-difluoroazetidine hydrochloride (234 mg, 1.371 mmol) were dissolved in N,N-dimethylformamide (2 mL), and cesium carbonate (625.3 mg, 1.92 mmol) was added. The mixture was allowed to react in an oil bath at 100° C. for 16 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), dried over anhydrous sodium sulfate, and filtered. The filtrate was spun dry under reduced pressure, and the residue was separated and purified by column chromatography (silica gel, petroleum ether:ethyl acetate=1:1) to obtain the title compound (125 mg, yield: 92.6%, white solid).

MS (ESI): m/z 480.1 $[M+H]^+$;

Step 2: 5-chloro-2-(4,4-difluoroazepan-1-yl)-N-(2-(S-methyliminosulfonyl)pyridin-4-yl)-4-(trifluoromethyl)benzamide (Compound 17)

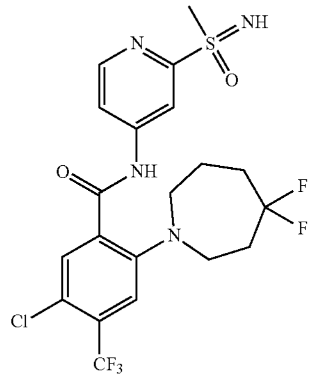 [SMILES: CS(=N)(=O)c1cc(NC(=O)c2cc(Cl)c(C(F)(F)F)cc2N2CCCC(F)(F)CC2)ccn1]

5-chloro-2-(4,4-difluoroazepan-1-yl)-N-(2-(methylthio)pyridin-4-yl)-4-trifluoromethyl)benzamide (65 mg, 0.136 mmol) was dissolved in methanol (2 mL), and ammonium carbonate (40 mg, 0.41 mmol) and iodobenzene diacetate (175 mg, 0.543 mmol) were added. The mixture was allowed to react at room temperature for 1 hour. The reaction was stopped, and the mixture was spun in vacuo to remove the solvent. After separation and purification by column chromatography (silica gel, petroleum ether:ethyl acetate=1:10) followed by preparation and purification by high performance liquid chromatography (elution system: ammonium bicarbonate, water, and acetonitrile), the title compound (35.02 mg, yield: 50.49%, white solid) was obtained.

MS (ESI): m/z 511.1 $[M+H]^+$;

$^1H$ NMR (400 MHz, DMSO-$d_6$) δ 11.24 (s, 1H), 8.63 (d, J=5.3 Hz, 1H), 8.41 (s, 1H), 7.84 (d, J=4.7 Hz, 1H), 7.75 (s, 1H), 7.35 (s, 1H), 4.37 (s, 1H), 3.39-3.32 (m, 4H), 3.15 (s, 3H), 2.24 (brs, 2H), 2.07-2.04 (m, 2H), 1.79 (brs, 2H).

Resolution of Chiral Isomers of Compound 17:

(S)-5-chloro-2-(4,4-difluoroazepan-1-yl)-N-(2-(S-methyliminosulfonyl)pyridin-4-yl)-4-(trifluoromethyl)benzamide (R)-5-chloro-2-(4,4-difluoroazepan-1-yl)-N-(2-(S-methyliminosulfonyl)pyridin-4-yl)-4-(trifluoromethyl)benzamide

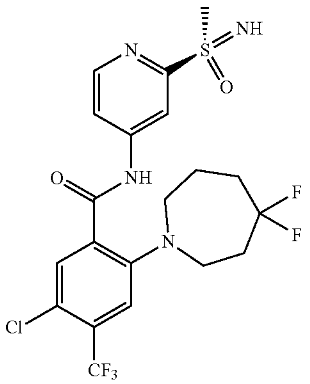

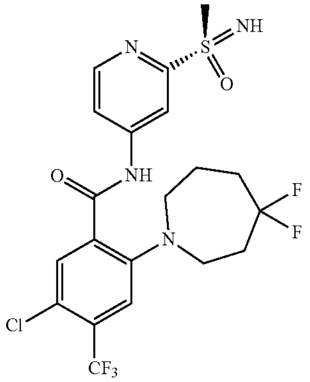

Compound 17 was separated by a chiral preparative separation column (chromatography column: DAICEL CHIRALCEL® OJ, 250*25 mm, 10 μm; mobile phase: A—Supercritical $CO_2$; B—MEOH (+0.1% 7.0 mol/1 Ammonia in MEOH), 25% B proportional elution, flow-rate: 70 mL/min, column temperature: room temperature) to obtain single-configuration compound 17E1 (having a shorter retention time) and compound 17E2 (having a longer retention time).

Example 18

5-chloro-2-((3aR,6aS)-5,5-difluorohexahydrocyclopentadieno[c]pyrrol-2(1H)-yl)-N-(2-(S-methyliminosulphonyl)pyridin-4-yl)-4-(trifluoromethyl)benzamide (Compound 18)

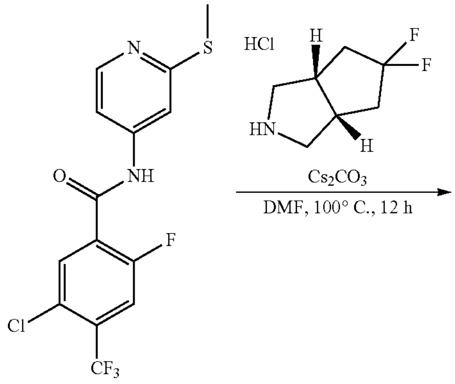

13C

-continued

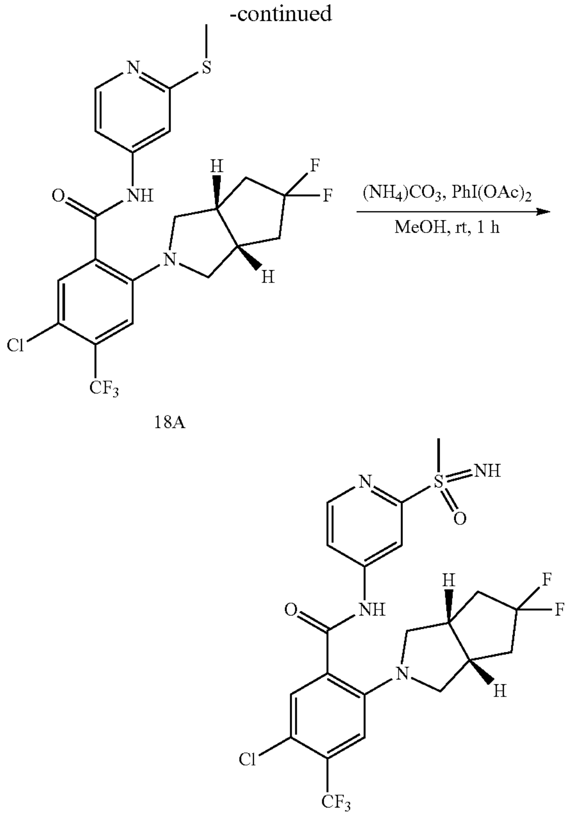

18A

Compound 18

Step 1: 5-chloro-2-((3aR,6aS)-5,5-difluorohexahydrocyclopentadieno[c]pyrrol-2(1H)-yl)-N-(2-(methylthio)pyridin-4-yl)-4-(trifluoromethyl)benzamide

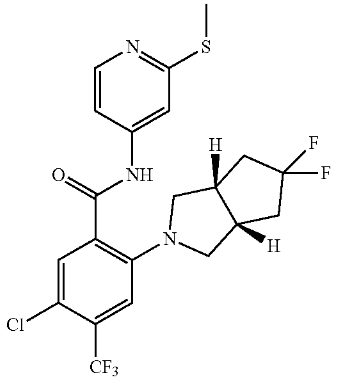 [SMILES: CSc1cc(NC(=O)c2cc(Cl)c(C(F)(F)F)cc2N2C[C@@H]3CC(F)(F)C[C@@H]3C2)ccn1]

5-chloro-2-fluoro-N-(2-(methylthio)pyridin-4-yl)-4-(trifluoromethyl)benzamide (100 mg, 0.27 mmol) was dissolved in DMF (3 mL), and (3aR,6aS)-5,5-difluorohexahydrocyclopentadieno[c]pyrrole hydrochloride (98.8 mg, 0.54 mmol) and cesium carbonate (536 mg, 1.64 mmol) were added. Nitrogen replacement was performed, and the mixture was allowed to react at 100° C. for 12 hours. The reaction was stopped, and water was added to the reaction solution (15 mL). The aqueous phase was extracted using ethyl acetate (15 ml×3). The organic phases were combined, washed with a saturated saline solution (10 ml×2), dried over anhydrous sodium sulfate, and filtered. The filtrate was spun dry in vacuo to obtain a crude product. The crude product was separated and purified by silica gel column chromatography (mobile phase: petroleum ether:ethyl acetate=9:1) to obtain the title compound (100 mg, yield: 74.6%, white solid).

MS (ESI): m/z 492.1 $[M+H]^+$;

Step 2: 5-chloro-2-((3aR,6aS)-5,5-difluorohexahydrocyclopentadieno[c]pyrrol-2(1H)-yl)-N-(2-(S-methyliminosulphonyl)pyridin-4-yl)-4-(trifluoromethyl)benzamide (Compound 18)

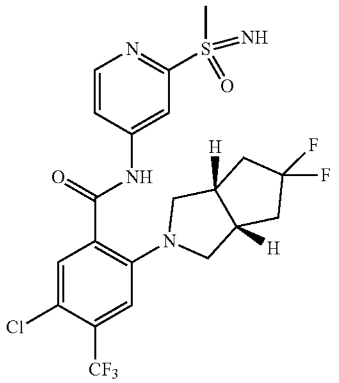 [SMILES: CS(=N)(=O)c1cc(NC(=O)c2cc(Cl)c(C(F)(F)F)cc2N2C[C@@H]3CC(F)(F)C[C@@H]3C2)ccn1]

5-chloro-2-((3aR,6aS)-5,5-difluorohexahydrocyclopentadieno[c]pyrrol-2(1H)-yl)-N-(2-(methylthio)pyridin-4-yl)-4-(trifluoromethyl)benzamide (100 mg, 0.20 mmol) was dissolved in methanol (1.5 mL), and ammonium carbonate (58.6 mg, 0.60 mmol) and iodobenzene oxalate (261.9 mg, 0.81 mmol) were added. The mixture was stirred at room temperature for 1 hour. The reaction was stopped. The reaction solution was spun dry, and was quenched by adding saturated sodium bicarbonate solution water (2 ml). The aqueous phase was extracted using ethyl acetate (5 ml×3). The organic phases were combined, washed with a saturated saline solution (3 ml×2), dried over anhydrous sodium sulfate, and filtered. The filtrate was spun dry in vacuo to obtain a crude product, and the crude product was purified by reverse phase preparative chromatography (elution system: ammonia water, water, and acetonitrile) to obtain the title compound (10 mg, yield: 9.4%, white solid).

MS (ESI): m/z 539.8 $[M+H]^+$;

$^1H$ NMR (400 MHz, DMSO-$d_6$) δ 11.28 (s, 1H), 8.62 (d, J=4.9 Hz, 1H), 8.42 (s, 1H), 7.82 (s, 1H), 7.72 (s, 1H), 7.16 (s, 1H), 4.36 (s, 1H), 3.39 (brs, 2H), 3.19 (d, J=9.6 Hz, 2H), 3.14 (s, 3H), 2.85 (brs, 2H), 2.32 (brs, 2H), 1.98 (brs, 2H).

Example 19

5-chloro-2-((4,4-difluorocyclohexyl)oxy)-N-(2-(S-methyliminosulfonyl)pyridin-4-yl)-4-(trifluoromethyl)benzamide (Compound 19)

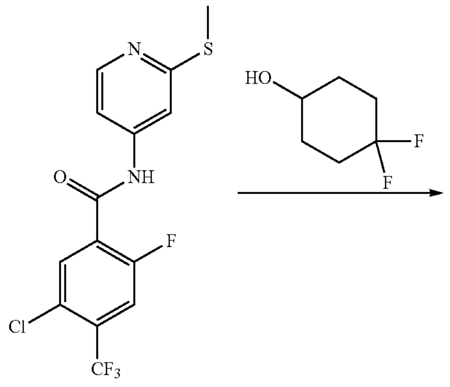

13C

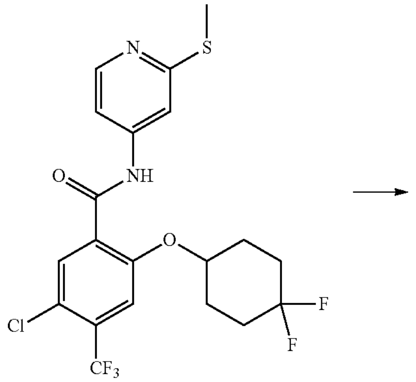

19A

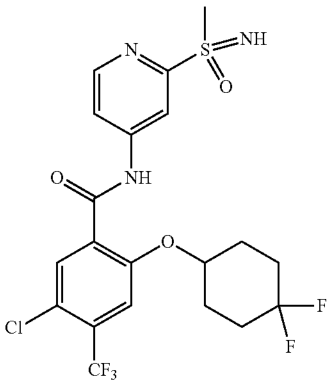

Compound 19

Step 1: 5-chloro-2-((4,4-difluorocyclohexyl)oxy)-N-(2-(methylthio)pyridin-4-yl)-4-(trifluoromethyl)benzamide

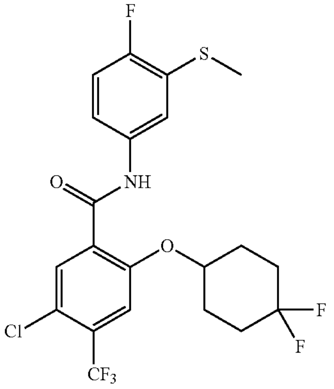 [SMILES: CSc1cc(NC(=O)c2cc(Cl)c(C(F)(F)F)cc2OC2CCC(F)(F)CC2)ccc1F]

5-chloro-2-fluoro-N-(2-(methylthio)pyridin-4-yl)-4-(trifluoromethyl)benzamide (100 mg, 0.274 mmol) and 4,4-difluorocyclohexan-1-ol (150 mg, 1.097 mmol) were dissolved in N,N-dimethylformamide (2 mL), and cesium carbonate (268 mg, 0.823 mmol) was added. The mixture was allowed to react in an oil bath at 100° C. for 16 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), and dried over anhydrous sodium sulfate. After separation and purification by column chromatography (silica gel, petroleum ether:ethyl acetate=1:1), the title compound (200 mg, yield: 98.1%, white solid) was obtained.

MS (ESI): m/z 481.0 $[M+H]^+$;

Step 2: 5-chloro-2-((4,4-difluorocyclohexyl)oxy)-N-(2-(S-methyliminosulfonyl)76yridazi-4-yl)-4-(trifluoromethyl)benzamide (Compound 19)

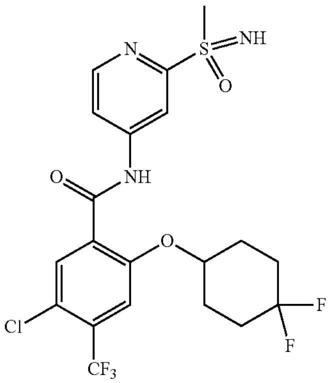 [SMILES: CS(=N)(=O)c1cc(NC(=O)c2cc(Cl)c(C(F)(F)F)cc2OC2CCC(F)(F)CC2)ccn1]

5-chloro-2-((4,4-difluorocyclohexyl)oxy)-N-(2-(methylthio) 76 yridazi-4-yl)-4-(trifluoromethyl)benzamide (190 mg, 0.4 mmol) was dissolved using methanol (2 mL), and ammonium carbonate (114 mg, 1.19 mmol) and iodobenzene diacetate (510 mg, 1.58 mmol) were added. The mixture was allowed to react at room temperature for 1 hour.

The reaction was stopped, and the mixture was spun in vacuo to remove the solvent. After separation and purification by column chromatography (silica gel, petroleum ether: ethyl acetate=1:10) followed by preparation and purification by high performance liquid chromatography (elution system: ammonium bicarbonate, water, and acetonitrile), the title compound (81.2 mg, yield: 39.8%, white solid) was obtained.

MS (ESI): m/z 512.1 $[M+H]^+$;

$^1H$ NMR (400 MHz, DMSO-$d_6$) δ 11.14 (s, 1H), 8.63 (d, J=5.4 Hz, 1H), 8.40 (s, 1H), 7.92 (s, 1H), 7.78 (d, J=5.2 Hz, 1H), 7.66 (s, 1H), 4.96 (brs, 1H), 4.37 (s, 1H), 3.14 (s, 3H), 2.01-1.83 (m, 8H).

Example 20

5-chloro-2-(4-fluoro-2-methylphenoxy)-N-(6-(S-methyliminosulfonyl) 76 yridazine-4-yl)-4-(trifluoromethyl)benzamide (Compound 20)

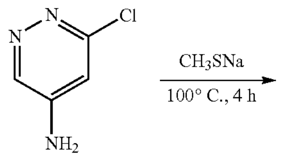

20A

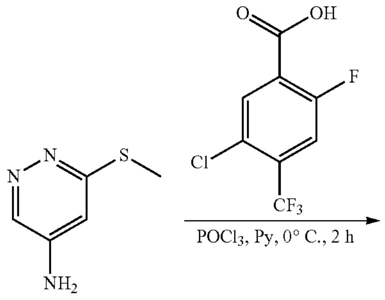

20B

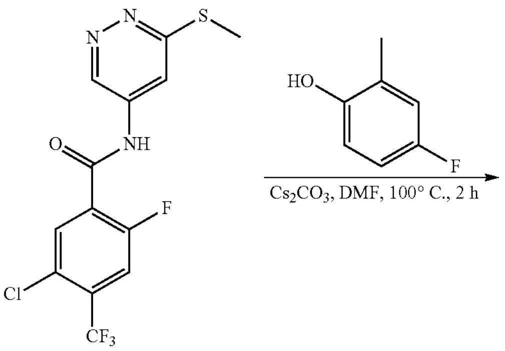

20C

-continued

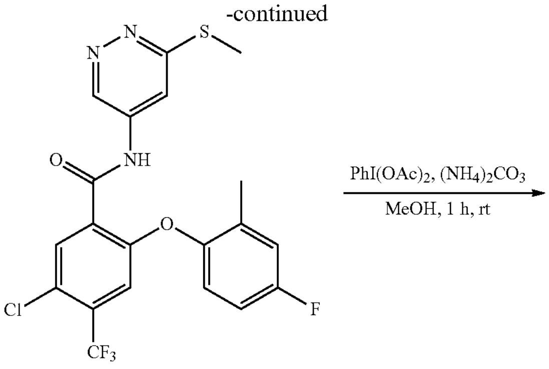

20D

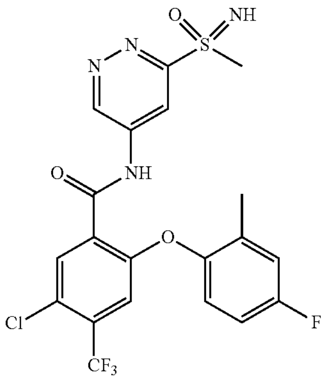

Compound 20

Step 1: 6-(methylthio)77yridazine-4-amine

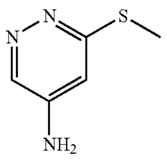

6-chloropyridazin-4-amine (1 g, 7.7 mmol) was dissolved in methanol (10 mL), and sodium thiomethoxide (2.8 g, 38.6 mmol) was added. The mixture was stirred and allowed to react at 100° C. for 16 hours in a sealed tube. The reaction was stopped. The reaction solution was spun dry, and the residue was adsorbed to silica gel and separated and purified by silica gel column chromatography (mobile phase: petroleum ether:ethyl acetate=1:10) to obtain the title compound (800 mg, white solid, yield: 73.4%).

MS (ESI): m/z 142.0 $[M+H]^+$;

Step 2: 5-chloro-2-fluoro-N-(6-(methylthio) 77 yridazine-4-yl)-4-(trifluoromethyl)benzamide

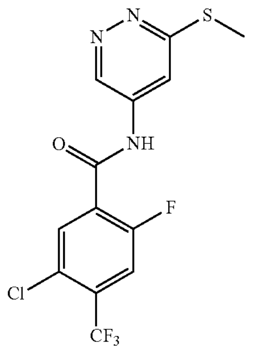 [SMILES: CSc1cc(NC(=O)c2cc(Cl)c(C(F)(F)F)cc2F)cnn1]

6-(methylthio)77yridazine-4-amine (75 mg, 0.53 mmol) was dissolved in pyridine (2 mL), 5-chloro-2-fluoro-4-(trifluoromethyl)benzoic acid (129 mg, 0.53 mmol) was added, and phosphorus oxychloride (244 mg, 1.59 mmol) was added dropwise at 0° C. Then the mixture was stirred and allowed to react for 2 hours. The reaction was stopped. The reaction solution was slowly added dropwise to ice-water (10 ml), and was adjusted to a pH of 5-6 using 1 N hydrochloric acid. The aqueous phase was extracted using ethyl acetate (15 ml×3). The organic phases were combined, washed with a saturated saline solution (5 ml×2), dried over anhydrous sodium sulfate, and filtered. The filtrate was spun dry in vacuo to obtain a crude product, and the crude product was separated and purified by silica gel column chromatography (mobile phase: petroleum ether:ethyl acetate=1:1) to obtain the title compound (90 mg, yield: 46.6%, yellow solid).

MS (ESI): m/z 365.0 $[M+H]^+$;

Step 3: 5-chloro-2-(4-fluoro-2-methylphenoxy)-N-(6-(methylthio) 78 yridazine-4-yl)-4-(trifluoromethyl)benzamide

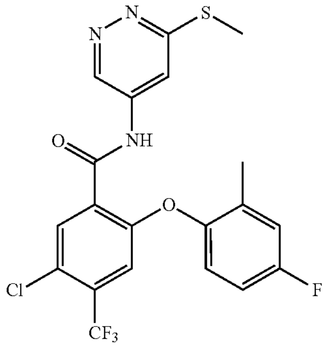

5-chloro-2-fluoro-N-(6-(methylthio) 78 yridazine-4-yl)-4-(trifluoromethyl)benzamide (80 mg, 0.22 mmol) was dissolved in DMF (1 mL), 4-fluoro-2-methylphenol (41.4 mg, 0.33 mmol) was added, and cesium carbonate (142.7 mg, 0.44 mmol) was added. The mixture was stirred and allowed to react in an oil bath at 100° C. for 2 hours. The reaction was stopped, and the reaction solution was quenched by adding water (10 ml). The aqueous phase was extracted using ethyl acetate (15 ml×3). The organic phases were combined, washed with a saturated saline solution (5 ml×2), dried over anhydrous sodium sulfate, and filtered. The filtrate was spun dry in vacuo to obtain a crude product. The crude product was separated and purified by silica gel column chromatography (mobile phase: petroleum ether:ethyl acetate=1:1) to obtain the title compound (69 mg, yield: 67.0%, white solid).

MS (ESI): m/z 472.0 $[M+H]^+$;

Step 4: 5-chloro-2-(4-fluoro-2-methylphenoxy)-N-(6-(S-methyliminosulfonyl)78yridazine-4-yl)-4-(trifluoromethyl)benzamide (Compound 20)

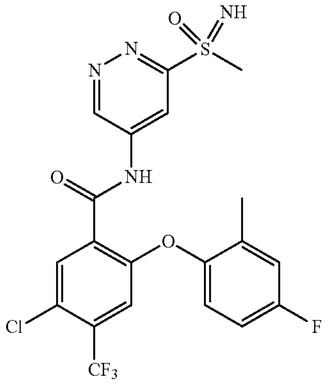

5-chloro-2-(4-fluoro-2-methylphenoxy)-N-(6-(methylthio) 79 yridazine-4-yl)-4-(trifluoromethyl)benzamide (60 mg, 0.13 mmol) was dissolved in methanol (1 mL), and ammonium carbonate (36.6 mg, 0.39 mmoL) and iodobenzene diacetate (164 mg, 0.51 mmoL) were added. The mixture was stirred at room temperature for 1 hour. The reaction was stopped. The reaction solution was spun dry, and the residue was adsorbed to silica gel and separated by silica gel column chromatography (mobile phase: petroleum ether:ethyl acetate=1:1) to obtain a crude product. The crude product was purified by reverse phase preparative chromatography (elution system: formic acid, water, and acetonitrile) to obtain the title compound (17.45 mg, yield: 27.3%, white solid).

MS (ESI): m/z 503.0 $[M+H]^+$;

$^1H$ NMR (400 MHz, DMSO-$d_6$) δ 11.66 (s, 1H), 9.39 (s, 1H), 8.63 (d, J=2.0 Hz, 1H), 8.21 (s, 1H), 8.14 (s, 1H), 7.24-7.17 (m, 1H), 7.11 (d, J=5.3 Hz, 3H), 4.86 (s, 1H), 3.31 (s, 3H), 2.16 (s, 3H).

Example 21

5-chloro-N-(6-(S-methyliminosulfonyl) 79 yridazine-4-yl)-2-(4-(trifluoromethoxy)phenoxy)-4-(trifluoromethyl)benzamide (Compound 21)

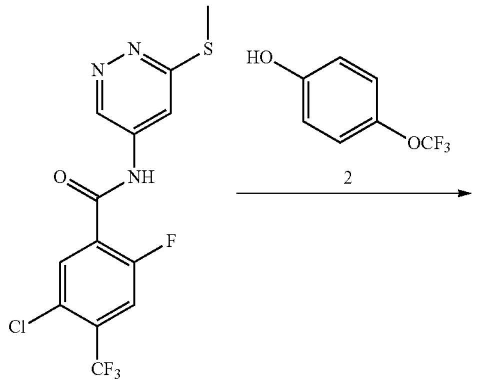
2

20C

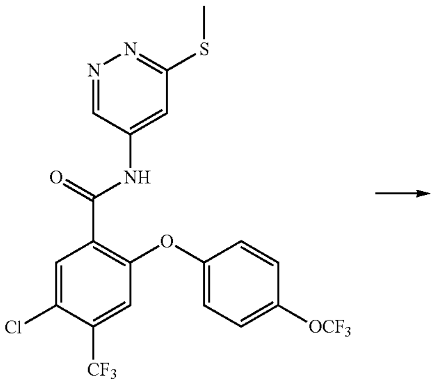

21A

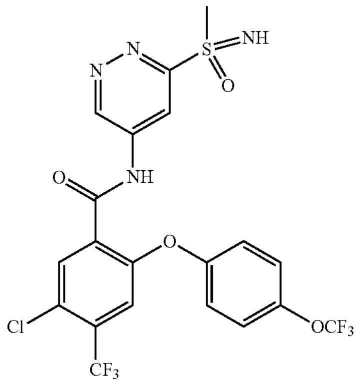

Compound 21

Step 1: 5-chloro-N-(6-(methylthio)79yridazine-4-yl)-2-(4-(trifluoromethoxy)phenoxy)-4-(trifluoromethyl)benzamide

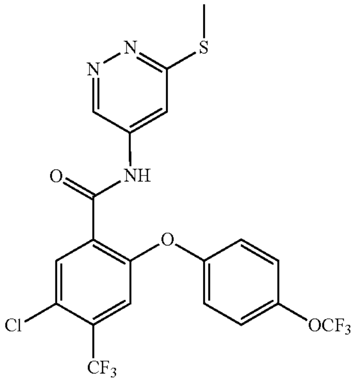

5-chloro-2-fluoro-N-(6-(methylthio) 80 yridazine-4-yl)-4-(trifluoromethyl)benzamide (70 mg, 0.192 mmol) and 4-(trifluoromethoxy)phenol (68.3 mg, 0.384 mmol) were dissolved in N,N-dimethylformamide (2 mL), and potassium carbonate (53 mg, 0.384 mmol) was added. The mixture was allowed to react in an oil bath at 70° C. for 16 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), dried over anhydrous sodium sulfate, and filtered. The filtrate was spun dry under reduced pressure, and the residue was separated and purified by column chromatography (silica gel, petroleum ether:ethyl acetate=1:1) to obtain the title compound (70 mg, yield: 69.72%, white solid).

MS (ESI): m/z 524.0 $[M+H]^+$;

Step 2: 5-chloro-N-(6-(S-methyliminosulfonyl) pyridazin-4-yl)-2-(4-(trifluoromethoxy)phenoxy)-4-(trifluoromethyl)benzamide (Compound 21)

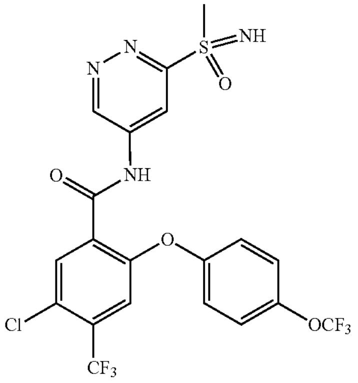

5-chloro-N-(6-(methylthio)pyridazin-4-yl)-2-(4-(trifluoromethoxy)phenoxy)-4-(trifluoromethyl)benzamide (60 mg, 0.125 mmol) was dissolved using methanol (2 mL), and ammonium carbonate (36.04 mg, 0.375 mmol) and iodobenzene diacetate (161 mg, 0.5 mmol) were added. The mixture was allowed to react at room temperature for 1 hour. The reaction was stopped, and the mixture was spun in vacuo to remove the solvent. After separation and purification by column chromatography (silica gel, petroleum ether: ethyl acetate=1:9) followed by preparation and purification by high performance liquid chromatography (elution system: ammonium bicarbonate, water, and acetonitrile), the title compound (25.42 mg, yield: 36.7%, yellow solid) was obtained.

MS (ESI): m/z 555.0 $[M+H]^+$;

$^1$H NMR (400 MHz, DMSO-$d_6$) δ 11.65 (s, 1H), 9.39 (d, J=2.4 Hz, 1H), 8.59 (d, J=2.4 Hz, 1H), 8.19 (s, 1H), 7.55 (s, 1H), 7.41 (d, J=8.8 Hz, 2H), 7.23 (d, J=9.1 Hz, 2H), 4.87 (s, 1H), 3.29 (s, 3H).

Example 22

5-chloro-2-(4,4-difluoroazepan-1-yl)-N-(6-(S-methyliminosulfonyl)pyridazin-4-yl)-4-(trifluoromethyl) benzamide (Compound 22)

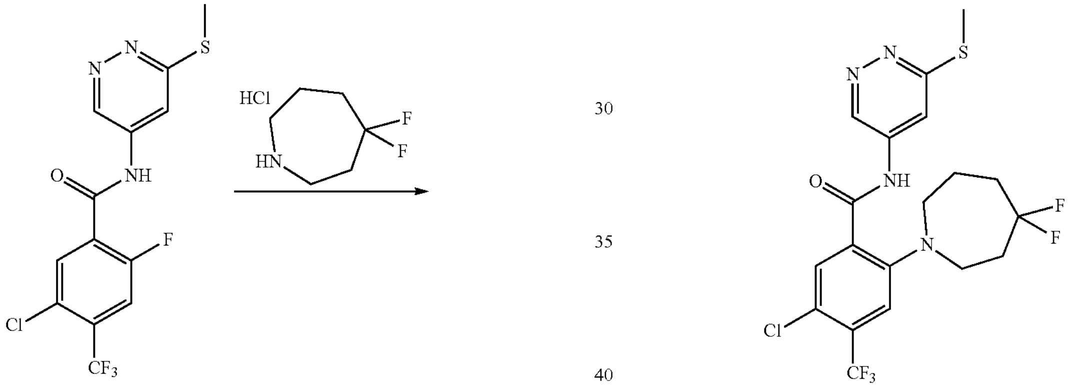

20C

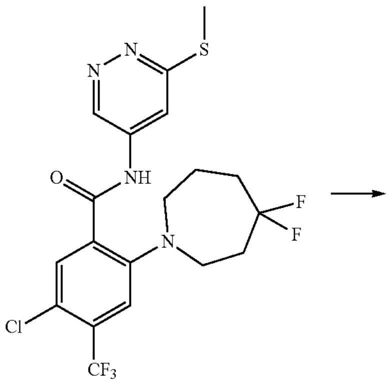

22A

-continued

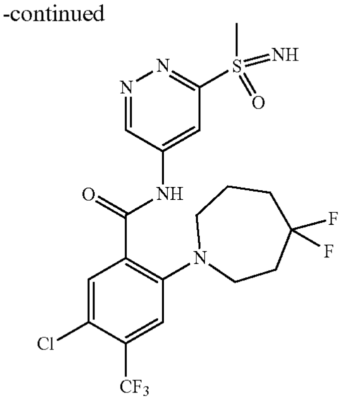

Compound 22

Step 1: 5-chloro-2-(4,4-difluoroazepan-1-yl)-N-(6-(methylthio)pyridazin-4-yl)-4-(trifluoromethyl)benzamide 5-chloro-2-fluoro-N-(6-(methylthio)pyridazin-4-yl)-4-(trifluoromethyl)benzamide (70 mg, 0.192 mmol) and 4,4-difluoroazepane hydrochloride (164 mg, 0.959 mmol) were dissolved in N,N-dimethylformamide (2 mL), and cesium carbonate (437 mg, 1.342 mmol) was added. The mixture was allowed to react in an oil bath at 100° C. for 16 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), dried over anhydrous sodium sulfate, and filtered. The filtrate was spun dry under reduced pressure, and the residue was separated and purified by column chromatography (silica gel, petroleum ether:ethyl acetate=1:1) to obtain the title compound (70 mg, yield: 75.95%, white solid).

MS (ESI): m/z 481.1 $[M+H]^+$;

Step 2: 5-chloro-2-(4,4-difluoroazepan-1-yl)-N-(6-(S-methyliminosulfonyl)pyridazin-4-yl)-4-(trifluoromethyl)benzamide (Compound 22)

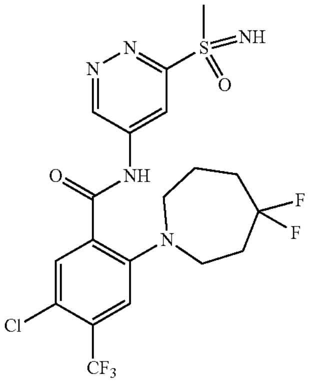 [SMILES: CS(=N)(=O)c1cc(NC(=O)c2cc(Cl)c(C(F)(F)F)cc2N2CCCC(F)(F)CC2)cnn1]

5-chloro-2-(4,4-difluoroazepan-1-yl)-N-(6-(methylthio)pyridazin-4-yl)-4-trifluoromethyl)benzamide (70 mg, 0.134 mmol) was dissolved in methanol (2 mL), and ammonium carbonate (39 mg, 0.402 mmol) and iodobenzene diacetate (172 mg, 0.535 mmol) were added. The mixture was allowed to react at room temperature for 1 hour. The reaction was stopped, and the mixture was spun in vacuo to remove the solvent. After separation and purification by column chromatography (silica gel, petroleum ether:ethyl acetate=1:10) followed by preparation and purification by high performance liquid chromatography (elution system: ammonium bicarbonate, water, and acetonitrile), the title compound (15.88 mg, yield: 23.2%, white solid) was obtained.

MS (ESI): m/z 512.0 $[M+H]^+$;

$^1H$ NMR (400 MHz, DMSO-$d_6$) δ 11.51 (s, 1H), 9.44 (s, 1H), 8.66 (s, 1H), 7.80 (s, 1H), 7.35 (s, 1H), 4.89 (s, 1H), 3.42-3.40 (m, 2H), 3.38-3.34 (m, 2H), 3.32 (s, 3H), 2.27 (brs, 2H), 2.08-2.00 (m, 2H), 1.80 (brs, 2H).

Example 23

5-chloro-2-(4-fluoro-2-methylphenoxy)-N-(4-fluoro-3-(S-methyliminosulfonyl)phenyl)-4-(trifluoromethyl)benzamide (Compound 23)

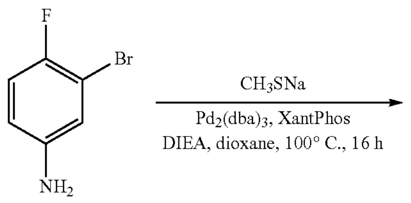

23A

-continued

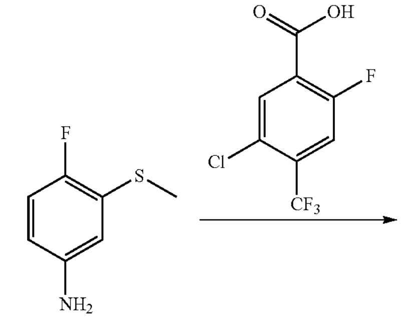

23B

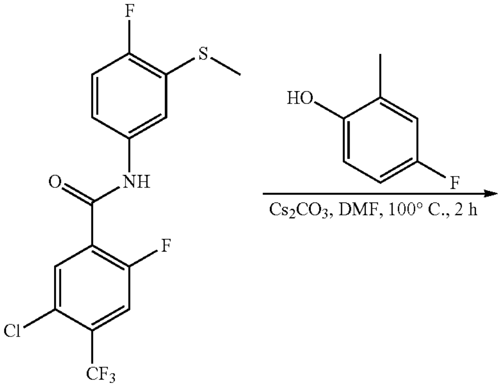

23C

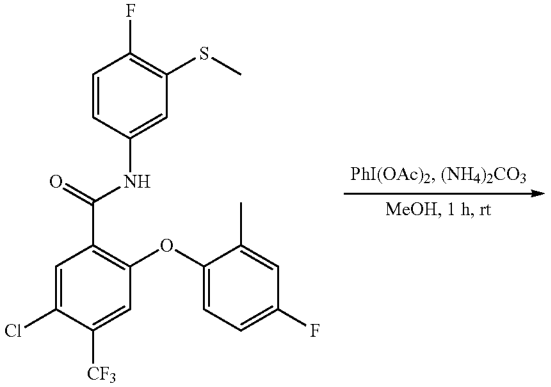

23D

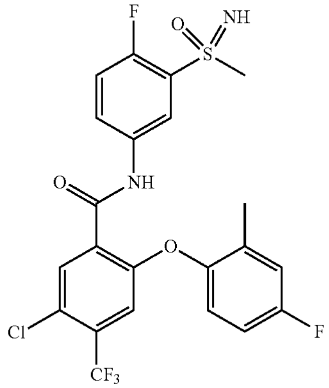

Compound 23

Step 1: 4-fluoro-3-(methylthio) aniline

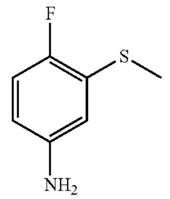

3-bromo-4-fluoroaniline (1 g, 5.26 mmol) was dissolved in ultra-dry 1,4-dioxane (20 mL), and sodium thiomethoxide (569 mg, 7.89 mmol), $Pd_2(dba)_3$ (485 mg, 0.53 mmol), XantPhos (609 mg, 1.05 mmol), and DIEA (2.04 g, 15.78 mmol) were added. Nitrogen replacement was performed, and the mixture was stirred and allowed to react in an oil bath at 110° C. for 16 hours. The reaction was stopped. The reaction solution was filtered, and the filter cake was rinsed using DCM (30 ml×3). The filtrate was spun dry, and the residue was adsorbed to silica gel and separated and purified by silica gel column chromatography (mobile phase: petroleum ether:ethyl acetate=1:2) to obtain the title compound (600 mg, colorless oily matter, yield: 72.6%).

MS (ESI): m/z 158.0 $[M+H]^+$;

Step 2: 5-chloro-2-fluoro-N-(4-fluoro-3-(methylthio)phenyl)-4-(trifluoromethyl)benzamide

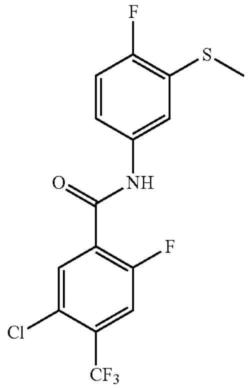 [SMILES: CSc1cc(NC(=O)c2cc(Cl)c(C(F)(F)F)cc2F)ccc1F]

5-chloro-2-fluoro-4-(trifluoromethyl)benzoic acid (980 mg, 4.04 mmol) was dissolved in thionyl chloride (1.5 mL). Nitrogen replacement was performed, and the mixture was stirred and allowed to react at 80° C. for 2 hours and spun dry for later use. 4-fluoro-3-(methylthio)aniline (635 mg, 4.04 mmol) was dissolved in ultra-dry DCM (10 mL), pyridine (1.28 g, 16.16 mmol) was added at 0° C., and then a solution of the foregoing spun dried matter for later use in dichloromethane (2 mL) was added. The mixture was stirred and allowed to react at room temperature for 2 h. The reaction was stopped. The reaction solution was spun dry, and the residue was adsorbed to silica gel and separated and purified by silica gel column chromatography (mobile phase: petroleum ether:ethyl acetate=10:1) to obtain the title compound (870 mg, yield: 56.4%, white solid).

MS (ESI): m/z 382.0 $[M+H]^+$;

Step 3: 5-chloro-2-(4-fluoro-2-methylphenoxy)-N-(4-fluoro-3-(methylthio)phenyl)-4-(trifluoromethyl)benzamide

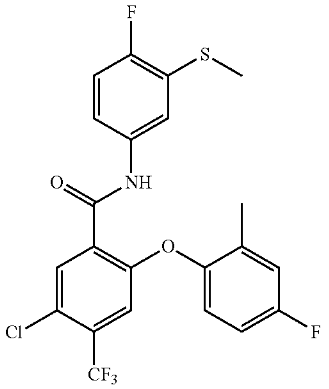 [SMILES: CSc1cc(NC(=O)c2cc(Cl)c(C(F)(F)F)cc2Oc2ccc(F)cc2C)ccc1F]

5-chloro-2-fluoro-N-(4-fluoro-3-(methylthio)phenyl)-4-(trifluoromethyl)benzamide (300 mg, 0.785 mmol) was dissolved in DMF (4 mL), 4-fluoro-2-methylphenol (198 mg, 1.571 mmol) was added, and cesium carbonate (512 mg, 1.571 mmol) was added. The mixture was stirred and allowed to react in an oil bath at 100° C. for 2 hours. The reaction was stopped. The reaction solution was quenched by adding water (20 ml). The aqueous phase was extracted using ethyl acetate (20 ml×3). The organic phases were combined, washed with a saturated saline solution (5 ml×2), dried over anhydrous sodium sulfate, and filtered. The filtrate was spun dry in vacuo to obtain a crude product. The crude product was separated and purified by silica gel column chromatography (mobile phase: petroleum ether: ethyl acetate=5:1) to obtain the title compound (290 mg, yield: 75.7%, yellow solid).

MS (ESI): m/z 488.1 $[M+H]^+$;

Step 4: 5-chloro-2-(4-fluoro-2-methylphenoxy)-N-(4-fluoro-3-(S-methyliminosulfonyl)phenyl)-4-(trifluoromethyl)benzamide (Compound 23)

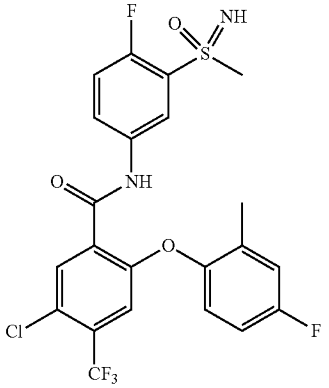 [SMILES: Cc1cc(F)ccc1Oc1cc(C(F)(F)F)c(Cl)cc1C(=O)Nc1ccc(F)c(S(C)(=N)=O)c1]

5-chloro-2-(4-fluoro-2-methylphenoxy)-N-(4-fluoro-3-(methylthio)phenyl)-4-(trifluoromethyl)benzamide (290 mg, 0.59 mmol) was dissolved in methanol (3 mL), and ammonium carbonate (171.3 mg, 1.78 mmoL) and iodobenzene diacetate (766 mg, 2.36 mmoL) were added. The mixture was stirred and allowed to react at room temperature for 1 hour. The reaction was stopped. The reaction solution was spun dry, and the residue was adsorbed to silica gel and separated by silica gel column chromatography (mobile phase: petroleum ether:ethyl acetate=1:10) to obtain a crude product. The crude product was purified by reverse phase preparative chromatography (elution system: ammonium bicarbonate, water, and acetonitrile) to obtain the title compound (197 mg, yield: 64.3%, white solid).

MS (ESI): m/z 519.1 $[M+H]^+$;

$^1H$ NMR (400 MHz, DMSO-$d_6$) δ 10.92 (s, 1H), 8.25 (dd, J=6.5, 2.7 Hz, 1H), 8.06 (s, 1H), 7.92-7.85 (m, 1H), 7.43 (t, J=9.3 Hz, 1H), 7.25-7.19 (m, 1H), 7.13-7.06 (m, 3H), 4.68 (s, 1H), 3.18 (s, 3H), 2.17 (s, 3H).

Resolution of Chiral Isomers of Compound 23:

(S)-5-chloro-2-(4-fluoro-2-methylphenoxy)-N-(4-fluoro-3-(S-methyliminosulfonyl)phenyl)-4-(trifluoromethyl)benzamide (R)-5-chloro-2-(4-fluoro-2-methylphenoxy)-N-(4-fluoro-3-(S-methyliminosulfonyl)phenyl)-4-(trifluoromethyl)benzamide

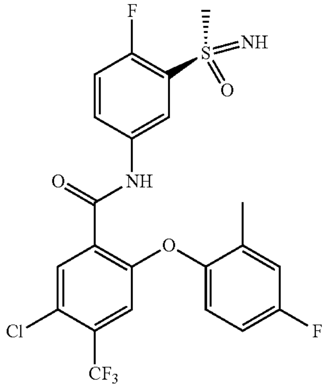

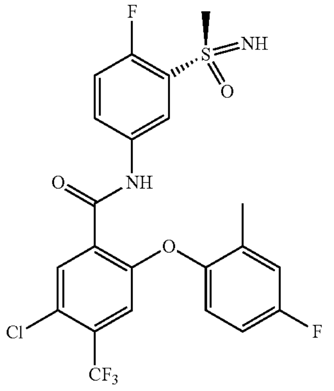

Compound 23 was separated by a chiral preparative separation column (chromatography column: DAICEL CHIRALCEL® AS, 250*25 mm, 10 μm; mobile phase: A—Supercritical $CO_2$; B—MEOH (+0.1% 7.0 mol/1 Ammonia in MEOH), 30% B proportional elution, flow-rate: 70 mL/min, column temperature: room temperature) to obtain single-configuration compound 23E1 (having a shorter retention time) and compound 23E2 (having a longer retention time).

Example 24

5-chloro-2-(4-fluoro-2-(methoxy-$d_3$)phenoxy)-N-(4-fluoro-3-(S-methyliminosulfonyl)phenyl)-4-(trifluoromethyl)benzamide (Compound 24)

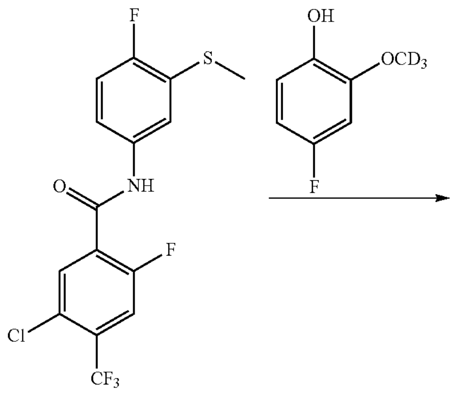

23C

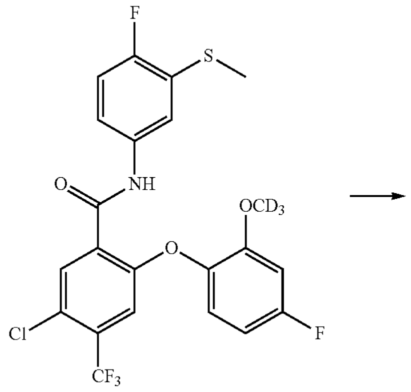

24A

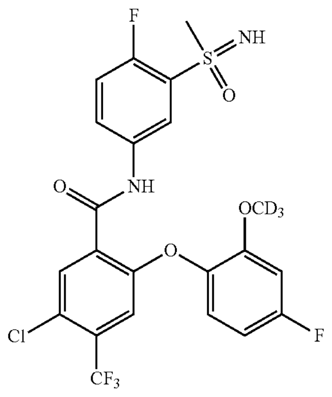

Compound 24

Step 1: 5-chloro-2-(4-fluoro-2-(methoxy-d3)phenoxy)-N-(4-fluoro-3-(methylthio)phenyl)-4-(trifluoromethyl)benzamide

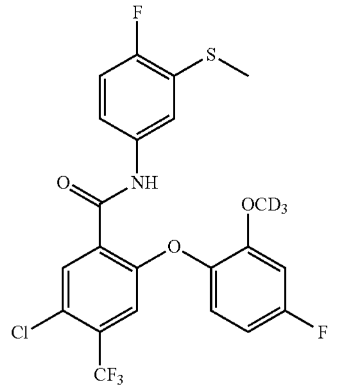

4-fluoro-2-(methoxy-$d_3$)phenol (95 mg, 0.654 mmol) and 5-chloro-2-fluoro-N-(4-fluoro-3-(methylthio)phenyl)-4-(trifluoromethyl)benzamide (50 mg, 0.131 mmol) were dissolved in N,N-dimethylformamide (1 mL), and potassium carbonate (36.2 mg, 0.262 mmol) was added. The mixture was sealed and then allowed to react in an oil bath at 100° C. for 2 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3) and dried over anhydrous sodium sulfate. After separation and purification by column chromatography (silica gel, petroleum ether:ethyl acetate=10:1), the title compound (80 mg, yield: 98.2%, white solid) was obtained.

MS (ESI): m/z 507.1 $[M+H]^+$;

Step 2: 5-chloro-2-(4-fluoro-2-(methoxy-$d_3$)phenoxy)-N-(4-fluoro-3-(S-methyliminosulfonyl)phenyl)-4-(trifluoromethyl)benzamide (Compound 24)

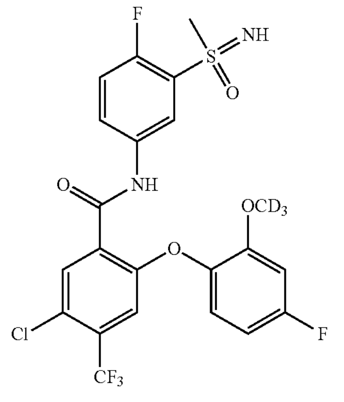

5-chloro-2-(4-fluoro-2-(methoxy-$d_3$)phenoxy)-N-(4-fluoro-3-(methylthio)phenyl)-4-(trifluoromethyl)benzamide (70 mg, 0.138 mmol) was dissolved in methanol (2 mL), and ammonium carbonate (40 mg, 0.415 mmol) and iodobenzene diacetate (178 mg, 0.553 mmol) were added. The mixture was allowed to react at room temperature for 1 hour.

The reaction was stopped, and the mixture was spun in vacuo to remove the solvent. After separation and purification by column chromatography (silica gel, petroleum ether: ethyl acetate=1:1) followed by preparation and purification by high performance liquid chromatography (elution system: formic acid, water, and acetonitrile), the title compound (39.21 mg, yield: 52.7%, white solid) was obtained.

MS (ESI): m/z 538.0 $[M+H]^+$;

$^1H$ NMR (400 MHz, DMSO-$d_6$) δ 10.88 (s, 1H), 8.28 (dd, J=6.4, 2.6 Hz, 1H), 8.01 (s, 1H), 7.96-7.90 (m, 1H), 7.44 (t, J=9.3 Hz, 1H), 7.28 (dd, J=8.8, 5.9 Hz, 1H), 7.14 (dd, J=10.6, 2.8 Hz, 1H), 6.98 (s, 1H), 6.85 (td, J=8.5, 2.9 Hz, 1H), 4.69 (s, 1H), 3.18 (s, 3H).

Example 25

5-chloro-N-(4-fluoro-3-(S-methyliminosulfonyl)phenyl)-2-(2-(methoxy-$d_3$)-4-(trifluoromethoxy)phenoxy)-4-(trifluoromethyl)benzamide (Compound 25)

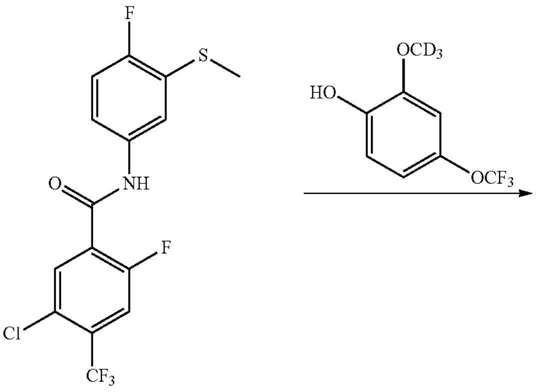

23C

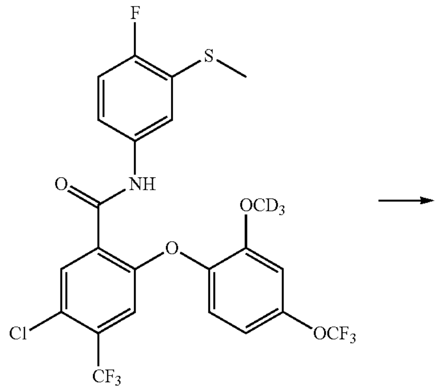

25A

-continued

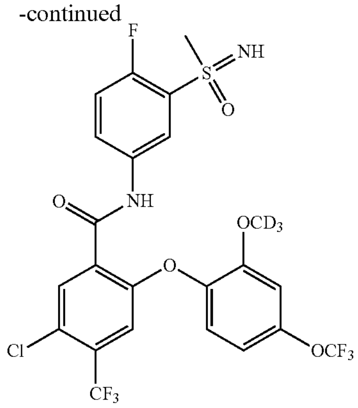

Compound 25

Step 1: 5-chloro-N-(4-fluoro-3-(methylthio)phenyl)-2-(2-(methoxy-$d_3$)-4-(trifluoromethoxy)phenoxy)-4-(trifluoromethyl)benzamide

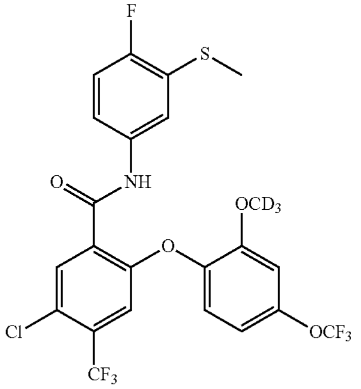

5-chloro-2-fluoro-N-(4-fluoro-3-(methylthio)phenyl)-4-(trifluoromethyl)benzamide (60 mg, 0.157 mmol) and 2-(methoxy-$d_3$)-4-(trifluoromethoxy)phenol (66.4 mg, 0.314 mmol) were dissolved in N,N-dimethylformamide (1.5 mL), and potassium carbonate (43.4 mg, 0.314 mmol) was added. The mixture was allowed to react in an oil bath at 100° C. for 2 hours. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), and dried over anhydrous sodium sulfate. After separation and purification by column chromatography (silica gel, petroleum ether:ethyl acetate=10:1), the title compound (80 mg, yield: 89.79%, white solid) was obtained.

MS (ESI): m/z 572.8 $[M+H]^+$;

Step 2: 5-chloro-N-(4-fluoro-3-(S-methyliminosulfonyl)phenyl)-2-(2-(methoxy-$d_3$)-4-(trifluoromethoxy)phenoxy)-4-(trifluoromethyl)benzamide (Compound 25)

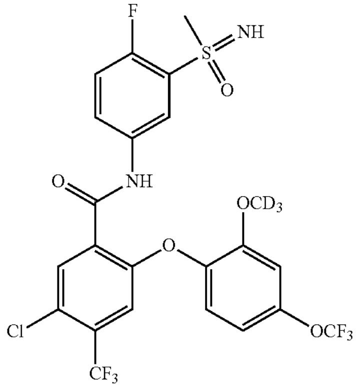

5-chloro-N-(4-fluoro-3-(methylthio)phenyl)-2-(2-(methoxy-$d_3$)-4-(trifluoromethoxy)phenoxy)-4-(trifluoromethyl)benzamide (60 mg, 0.105 mmol) was dissolved using methanol (2 mL), and ammonium carbonate (30.3 mg, 0.315 mmol) and iodobenzene diacetate (135.15 mg, 0.42 mmol) were added. The mixture was allowed to react at room temperature for 1 hour. The reaction was stopped, and the mixture was spun in vacuo to remove the solvent. After separation and purification by column chromatography (silica gel, petroleum ether:ethyl acetate=1:1) followed by preparation and purification by high performance liquid chromatography (elution system: formic acid, water, and acetonitrile), the title compound (16.02 mg, yield: 25.4%, white solid) was obtained.

MS (ESI): m/z 604.1 $[M+H]^+$;

$^1$H NMR (400 MHz, DMSO-$d_6$) δ 10.89 (s, 1H), 8.25 (dd, J=6.4, 2.6 Hz, 1H), 8.03 (s, 1H), 7.91 (dd, J=8.3, 3.6 Hz, 1H), 7.43 (t, J=9.3 Hz, 1H), 7.28 (d, J=8.8 Hz, 1H), 7.20 (d, J=2.4 Hz, 1H), 7.13 (s, 1H), 7.00 (d, J=8.7 Hz, 1H), 4.68 (s, 1H), 3.18 (s, 3H).

Example 26

5-chloro-N-(4-fluoro-3-(S-methyliminosulfonyl)phenyl)-2-(4-(trifluoromethoxy)phenoxy)-4-(trifluoromethyl)benzamide (Compound 26)

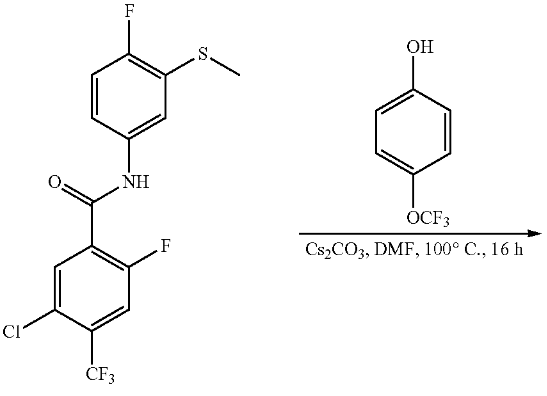

23C

-continued

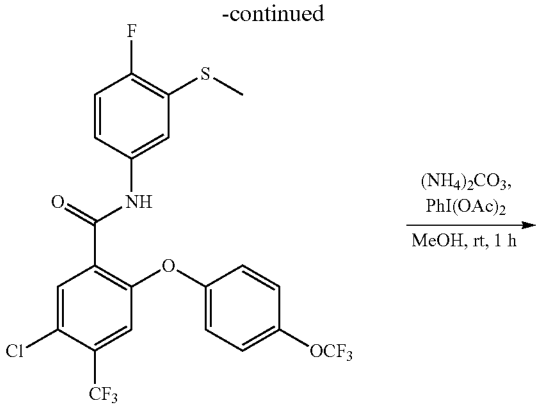

26A

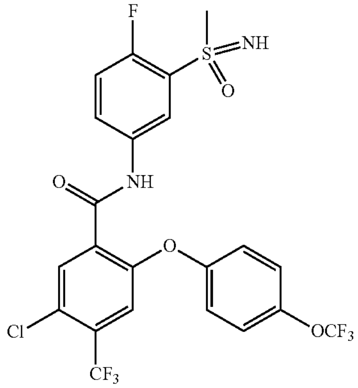

Compound 26

Step 1: 5-chloro-N-(4-fluoro-3-(methylthio)phenyl)-2-(4-(trifluoromethoxy)phenoxy)-4-(trifluoromethyl)benzamide

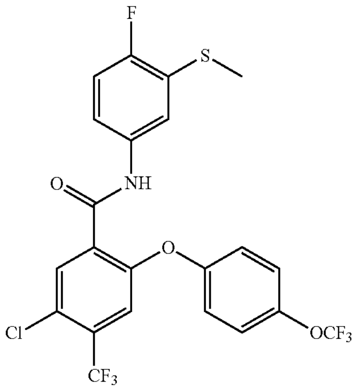 [SMILES: CSc1cc(NC(=O)c2cc(Cl)c(C(F)(F)F)cc2Oc2ccc(OC(F)(F)F)cc2)ccc1F]

5-chloro-2-fluoro-N-(4-fluoro-3-(methylthio)phenyl)-4-(trifluoromethyl)benzamide (100 mg, 0.26 mmol) was dissolved in DMF (2 mL), 4-(trifluoromethoxy)phenol (93.3 mg, 0.52 mmol) was added, and cesium carbonate (170 mg, 0.52 mmol) was added. The mixture was stirred in an oil bath at 100° C. for 2 hours. The reaction was stopped, and the reaction solution was quenched by adding water (10 ml). The aqueous phase was extracted using ethyl acetate (15 ml×3). The organic phases were combined, washed with a saturated saline solution (5 ml×2), dried over anhydrous sodium sulfate, and filtered. The filtrate was spun dry to obtain a crude product. The crude product was separated and purified by silica gel column chromatography (mobile phase: petroleum ether:ethyl acetate=10:1) to obtain the title compound (100 mg, yield: 71.4%, white solid).

MS (ESI): m/z 540.0 $[M+H]^+$;

Step 2: 5-chloro-N-(4-fluoro-3-(S-methyliminosulfonyl)phenyl)-2-(4-(trifluoromethoxy)phenoxy)-4-(trifluoromethyl)benzamide (Compound 26)

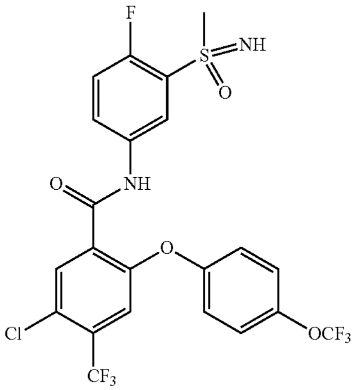 [SMILES: CS(=N)(=O)c1cc(NC(=O)c2cc(Cl)c(C(F)(F)F)cc2Oc2ccc(OC(F)(F)F)cc2)ccc1F]

5-chloro-N-(4-fluoro-3-(methylthio)phenyl)-2-(4-(trifluoromethoxy)phenoxy)-4-(trifluoromethyl)benzamide (87 mg, 0.16 mmol) was dissolved in methanol (1 mL), and ammonium carbonate (46.4 mg, 0.48 mmoL) and iodobenzene diacetate (206 mg, 0.64 mmoL) were added. The mixture was stirred at room temperature for 0.5 hours. The reaction was stopped. The reaction solution was spun dry, and the residue was adsorbed to silica gel and separated by silica gel column chromatography (mobile phase: petroleum ether:ethyl acetate=1:1) to obtain a crude product. The crude product was purified by reverse phase preparative chromatography (elution system: ammonium bicarbonate, water, and acetonitrile) to obtain the title compound (28.96 mg, yield: 31.5%, white solid).

MS (ESI): m/z 571.0 $[M+H]^+$;

$^1H$ NMR (400 MHz, DMSO-$d_6$) δ 10.86 (s, 1H), 7.86 (s, 1H), 7.71 (d, J=23.3 Hz, 2H), 7.48 (d, J=8.0 Hz, 3H), 7.34 (s, 2H), 7.02 (s, 1H), 4.75 (s, 1H), 3.13 (s, 3H).

Example 27

5-chloro-2-(4,4-difluoroazepan-1-yl)-N-(4-fluoro-3-(S-methyliminosulfonyl)phenyl)-4-(trifluoromethyl)benzamide (Compound 27)

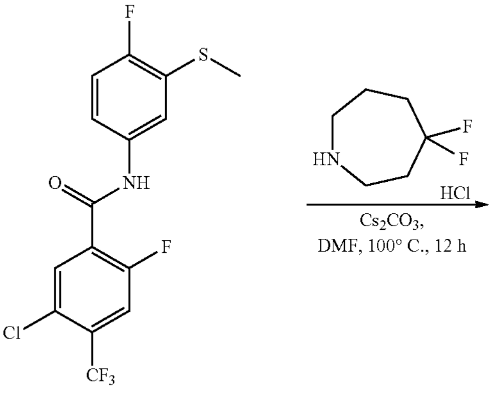

23C

-continued

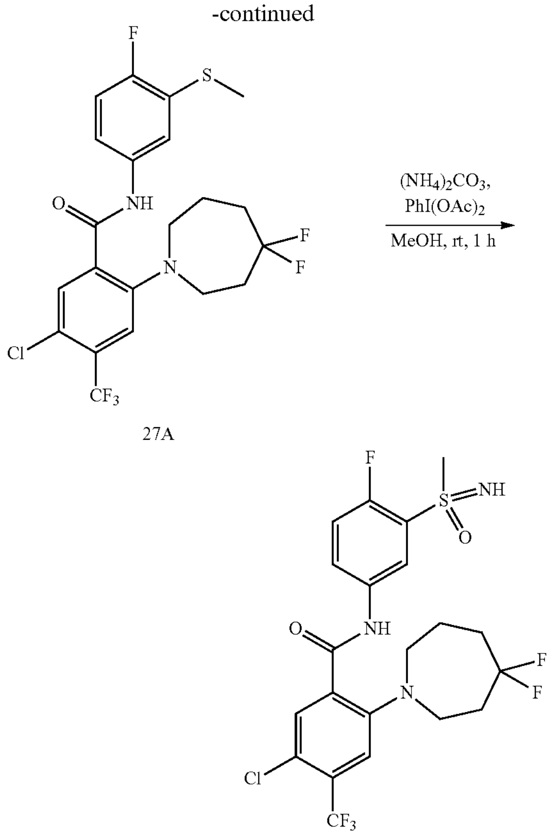

27A

Compound 27

Step 1: 5-chloro-2-(4,4-difluoroazepan-1-yl)-N-(4-fluoro-3-(methylthio)phenyl)-4-(trifluoromethyl) benzamide

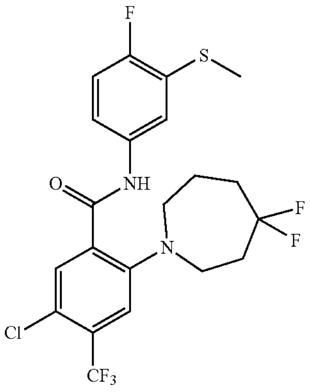 [SMILES: CSc1cc(NC(=O)c2cc(Cl)c(C(F)(F)F)cc2N2CCCC(F)(F)CC2)ccc1F]

4,4-difluoroazepane hydrochloride (80 mg, 0.58 mmol) was dissolved in DMF (2 mL), and 5-chloro-2-fluoro-N-(4-fluoro-3-(methylthio)phenyl)-4-(trifluoromethyl)benzamide (80 mg, 0.20 mmol) and cesium carbonate (210 mg, 0.64 mmol) were added. The mixture was stirred in an oil bath at 100° C. for 12 hours. The reaction was stopped, and the reaction solution was quenched by adding water (5 mL). The aqueous phase was extracted using ethyl acetate (10 mL×3). The organic phases were combined, washed with a saturated saline solution (5 mL×2), dried over anhydrous sodium sulfate, and spun dry in vacuo to obtain a crude product. The crude product was separated and purified by silica gel column chromatography (mobile phase: petroleum ether: ethyl acetate=3:1) to obtain the title compound (45 mg, yield: 43.2%, yellow solid).

MS (ESI): m/z 497.1 $[M+H]^+$;

Step 2: 5-chloro-2-(4,4-difluoroazepan-1-yl)-N-(4-fluoro-3-(S-methylsulfamoyl)phenyl)-4-trifluoromethylbenzamide (Compound 27)

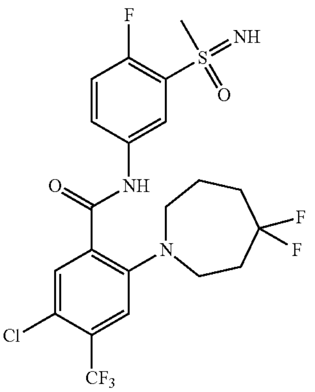 [SMILES: CS(=N)(=O)c1cc(NC(=O)c2cc(Cl)c(C(F)(F)F)cc2N2CCCC(F)(F)CC2)ccc1F]

5-chloro-2-(4,4-difluoroazepan-1-yl)-N-(4-fluoro-3-(methylthio)phenyl)-4-(trifluoromethyl)benzamide (45 mg, 0.09 mmol) was dissolved in methanol (1.5 mL), and ammonium bicarbonate (27 mg, 0.28 mmol) and iodobenzene diacetate (118 mg, 0.36 mmol) were added. The mixture was stirred and allowed to react at room temperature for 1 hour. The reaction was stopped. The reaction solution was spun dry, and was quenched by adding water (2 ml). The aqueous phase was extracted using ethyl acetate (5 ml×3). The organic phases were combined, washed with a saturated saline solution (3 ml×2), dried over anhydrous sodium sulfate, and spun dry in vacuo to obtain a crude product. The crude product was purified by reverse phase preparative chromatography (elution system: ammonium bicarbonate, water, and acetonitrile) to obtain the title compound (2.85 mg, yield: 0.59%, white solid).

MS (ESI): m/z 539.0 $[M+H]^+$;

$^1H$ NMR (400 MHz, DMSO-$d_6$) δ 10.87 (s, 1H), 8.27 (dd, J=6.4, 2.5 Hz, 1H), 8.01-7.90 (m, 1H), 7.69 (s, 1H), 7.46 (t, J=9.3 Hz, 1H), 7.34 (s, 1H), 4.70 (s, 1H), 3.40 (brs, 4H), 3.20 (s, 3H), 2.25 (brs, 2H), 2.07 (brs, 2H), 1.81 (brs, 2H).

Resolution of Chiral Isomers of Compound 27:

(S)-5-chloro-2-(4,4-difluoroazepan-1-yl)-N-(4-fluoro-3-(S-methylsulfamoyl)phenyl)-4-trifluoromethylbenzamide (R)-5-chloro-2-(4,4-difluoroazepan-1-yl)-N-(4-fluoro-3-(S-methylsulfamoyl)phenyl)-4-trifluoromethylbenzamide

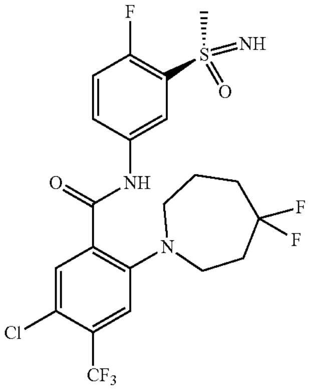

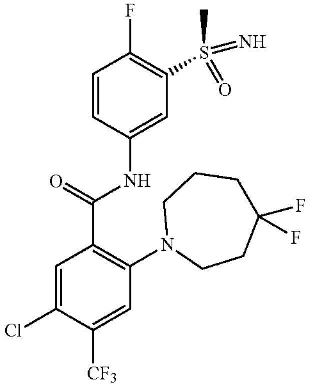

Compound 27 was separated by a chiral preparative separation column (chromatography column: DAICEL CHIRALCEL® AS, 250*25 mm, 10 μm; mobile phase: A—Supercritical $CO_2$; B—MEOH (+0.1% 7.0 mol/1 Ammonia in MEOH), 45% B proportional elution, flow-rate: 70 mL/min, column temperature: room temperature) to obtain single-configuration compound 27E1 (having a shorter retention time) and compound 27E2 (having a longer retention time).

Example 28

5-chloro-2-((3aR,6aS)-5,5-difluorohexahydrocyclopentadieno[c]pyrrol-2(1H)-yl)-N-(4-fluoro-3-(S-methyliminosulphonyl)phenyl)-4-(trifluoromethyl) benzamide (Compound 28)

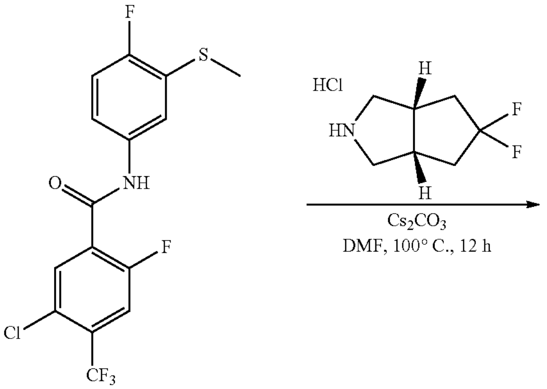

23C

-continued

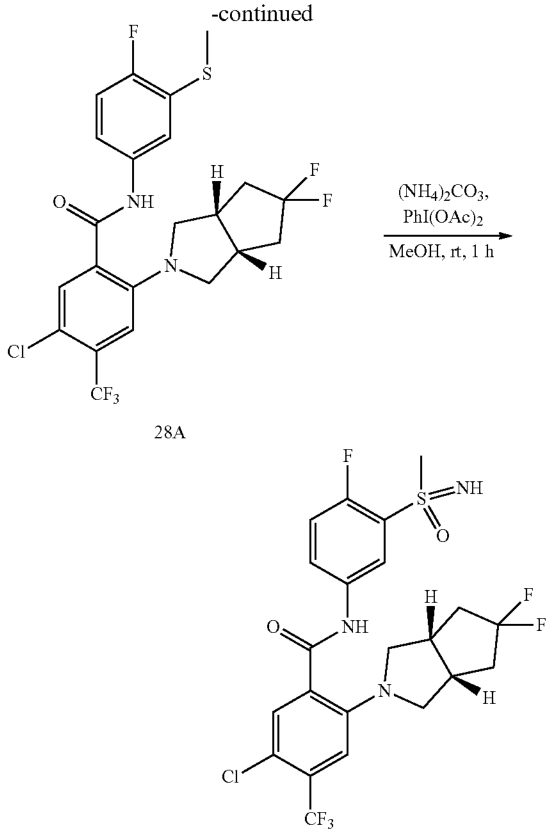

28A

Compound 28

Step 1: 5-chloro-2-((3aR,6aS)-5,5-difluorohexahydrocyclopentadieno[c]pyrrol-2(1H)-yl)-N-(4-fluoro-3-(methylthio)phenyl)-4-(trifluoromethyl)benzamide

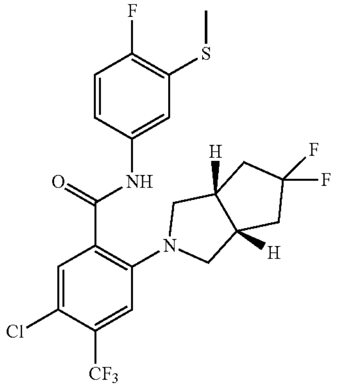 [SMILES: CSc1cc(NC(=O)c2cc(Cl)c(C(F)(F)F)cc2N2C[C@@H]3CC(F)(F)C[C@@H]3C2)ccc1F]

(3aR,6aS)-5,5-difluorohexahydrocyclopentadieno[c]pyrrole hydrochloride (100 mg, 0.681 mmol) was dissolved in DMF (1 mL), and 5-chloro-2-fluoro-N-(4-fluoro-3-(methylthio)phenyl)-4-(trifluoromethyl)benzamide (130 mg, 0.340 mmol) and cesium carbonate (322 mg, 1.021 mmol) were added. Nitrogen replacement was performed, and the mixture was stirred and allowed to react in an oil bath at 100° C. for 16 hours. The reaction was stopped. The reaction solution was quenched by adding water (5 mL). The aqueous phase was extracted using ethyl acetate (10 mL×3). The organic phases were combined, washed with a saturated saline solution (5 mL×2), dried over anhydrous sodium sulfate, and filtered. The filtrate was spun dry in vacuo to obtain a crude product, and the crude product was separated and purified by silica gel column chromatography (mobile phase: petroleum ether:ethyl acetate=2:1) to obtain the title compound (100 mg, yield: 57.8%, yellow solid).

MS (ESI): m/z 510.1 $[M+H]^+$;

Step 2: 5-chloro-2-((3aR,6aS)-5,5-difluorohexahydrocyclopentadieno[c]pyrrol-2(1H)-yl)-N-(4-fluoro-3-(S-methyliminosulphonyl)phenyl)-4-(trifluoromethyl)benzamide (Compound 28)

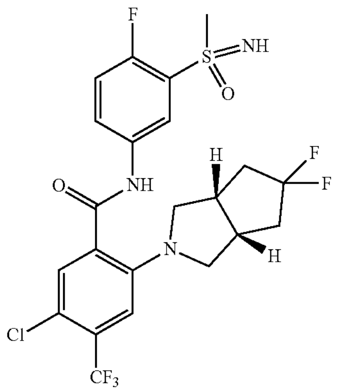 [SMILES: CS(=N)(=O)c1cc(NC(=O)c2cc(Cl)c(C(F)(F)F)cc2N2C[C@@H]3CC(F)(F)C[C@@H]3C2)ccc1F]

5-chloro-2-((3aR,6aS)-5,5-difluorohexahydrocyclopentadieno[c]pyrrol-2(1H)-yl)-N-(4-fluoro-3-(methylthio)phenyl)-4-(trifluoromethyl)benzamide (100 mg, 0.196 mmol) was dissolved in methanol (1.5 mL), and ammonium carbonate (56.6 mg, 0.589 mmol) and iodobenzene oxalate (253.1 mg, 0.785 mmol) were added. The mixture was stirred and allowed to react at room temperature for 1 hour. The reaction was stopped. The reaction solution was spun dry, and was quenched by adding saturated sodium bicarbonate solution water (2 ml). The aqueous phase was extracted using ethyl acetate (5 ml×3). The organic phases were combined, washed with a saturated saline solution (3 ml×2), dried over anhydrous sodium sulfate, and filtered. The filtrate was spun dry in vacuo to obtain a crude product, and the crude product was purified by reverse phase preparative chromatography (elution system: ammonia water, water, and acetonitrile) to obtain the title compound (10 mg, yield: 9.4%, white solid).

MS (ESI): m/z 539.8 $[M+H]^+$;

$^1H$ NMR (400 MHz, DMSO-$d_6$) δ 10.88 (s, 1H), 8.29 (d, J=3.8 Hz, 1H), 8.01-7.85 (m, 1H), 7.65 (s, 1H), 7.45 (t, J=9.3 Hz, 1H), 7.14 (s, 1H), 4.68 (s, 1H), 3.39 (d, J=7.0 Hz, 2H), 3.23-3.19 (m, 5H), 2.84 (brs, 2H), 2.39-2.25 (m, 2H), 1.96 (brs, 2H).

Example 29

5-chloro-2-((4,4-difluorocyclohexyl)oxy)-N-(4-fluoro-3-(S-methyliminosulfonyl)phenyl)-4-(trifluoromethyl)benzamide (Compound 29)

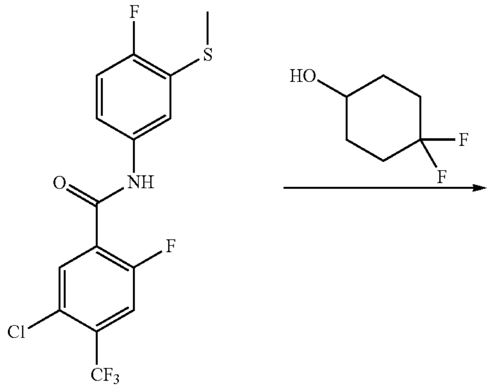

23C

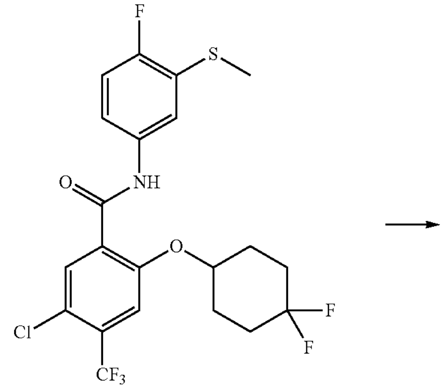

29A

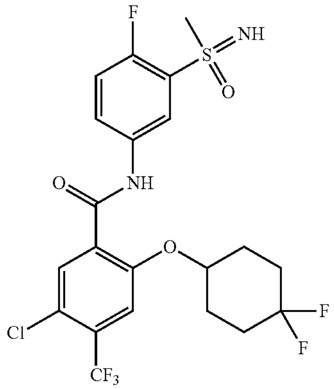

Compound 29

Step 1: 5-chloro-2-((4,4-difluorocyclohexyl)oxy)-N-(4-fluoro-3-(methylthio)phenyl)-4-(trifluoromethyl)benzamide

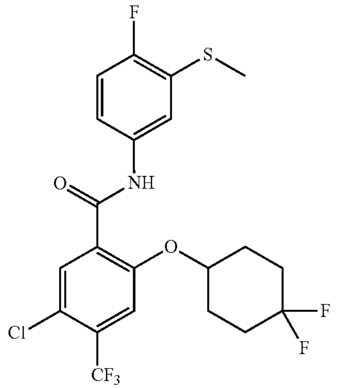 [SMILES: CSc1cc(NC(=O)c2cc(Cl)c(C(F)(F)F)cc2OC2CCC(F)(F)CC2)ccc1F]

5-chloro-2-fluoro-N-(4-fluoro-3-(methylthio)phenyl)-4-(trifluoromethyl)benzamide (80 mg, 0.21 mmol) and 4,4-difluorocyclohexan-1-ol (114 mg, 0.84 mmol) were dissolved in N,N-dimethylformamide (2 mL), and cesium carbonate (205 mg, 0.63 mmol) was added. The mixture was allowed to react in an oil bath at 100° C. for 1 hour. The reaction was stopped. The reaction solution was quenched by adding a saturated ammonium chloride solution (5 mL), and was extracted using ethyl acetate (20 mL×3). The combined organic phase was washed with a saturated saline solution (20 mL×3), dried over anhydrous sodium sulfate, and filtered. The filtrate was spun dry under reduced pressure, and the residue was separated and purified by column chromatography (silica gel, petroleum ether:ethyl acetate=10:1) to obtain the title compound (120 mg, yield: 92.3%, white solid).

MS (ESI): m/z 498.1 $[M+H]^+$;

Step 2: 5-chloro-2-((4,4-difluorocyclohexyl)oxy)-N-(4-fluoro-3-(S-methyliminosulfonyl)phenyl)-4-(trifluoromethyl)benzamide (Compound 29)

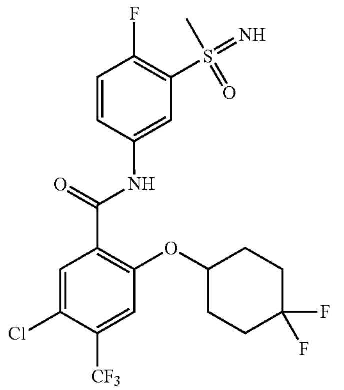 [SMILES: CS(=N)(=O)c1cc(NC(=O)c2cc(Cl)c(C(F)(F)F)cc2OC2CCC(F)(F)CC2)ccc1F]

5-chloro-2-((4,4-difluorocyclohexyl)oxy)-N-(4-fluoro-3-(methylthio)phenyl)-4-(trifluoromethyl)benzamide (105 mg, 0.211 mmol) was dissolved using methanol (2 mL), and ammonium carbonate (61 mg, 0.634 mmol) and iodobenzene diacetate (272.2 mg, 0.845 mmol) were added. The mixture was allowed to react at room temperature for 1 hour. The reaction was stopped, and the mixture was spun in vacuo to remove the solvent. After separation and purification by column chromatography (silica gel, petroleum ether: ethyl acetate=1:1) followed by preparation and purification by high performance liquid chromatography (elution system: formic acid, water, and acetonitrile), the title compound (71.14 mg, yield: 64.1%, white solid) was obtained.

MS (ESI): m/z 529.1 $[M+H]^+$;

$^1H$ NMR (400 MHz, DMSO-$d_6$) δ 10.72 (s, 1H), 8.27 (s, 1H), 7.86 (s, 2H), 7.64 (s, 1H), 7.44 (t, J=9.1 Hz, 1H), 4.94 (brs, 1H), 4.68 (s, 1H), 3.18 (s, 3H), 1.88 (brs, 8H).

Example 30

5-chloro-2-(4-fluoro-2-methylphenoxy)-N-(2-(1-(S-methyliminosulfonyl)cyclopropyl)96yridine-4-yl)-4-(trifluoromethyl)benzamide (Compound 30)

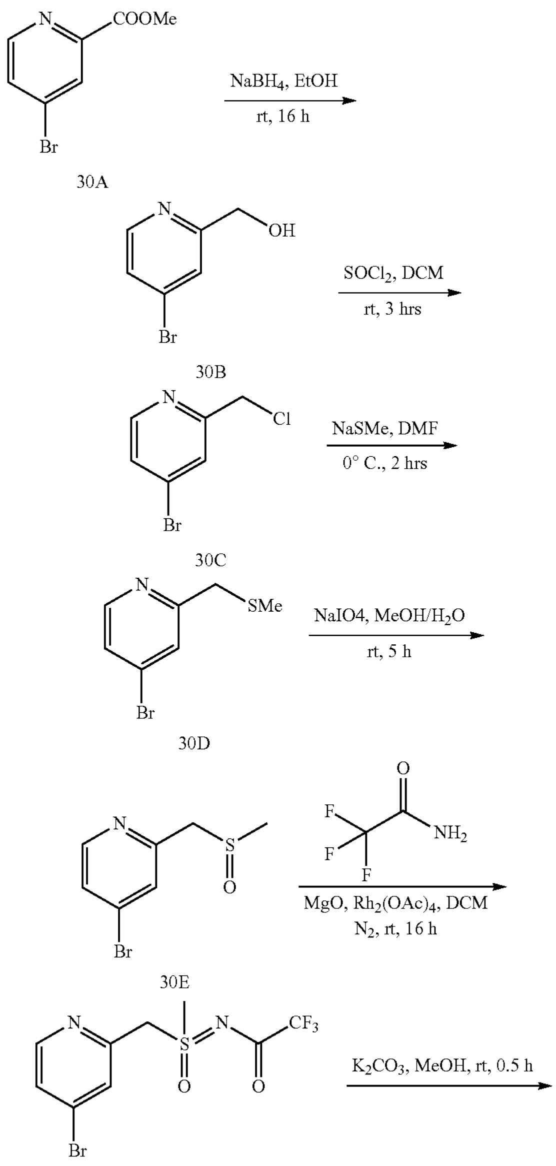

30A

30B

30C

30D

30E

30F

-continued

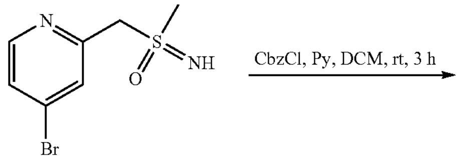

30G

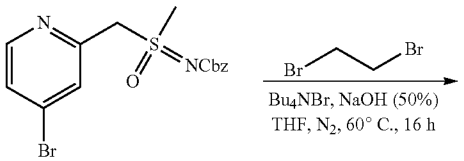

30H

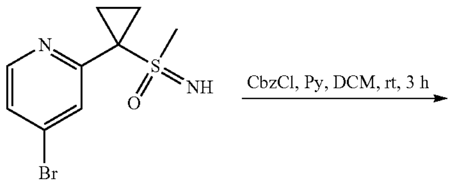

30I

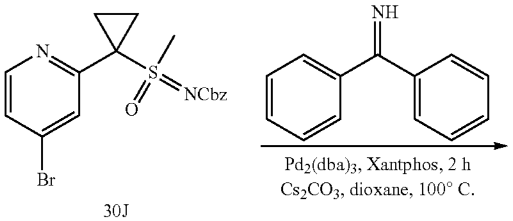

30J

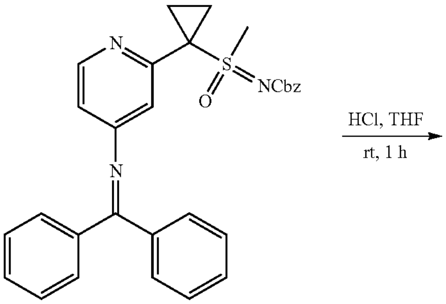

30K

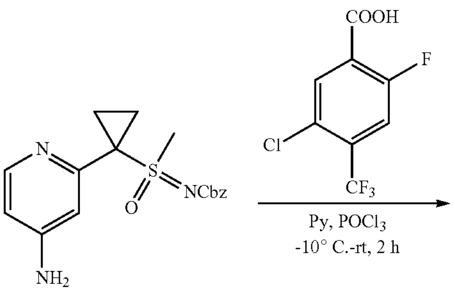

30L

-continued

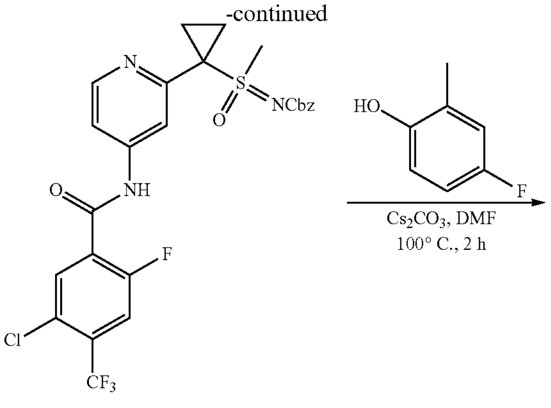

30M

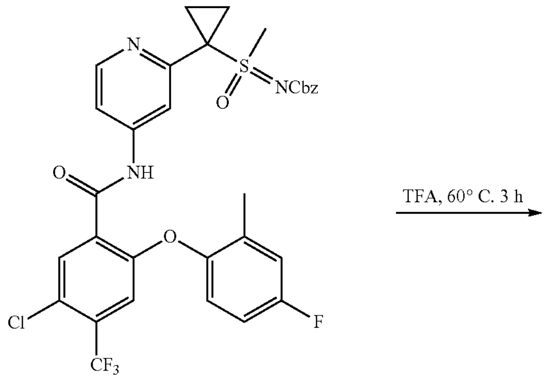

30N

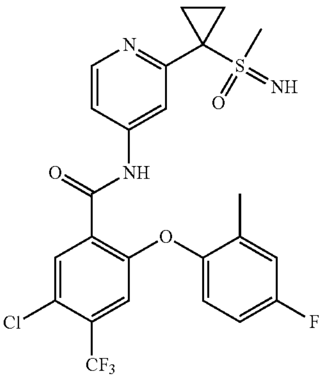

Compound 30

Step 1: (4-bromopyridin-2-yl)methanol

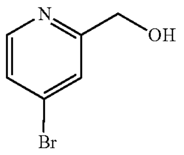

Methyl 4-bromopyridine-2-carboxylate (2 g, 9.258 mmol) was dissolved in ethanol (50 mL), and sodium borohydride (771 mg, 20.381 mmol) was added. Nitrogen replacement was performed, and then the mixture was allowed to react at room temperature for 16 hours. The reaction was stopped. The mixture was spun in vacuo to remove the solvent, and the residue was separated and purified by column chromatography (silica gel, petroleum ether:ethyl acetate=2:1) to obtain the title compound (1.23 g, yield: 70.7%, white solid). MS (ESI): m/z 188.0 $[M+H]^+$;

Step 2: 4-bromo-2-(chloromethyl)pyridine

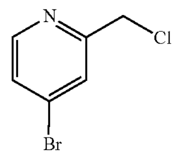

(4-bromopyridin-2-yl)methanol (9.7 g, 51.59 mmol) was dissolved in dichloromethane (60 mL), and thionyl chloride (9.21 mg, 77.414 mmol) was slowly added dropwise at 0° C. The mixture was allowed to react at room temperature for 3 hours. The reaction was stopped. The reaction solution was quenched by adding a saturated sodium bicarbonate solution (100 mL), and was extracted with dichloromethane (100 mL×3). The extract was dried over anhydrous sodium sulfate and was filtered. The filtrate was spun in vacuo to remove the solvent, and the residue was separated and purified by column chromatography (silica gel, petroleum ether:ethyl acetate=9:1) to obtain the title compound (10 g, yield: 85.1%, yellow oily matter). MS (ESI): m/z 206.0 $[M+H]^+$;

Step 3: 4-bromo-2-((methylthio)methyl)pyridine

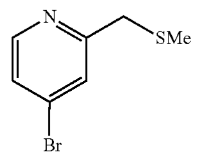

4-bromo-2-(chloromethyl)pyridine (10 g, 48.433 mmol) was dissolved in N,N-dimethylformamide (80 mL), and sodium thiomethoxide (4.07 mg, 58.076 mmol) was slowly added at 0° C. The mixture was allowed to react at 0° C. for 2 hours. The reaction was stopped. The reaction solution was poured into water (100 mL), and was extracted with ethyl acetate (100 mL×3). The combined organic phase was washed with a saturated saline solution (50 mL×3), dried over anhydrous sodium sulfate, and filtered. The filtrate was spun in vacuo to remove the solvent, and the residue was separated and purified by column chromatography (silica gel, petroleum ether:ethyl acetate=5:1) to obtain the title compound (9.3 g, yield: 88.1%, yellow oily matter).

MS (ESI): m/z 218.1 $[M+H]^+$;

Step 4: 4-bromo-2-((methylsulfinyl)methyl)pyridine

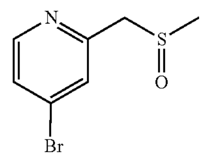

4-bromo-2-((methylthio)methyl)pyridine (4 g, 18.34 mmol) was dissolved in a mixed solvent of methanol (50 mL) and water (10 mL), and sodium periodate (3.93 g, 18.34 mmol) was slowly added at 0° C. The mixture was allowed to react at room temperature for 5 hours. The reaction was stopped, and the mixture was spun in vacuo to remove the solvent. The residue was separated and purified by column chromatography (silica gel, dichloromethane:methanol=9:1) to obtain the title compound (4.1 g, yield: 96.47%, white solid).

MS (ESI): m/z 234.0 $[M+H]^+$;

Step 5: N-(((4-bromopyridin-2-yl)methyl)(methyl)(oxo)-$\lambda^6$-sulfanylidene)-2,2,2-trifluoroacetamide

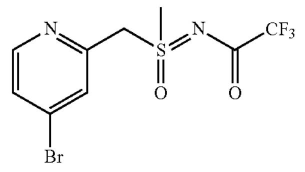 [SMILES: CS(=O)(Cc1cc(Br)ccn1)=NC(=O)C(F)(F)F]

4-bromo-2-((methylsulfinyl)methyl)pyridine (2 g, 8.584 mmol) was dissolved in dichloromethane (20 mL), and 2,2,2-trifluoroacetamide (1.94 g, 17.17 mmol), magnesium oxide (1.34 g, 34.33 mmol), rhodium acetate (190 g, 0.43 mmol), and iodobenzene acetate (5.53 g, 17.17 mmol) were added. Nitrogen replacement was performed, and the mixture was then allowed to react at room temperature for 16 hours. The reaction was stopped, and the mixture was spun in vacuo to remove the solvent. The residue was separated and purified by column chromatography (silica gel, petroleum ether:ethyl acetate=1:1) to obtain the title compound (1.18 g, yield: 40.2%, yellow oily matter).

MS (ESI): m/z 345.0 $[M+H]^+$;

Step 6: ((4-bromopyridin-2-yl)methyl)(imino)(methyl)-$\lambda^6$-sulfoxide

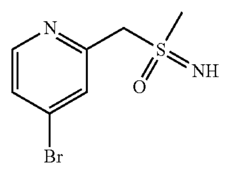

N-(((4-bromopyridin-2-yl)methyl)(methyl)(oxo)-$\lambda^6$-sulfanylidene)-2,2,2-trifluoroacetamide (1.13 g, 3.285 mmol) was dissolved in methanol (10 mL), and potassium carbonate (2.27 g, 16.424 mmol) was added. The mixture was allowed to react at room temperature for 1 hour. The reaction was stopped, and the mixture was spun in vacuo to remove the solvent. The residue was separated and purified by column chromatography (silica gel, dichloromethane: methanol=8:1) to obtain the title compound (660 mg, yield: 81.08%, yellow oily matter).

MS (ESI): m/z 249.0 $[M+H]^+$;

Step 7: Benzyl (((4-bromopyridin-2-yl)methyl)(methyl)(oxo)-λ$^6$-sulfanylidene)carbamate

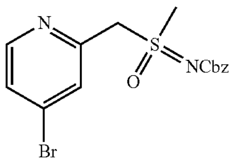

((4-bromopyridin-2-yl)methyl)(imino)(methyl)-λ$^6$-sulfoxide (660 mg, 2.66 mmol) was dissolved in dichloromethane (10 mL), pyridine (632 mg, 8 mmol) was added, and after cooling to 0° C., benzyl chloroformate (1.09 g, 6.4 mmol) was slowly added dropwise. The mixture was then allowed to react at room temperature for 3 hours. The reaction was stopped. The mixture was spun in vacuo to remove the solvent, and the residue was diluted with water (10 mL). The resulting solution was adjusted to be slightly acidic using 1 N dilute hydrochloric acid, and was extracted with ethyl acetate (30 mL×3). The combined organic phase was washed with a saturated saline solution (20 mL×3), dried over anhydrous sodium sulfate, and separated and purified by column chromatography (silica gel, petroleum ether:ethyl acetate=1:1) to obtain the title compound (900 mg, yield: 88.58%, yellow oily matter).

MS (ESI): m/z 383.1 [M+H]$^+$;

Step 8: (1-(4-bromopyridin-2-yl)cyclopropyl)(imino)(methyl)-λ$^6$-sulfoxide

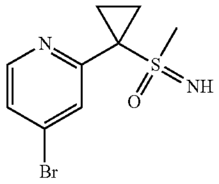

Benzyl (((4-bromopyridin-2-yl)methyl)(methyl)(oxo)-λ$^6$-sulfanylidene)carbamate (680 mg, 1.78 mmol) was dissolved in tetrahydrofuran (12.8 mL), tetrabutylammonium bromide (57.4 mg, 0.178 mmol) and 1,2-dibromoethane 9 (1.34 g, 7.12 mmol) were added, and a sodium hydroxide solution (50%, 3.2 mL) was slowly added dropwise. The mixture was then heated to 60° C. and allowed to react for 16 hours. The reaction was stopped. The mixture was spun in vacuo to remove the solvent, and the residue was diluted with water (10 mL). The resulting solution was adjusted to be slightly acidic using 1 N dilute hydrochloric acid, and was extracted with ethyl acetate (30 mL×3). The combined organic phase was washed with a saturated saline solution (20 mL×3), dried over anhydrous sodium sulfate, and separated and purified by column chromatography (silica gel, dichloromethane:methanol=20:1) to obtain the title compound (400 mg, yield: 81.96%, yellow solid).

MS (ESI): m/z 275.0 [M+H]$^+$;

Step 9: Benzyl ((1-(4-bromopyridin-2-yl)cyclopropyl)(methyl)(oxo)-λ$^6$-sulfanylidene)carbamate

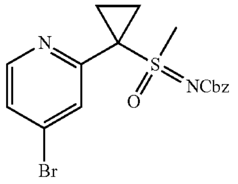

(1-(4-bromopyridin-2-yl)cyclopropyl)(imino)(methyl)-λ$^6$-sulfoxide (400 mg, 1.46 mmol) was dissolved in dichloromethane (6 mL), pyridine (346 mg, 4.38 mmol) was added, and after cooling to 0° C., benzyl chloroformate (623 g, 3.65 mmol) was slowly added dropwise. The mixture was then allowed to react at room temperature for 3 hours. The reaction was stopped. The mixture was spun in vacuo to remove the solvent, and the residue was diluted with water (10 mL). The resulting solution was adjusted to be slightly acidic using 1 N dilute hydrochloric acid, and was extracted with ethyl acetate (30 mL×3). The combined organic phase was washed with a saturated saline solution (20 mL×3), dried over anhydrous sodium sulfate, and separated and purified by column chromatography (silica gel, petroleum ether:ethyl acetate=1:1) to obtain the title compound (400 mg, yield: 67.11%, yellow oily matter).

MS (ESI): m/z 409.0 [M+H]$^+$;

Step 10: Benzyl ((1-(4-((diphenylmethylene)amino)pyridin-2-yl)cyclopropyl)(methyl)(oxo)-λ$^6$-sulfanylidene)carbamate

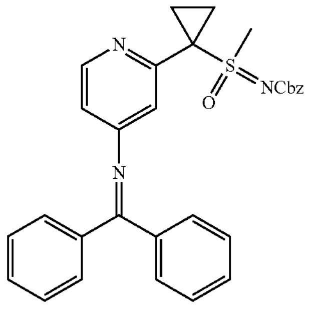

Benzyl ((1-(4-bromopyridin-2-yl)cyclopropyl)(methyl)(oxo)-λ$^6$-sulfanylidene)carbamate (330 mg, 0.81 mmol) and dibenzylimine (220 mg, 1.21 mmol) were dissolved in 1,4-dioxane (5 mL), and tris(dibenzylideneacetone)dipalladium (18.2 mg, 0.08 mmol), (9,9-dimethyl-9H-xanthene-4,5-diyl)bis(diphenylphosphine) (94 mg, 0.162 mmol), and cesium carbonate (790 mg, 2.43 mmol) were added. After replacement with nitrogen, the mixture was allowed to react in an oil bath at 100° C. for 2 hours. The reaction was stopped. The reaction solution was quenched by adding a saturated ammonium chloride solution (10 mL), and was extracted using ethyl acetate (30 mL×3). The combined organic phase was washed with a saturated saline solution (20 mL×3), and dried over anhydrous sodium sulfate. After separation and purification by column chromatography (silica gel, petroleum ether:ethyl acetate=1:2), the title compound (400 mg, yield: 97.08%, yellow oily matter) was obtained.

MS (ESI): m/z 510.5 [M+H]$^+$;

Step 11: Benzyl ((1-(4-aminopyridin-2-yl)cyclopropyl)(methyl)(oxo)-λ6-sulfanylidene)carbamate

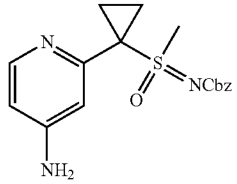

Benzyl ((1-(4-((diphenylmethylene)amino)pyridin-2-yl) cyclopropyl)(methyl)(oxo)-λ6-sulfanylidene)carbamate (420 mg, 0.825 mmol) was dissolved in tetrahydrofuran (4 mL), and 1 N dilute hydrochloric acid (4 mL) was slowly added dropwise. The mixture was allowed to react at room temperature for 1 hour. The reaction was stopped, and the mixture was spun in vacuo to remove the solvent. The residue was adjusted to be slightly alkaline by adding a 1 N sodium hydroxide solution, and was extracted with ethyl acetate (20 mL×3). The combined organic phase was washed with a saturated saline solution (20 mL×3), and dried over anhydrous sodium sulfate. After filtration, the filtrate was spun in vacuo to remove the solvent to obtain the title compound (270 mg, yield: 68.4%, white solid).

MS (ESI): m/z 346.1 [M+H]+;

Step 12: Benzyl ((1-(4-(5-chloro-2-fluoro-4-(trifluoromethyl)benzamido)pyridin-2-yl)cyclopropyl)(methyl)(oxo)-λ6-sulfanylidene)carbamate

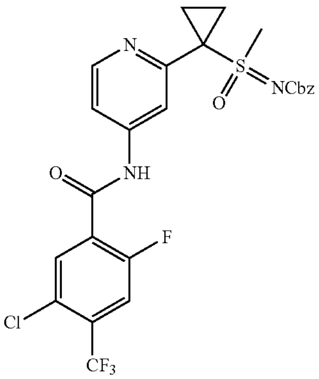

Benzyl ((1-(4-aminopyridin-2-yl)cyclopropyl)(methyl)(oxo)-λ6-sulfanylidene)carbamate (205 mg, 0.594 mmol) and 5-chloro-2-fluoro-4-(trifluoromethyl)benzoic acid (144.1 mg, 0.594 mmol) were dissolved in pyridine (4 mL). After replacement with nitrogen, the temperature was lowered to −10° C. in an ice salt bath, and phosphorus oxychloride (274 mg, 1.783 mmol) was slowly added dropwise. The mixture was allowed to react at room temperature for 2 hours. The reaction solution was poured into ice water (30 mL), adjusted to be slightly acidic using 1 N dilute hydrochloric acid, and extracted with ethyl acetate (30 mL×3). The combined organic phase was washed with a saturated saline solution (20 mL×3), dried over anhydrous sodium sulfate, and separated and purified by column chromatography (silica gel, petroleum ether:ethyl acetate=1:4) to obtain the title compound (300 mg, yield: 88.76%, yellow solid).

MS (ESI): m/z 570.0 [M+H]+;

Step 13: Benzyl ((1-(4-(5-chloro-2-(4-fluoro-2-methylphenoxy)-4-(trifluoromethyl)benzamido)pyridin-2-yl)cyclopropyl)(methyl)(oxo)-λ6-sulfanylidene)carbamate

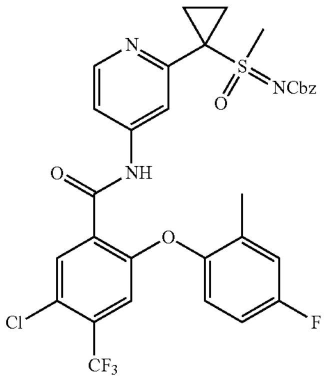

Benzyl ((1-(4-(5-chloro-2-fluoro-4-(trifluoromethyl)benzamido)pyridin-2-yl)cyclopropyl)(methyl)(oxo)-λ6-sulfanylidene)carbamate (75 mg, 0.132 mmol) and 4-fluoro-2-methylphenol (20 mg, 0.158 mmol) were dissolved using N,N-dimethylformamide (2 mL), and cesium carbonate (86 mg, 0.264 mmol) was added. The mixture was heated to 100° C. and allowed to react for 2 hours. The reaction was stopped. The reaction solution was quenched by adding a saturated ammonium chloride solution (10 mL), and was extracted using ethyl acetate (20 mL×3). The combined organic phase was washed with a saturated saline solution (10 mL×3). The organic phase was collected and dried over anhydrous sodium sulfate. After separation and purification by column chromatography (silica gel, petroleum ether:ethyl acetate=1:3), the title compound (110 mg, yield: 93.2%, yellow oily matter) was obtained.

MS (ESI): m/z 676.1 [M+H]+;

Step 14: 5-chloro-2-(4-fluoro-2-methylphenoxy)-N-(2-(1-(S-methyliminosulfonyl)cyclopropyl)pyridin-4-yl)-4-(trifluoromethyl)benzamide (Compound 30)

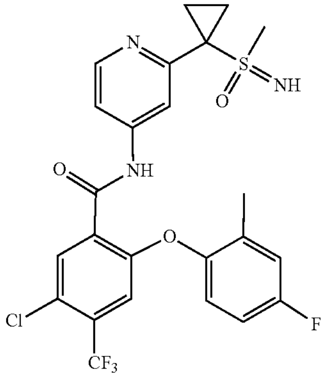 [SMILES: Cc1cc(F)ccc1Oc1cc(C(F)(F)F)c(Cl)cc1C(=O)Nc1ccnc(C2(S(C)(=N)=O)CC2)c1]

Benzyl ((1-(4-(5-chloro-2-(4-fluoro-2-methylphenoxy)-4-(trifluoromethyl)benzamido)pyridin-2-yl)cyclopropyl)(methyl)(oxo)-$\lambda^6$-sulfanylidene)carbamate (70 mg, 0.103 mmol) was dissolved using trifluoroacetic acid (1.5 mL), and the mixture was heated to 60° C. and allowed to react for 3 hours. The reaction was stopped, and the mixture was spun in vacuo to remove the solvent. The residue was adjusted to be slightly alkaline by adding a 1 N sodium hydroxide solution, and was extracted with ethyl acetate (2 mL×3). The combined organic phases was washed with a saturated saline solution (5 mL×3) and dried over anhydrous sodium sulfate. The mixture was spun in vacuo to remove the solvent. After preparation and purification by high performance liquid chromatography (elution system: ammonium bicarbonate, water, and acetonitrile), the title compound (32 mg, yield: 57.14%, white solid) was obtained.

MS (ESI): m/z 542.0 $[M+H]^+$;

$^1H$ NMR (400 MHz, DMSO-$d_6$) δ 11.06 (s, 1H), 8.46 (d, J=5.6 Hz, 1H), 8.08 (s, 1H), 7.87 (d, J=1.4 Hz, 1H), 7.60 (dd, J=5.5, 1.9 Hz, 1H), 7.24-7.18 (m, 1H), 7.11-7.08 (m, 3H), 3.71 (s, 1H), 2.91 (s, 3H), 2.16 (s, 3H), 1.81-1.73 (m, 1H), 1.48-1.41 (m, 1H), 1.31-1.20 (m, 2H).

Example 31

5-chloro-N-(2-(1-(S-methyliminosulfonyl)cyclopropyl)pyridin-4-yl)-2-(4-(trifluoromethoxy)phenoxy)-4-(trifluoromethyl)benzamide (Compound 31)

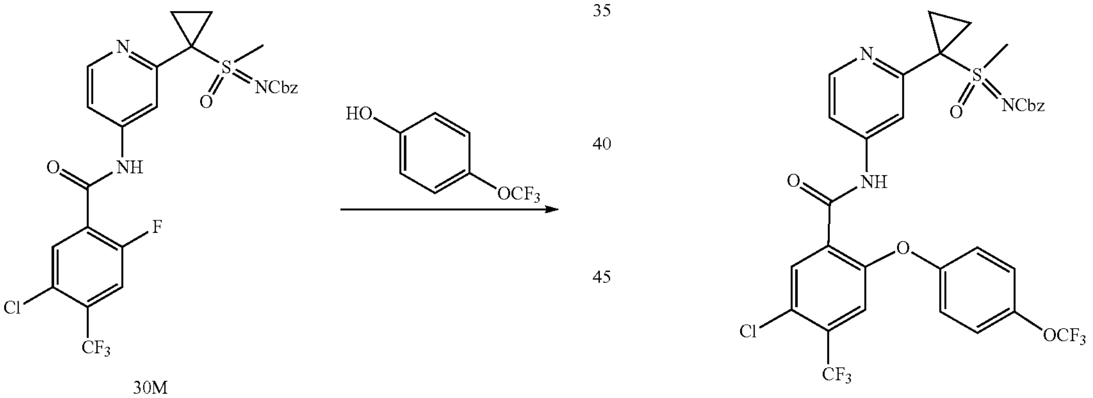

30M

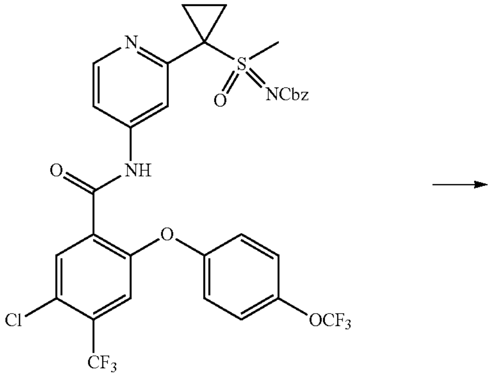

31A

-continued

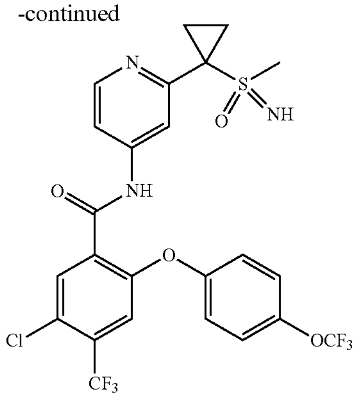

Compound 31

Step 1: Benzyl ((1-(4-(5-chloro-2-(4-(trifluoromethoxy)phenoxy)-4-(trifluoromethyl)benzamido)pyridin-2-yl)cyclopropyl)(methyl)(oxo)-$\lambda^6$-sulfanylidene)carbamate Benzyl ((1-(4-(5-chloro-2-fluoro-4-(trifluoromethyl)benzamido)pyridin-2-yl)cyclopropyl)(methyl)(oxo)-$\lambda^6$-sulfanylidene)carbamate (75 mg, 0.132 mmol) and 4-(trifluoromethoxy)phenol 2 (47 mg, 0.264 mmol) were dissolved in N,N-dimethylformamide (2 mL), and potassium carbonate (37 mg, 0.264 mmol) was added. The mixture was heated to 70° C. and allowed to react for 16 hours. The reaction was stopped. The reaction solution was quenched by adding a saturated ammonium chloride solution (10 mL), and was extracted using ethyl acetate (20 mL×3). The combined organic phase was washed with a saturated saline solution (10 mL×3) and dried over anhydrous sodium sulfate. After separation and purification by column chromatography (silica gel, petroleum ether:ethyl acetate=1:3), the title compound (80 mg, yield: 83%, yellow oily matter) was obtained.

MS (ESI): m/z 728.0 $[M+H]^+$;

Step 2: 5-chloro-N-(2-(1-(S-methyliminosulfonyl)cyclopropyl)pyridin-4-yl)-2-(4-(trifluoromethoxy)phenoxy)-4-(trifluoromethyl)benzamide (Compound 31)

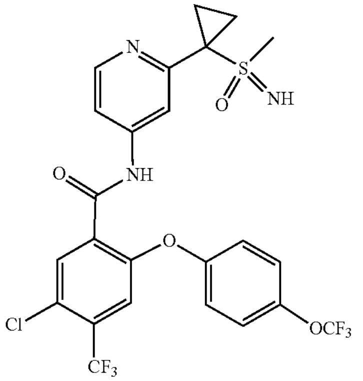 [SMILES: CS(=N)(=O)C1(c2cc(NC(=O)c3cc(Cl)c(C(F)(F)F)cc3Oc3ccc(OC(F)(F)F)cc3)ccn2)CC1]

Benzyl ((1-(4-(5-chloro-2-(4-(trifluoromethoxy)phenoxy)-4-(trifluoromethyl)benzamido)pyridin-2-yl)cyclopropyl)(methyl)(oxo)-$\lambda^6$-sulfanylidene)carbamate (70 mg, 0.102 mmol) was dissolved using trifluoroacetic acid (1.5 mL), and the mixture was heated to 60° C. and allowed to react for 3 hours. The reaction was stopped, and the mixture was spun in vacuo to remove the solvent. The residue was adjusted to be slightly alkaline by adding a 1 N sodium hydroxide solution, and was extracted with ethyl acetate (2 mL×3). The combined organic phase was washed with a saturated saline solution (5 mL×3) and dried over anhydrous sodium sulfate. The mixture was spun in vacuo to remove the solvent. After preparation and purification by high performance liquid chromatography (elution system: ammonium bicarbonate, water, and acetonitrile), the title compound (39.27 mg, yield: 68.42%, white solid) was obtained.

MS (ESI): m/z 594.0 $[M+H]^+$;

$^1H$ NMR (400 MHz, DMSO-$d_6$) δ 11.05 (s, 1H), 8.44 (d, J=5.6 Hz, 1H), 8.12 (s, 1H), 7.83 (d, J=1.5 Hz, 1H), 7.57 (dd, J=5.5, 1.8 Hz, 1H), 7.50 (s, 1H), 7.40 (d, J=8.5 Hz, 2H), 7.24-7.19 (m, 2H), 3.71 (s, 1H), 2.90 (s, 3H), 1.76 (brs, 1H), 1.44 (brs, 1H), 1.30-1.19 (m, 2H).

Example 32

5-chloro-2-(4,4-difluoroazepan-1-yl)-N-(2-(1-(S-methyliminosulfonyl)cyclopropyl)pyridin-4-yl)-4-(trifluoromethyl)benzamide (Compound 32)

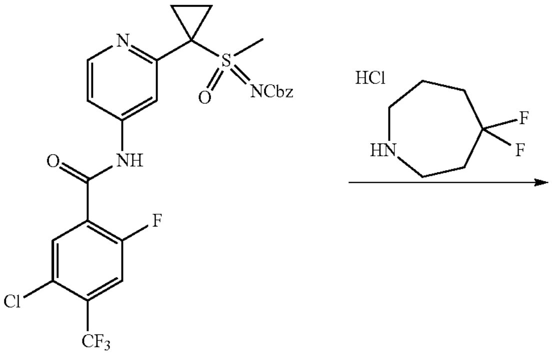

30M

-continued

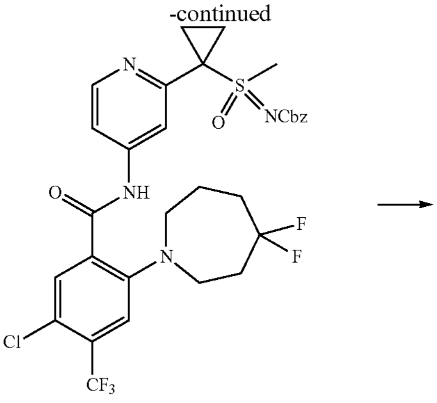

32A

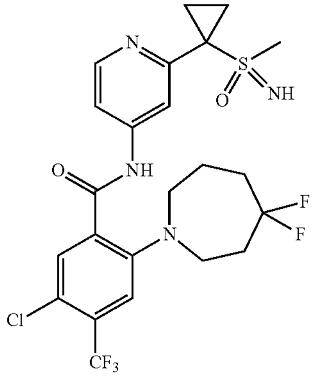

Compound 32

Step 1: Benzyl ((1-(4-(5-chloro-2-(4,4-difluoroazepan-1-yl)-4-(trifluoromethyl)benzamido)pyridin-2-yl)cyclopropyl)(methyl)(oxo)-$\lambda^6$-sulfanylidene)carbamate

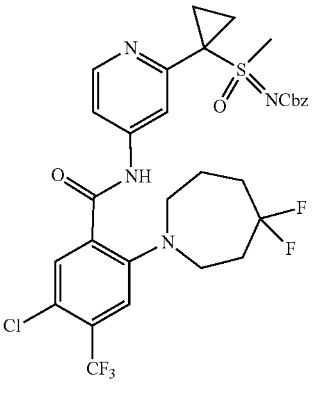

Benzyl ((1-(4-(5-chloro-2-fluoro-4-(trifluoromethyl)benzamido)pyridin-2-yl)cyclopropyl)(methyl)(oxo)-$\lambda^6$-sulfanylidene)carbamate (75 mg, 0.132 mmol) and 4,4-difluoroazepane hydrochloride (113 mg, 0.66 mmol) were dissolved using N,N-dimethylformamide (2 mL), and cesium carbonate (300 mg, 0.923 mmol) was added. The mixture was heated to 100° C. and allowed to react for 16 hours. The reaction was stopped. The reaction solution was quenched by adding a saturated ammonium chloride solution (10 mL), and was extracted using ethyl acetate (20 mL×3). The combined organic phase was washed with a saturated saline solution (10 mL×3) and dried over anhydrous sodium sulfate. After separation and purification by column chromatography (silica gel, petroleum ether:ethyl acetate=1:3), the title compound (80 mg, yield: 88%, yellow oily matter) was obtained.

MS (ESI): m/z 685.1 $[M+H]^+$;

Step 2: 5-chloro-2-(4,4-difluoroazepan-1-yl)-N-(2-(1-(S-methyliminosulfonyl)cyclopropyl)pyridin-4-yl)-4-(trifluoromethyl)benzamide (Compound 32)

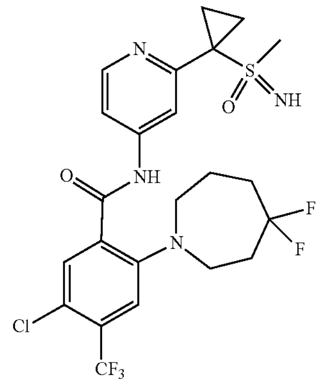 [SMILES: CS(=N)(=O)C1(c2cc(NC(=O)c3cc(Cl)c(C(F)(F)F)cc3N3CCCC(F)(F)CC3)ccn2)CC1]

Benzyl ((1-(4-(5-chloro-2-(4,4-difluoroazepan-1-yl)-4-(trifluoromethyl)benzamido)pyridin-2-yl)cyclopropyl)(methyl)(oxo)-$\lambda^6$-sulfanylidene)carbamate (70 mg, 0.102 mmol) was dissolved using trifluoroacetic acid (1.5 mL), and the mixture was heated to 60° C. and allowed to react for 3 hours. The reaction was stopped, and the mixture was spun in vacuo to remove the solvent. The residue was adjusted to be slightly alkaline by adding a 1 N sodium hydroxide solution, and was extracted with ethyl acetate (2 mL×3). The combined organic phase was washed with a saturated saline solution (5 mL×3) and dried over anhydrous sodium sulfate. The mixture was spun in vacuo to remove the solvent. After preparation and purification by high performance liquid chromatography (elution system: ammonium bicarbonate, water, and acetonitrile), the title compound (19.21 mg, yield: 34.12%, white solid) was obtained.

MS (ESI): m/z 551.1 $[M+H]^+$;

$^1$H NMR (400 MHz, DMSO-$d_6$) δ 10.97 (s, 1H), 8.47 (d, J=5.5 Hz, 1H), 7.85 (s, 1H), 7.73-7.67 (m, 2H), 7.36 (s, 1H), 3.69 (s, 1H), 3.42-3.33 (m, 4H), 2.92 (s, 3H), 2.24 (brs, 2H), 2.11-2.00 (m, 2H), 1.79 (brs, 3H), 1.49-1.43 (m, 1H), 1.31-1.21 (m, 2H).

Example 33

5-chloro-2-(4-fluoro-2-methylphenoxy)-N-(2-(2-(S-methyliminosulfonyl)ethoxy)pyridin-4-yl)-4-(trifluoromethyl)benzamide (Compound 33)

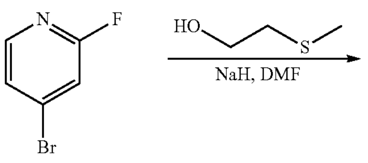

33A

-continued

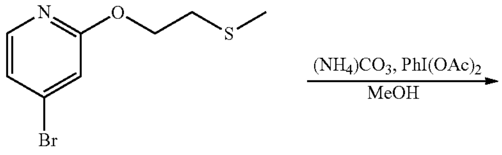

33B

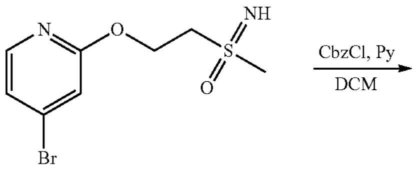

33C

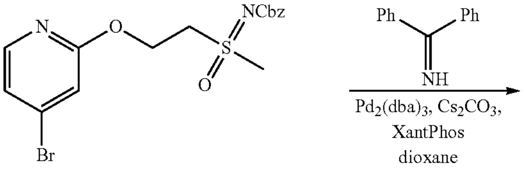

33D

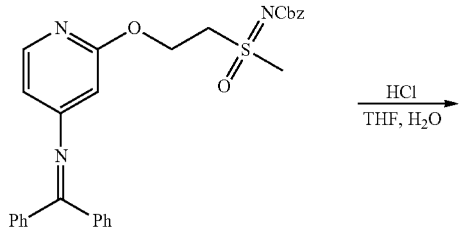

33E

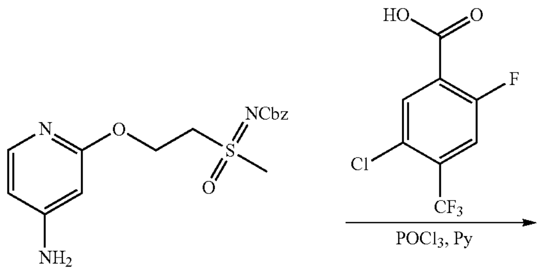

33F

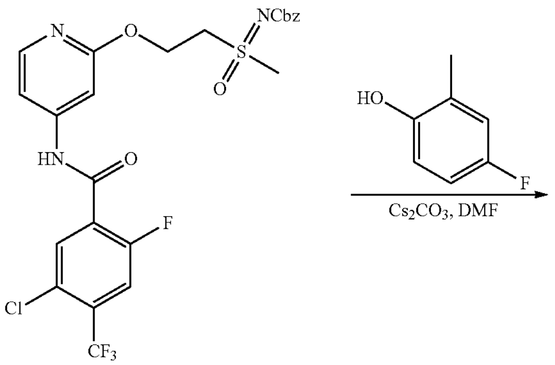

33G

-continued

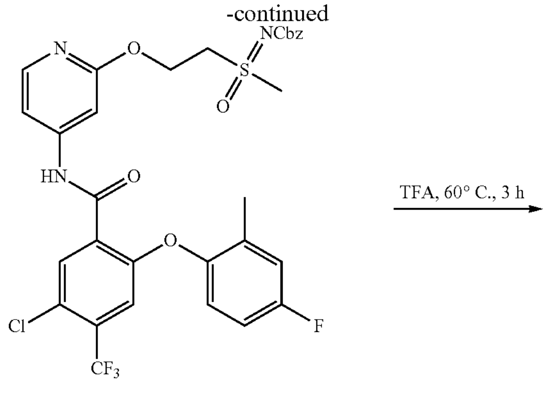

33H

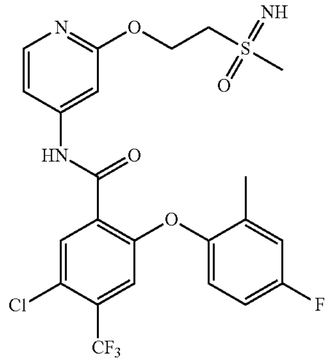

Compound 33

Step 1: 4-bromo-2-(2-(methylthio)ethoxy)pyridine

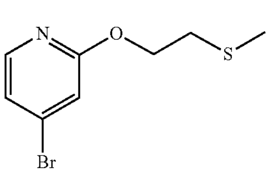

2-(methylthio)ethane-1-ol (3.14 g, 34.10 mmol) was dissolved in N,N-dimethylformamide (60 mL), and sodium hydrogen (1.70 g, 42.60 mmol) was added at 0° C. and allowed to react for 0.5 hours. 4-bromo-2-fluoropyridine (5.00 g, 28.40 mmol) was added under nitrogen, and reaction was continued at 0° C. for 2 hours. The reaction was stopped, and water was slowly added (250 mL) to quench the reaction. The aqueous phase was extracted using ethyl acetate (250 ml×3). The organic phases were combined, washed with a saturated saline solution (250 ml×2), dried over anhydrous sodium sulfate, and spun dry in vacuo to obtain a crude product. The crude product was separated and purified by silica gel column chromatography (mobile phase: petroleum ether:ethyl acetate=97:3) to obtain the title compound (5.00 g, yield: 71.0%, colorless oily matter).

MS (ESI): m/z 247.9 $[M+H]^+$;

Step 2: (2-((4-bromopyridin-2-yl)oxy)ethyl)(imino)(methyl)-$\lambda^6$-sulfoxide

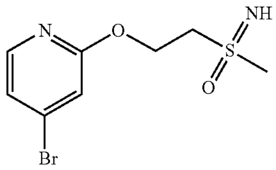

4-bromo-2-(2-(methylthio)ethoxy)pyridine (4.5 g, 18.13 mmol) was dissolved in methanol (50 mL), ammonium carbonate (5.2 g, 54.40 mmol) was added, and then iodobenzene diacetate (23.3 g, 72.53 mmol) was added in an ice bath. Nitrogen replacement was performed, and the mixture was stirred and allowed to react at room temperature for 2 hours. The reaction was stopped, and the reaction solution was quenched by adding water (200 ml). The aqueous phase was extracted using ethyl acetate (200 ml×3). The organic phases were combined, washed with a saturated saline solution (200 ml×2), dried over anhydrous sodium sulfate, and spun dry in vacuo to obtain a crude product. The crude product was separated and purified by a reverse column (mobile phase: water:methanol=85:15) to obtain the title compound (900 mg, yield: 17.7%, yellow oily matter).

MS (ESI): m/z 279.0 $[M+H]^+$;

Step 3: Benzyl ((2-((4-bromopyridin-2-yl)oxy)ethyl)(methyl)(oxo)-$\lambda^6$-sulfanylidene)carbamate

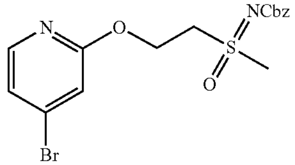

(2-((4-bromopyridin-2-yl)oxy)ethyl)(imino)(methyl)-$\lambda^6$-sulfoxide (700 mg, 2.50 mmol) was dissolved in DCM (10 mL), and pyridine (297 mg, 3.76 mmol) was added. After replacement with nitrogen, CbzCl (513 mg, 3.00 mmol) was added in an ice bath, and the mixture was stirred and allowed to react at room temperature for 2 hours. The reaction was stopped. The reaction solution was quenched by adding water (50 mL). The aqueous phase was extracted using ethyl acetate (50 mL×3). The organic phases were combined, washed with a saturated saline solution (5 mL×2), dried over anhydrous sodium sulfate, and spun dry in vacuo to obtain a crude product. The crude product was separated and purified by silica gel column chromatography (mobile phase: petroleum ether:ethyl acetate=1:1) to obtain the title compound (800 mg, yield: 77.2%, colorless oily matter).

MS (ESI): m/z 415.0 $[M+H]^+$;

Step 4: Benzyl ((2-((4-((diphenylmethylene)amino)pyridin-2-yl)oxy)ethyl)(methyl)(oxo)-$\lambda^6$-sulfanylidene)carbamate

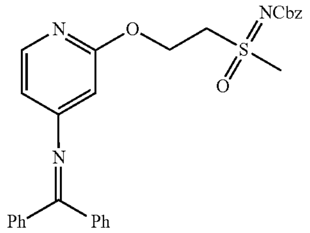

Benzyl ((2-((4-bromopyridin-2-yl)oxy)ethyl)(methyl)(oxo)-$\lambda^6$-sulfanylidene)carbamate (700 mg, 1.69 mmol) was dissolved in dioxane (10 mL), and diphenylimine (458 mg, 2.54 mmol), tris(dibenzylideneacetone)dipalladium (154 mg, 0.16 mmol), (9,9-dimethyl-9H-xanthene-4,5-diyl)bis(diphenylphosphine) (195 mg, 0.33 mmol), and cesium carbonate (1654 mg, 5.08 mmol) were added. Nitrogen replacement was performed, and the mixture was stirred and allowed to react at 100° C. for 1.5 hours. The reaction was stopped, the reaction solution was cooled, and water (100 mL) was added thereto. The aqueous phase was extracted using ethyl acetate (100 ml×3). The organic phases were combined, washed with a saturated saline solution (3 ml×2), dried over anhydrous sodium sulfate, and spun dry in vacuo to obtain a crude product. The crude product was separated and purified by a thin-layer chromatography plate (developer system: ethyl acetate) to obtain the title compound (550 mg, yield: 63.2%, yellow solid).

MS (ESI): m/z 514.2 $[M+H]^+$;

Step 5: Benzyl ((2-((4-aminopyridin-2-yl)oxy)ethyl)(methyl)(oxo)-$\lambda^6$-sulfanylidene)carbamate

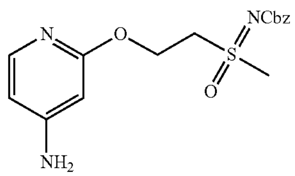

Benzyl ((2-((4-((diphenylmethylene)amino)pyridin-2-yl)oxy)ethyl)(methyl)(oxo)-$\lambda^6$-sulfanylidene)carbamate (500 mg, 0.97 mmol) was dissolved in tetrahydrofuran (2 mL), and water (1 mL) and hydrochloric acid (1 mL) were added. Nitrogen replacement was performed, and the mixture was allowed to react at room temperature for 1.5 hours. The reaction solution was spun dry in vacuo to obtain the crude title compound (400 mg, white solid), which was directly used in the next reaction.

MS (ESI): m/z 350.1 $[M+H]^+$;

Step 6: Benzyl ((2-((4-(5-chloro-2-fluoro-4-(trifluoromethyl)benzamide)pyridin-2-yl)oxy)ethyl)(methyl)(oxo)-$\lambda^6$-sulfanylidene)carbamate

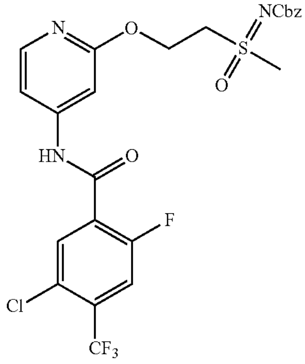

Benzyl ((2-((4-aminopyridin-2-yl)oxy)ethyl)(methyl)(oxo)-$\lambda^6$-sulfanylidene)carbamate (450 mg, 1.16 mmol) was dissolved in pyridine (15 mL), and 5-chloro-2-fluoro-4-(trifluoromethyl)benzoic acid (283 mg, 1.16 mmol) was added. After replacement with nitrogen, phosphorus oxychloride (536 mg, 3.50 mmol) was added in an ice bath, and the mixture was allowed to react at room temperature for 2 hours. The reaction was stopped, and water was added to the reaction solution (100 mL) in an ice bath. The aqueous phase was extracted using ethyl acetate (100 ml×3). The organic phases were combined, washed with a saturated saline solution (10 ml×2), dried over anhydrous sodium sulfate, and spun dry in vacuo to obtain a crude product. The crude product was separated and purified by silica gel column chromatography (mobile phase: petroleum ether:ethyl acetate=1:1) to obtain the title compound (450 mg, yield: 67.0%, yellow solid).

MS (ESI): m/z 574.1 $[M+H]^+$;

Step 7: Benzyl ((2-((4-(5-chloro-2-(4-fluoro-2-methylphenoxy)-4-(trifluoromethyl)benzamide)pyridin-2-yl)oxy)ethyl)(methyl)(oxo)-$\lambda^6$-sulfanylidene)carbamate

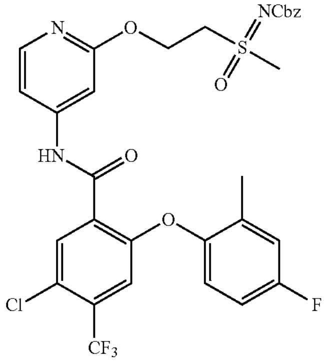

Benzyl ((2-((4-(5-chloro-2-fluoro-4-(trifluoromethyl)benzamide)pyridin-2-yl)oxy)ethyl)(methyl)(oxo)-$\lambda^6$-sulfanylidene)carbamate (80 mg, 0.13 mmol) was dissolved in DMF (2 mL), potassium carbonate (90 mg, 2.70 mmol) was added, and 4-fluoro-2-methylphenol (35 mg, 0.27 mmol)

was added. Nitrogen replacement was performed, and the mixture was allowed to react at 70° C. for 12 hours. The reaction was stopped, and water was added to the reaction solution (15 mL). The aqueous phase was extracted using ethyl acetate (15 ml×3). The organic phases were combined, washed with a saturated saline solution (10 ml×2), dried over anhydrous sodium sulfate, and spun dry in vacuo to obtain a crude product. The crude product was separated and purified by silica gel column chromatography (mobile phase: petroleum ether:ethyl acetate=2:1) to obtain the title compound (100 mg, yield: 86.4%, yellow solid).

MS (ESI): m/z 680.1 $[M+H]^+$;

Step 8: 5-chloro-2-(4-fluoro-2-methylphenoxy)-N-(2-(2-(S-methyliminosulfonyl)ethoxy)pyridin-4-yl)-4-(trifluoromethyl)benzamide (Compound 33)

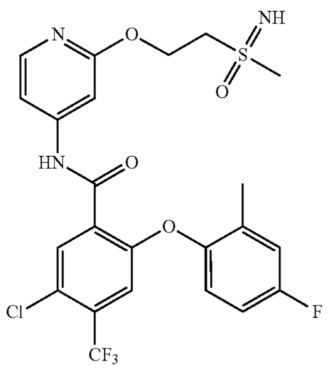 [SMILES: Cc1cc(F)ccc1Oc1cc(C(F)(F)F)c(Cl)cc1C(=O)Nc1ccnc(OCCS(C)(=N)=O)c1]

Benzyl ((2-((4-(5-chloro-2-(4-fluoro-2-methylphenoxy)-4-(trifluoromethyl)benzamide)pyridin-2-yl)oxy)ethyl) (methyl)(oxo)-$\lambda^6$-sulfanylidene)carbamate (80 mg, 0.118 mmol) was dissolved using trifluoroacetic acid (1.5 mL), and the mixture was heated to 60° C. and allowed to react for 3 hours. The reaction was stopped, and the mixture was spun in vacuo to remove the solvent. The residue was adjusted to be slightly alkaline by adding a 1 N sodium hydroxide solution, and was extracted with ethyl acetate (2 mL×3). The combined organic phase was washed with a saturated saline solution (5 mL×3), dried over anhydrous sodium sulfate, and filtered. The filtrate was spun in vacuo to remove the solvent. After preparation and purification by high performance liquid chromatography (elution system: ammonium bicarbonate, water, and acetonitrile), the title compound (34.87 mg, yield: 54.22%, white solid) was obtained.

MS (ESI): m/z 546.0 $[M+H]^+$;

$^1H$ NMR (400 MHz, DMSO-$d_6$) δ 10.75 (s, 1H), 8.06 (s, 1H), 7.67 (d, J=7.5 Hz, 1H), 7.22 (d, J=9.0 Hz, 1H), 7.09 (d, J=5.8 Hz, 3H), 6.82 (d, J=1.9 Hz, 1H), 6.42 (dd, J=7.5, 2.2 Hz, 1H), 4.21 (t, J=6.8 Hz, 2H), 3.88 (s, 1H), 3.43 (td, J=6.8, 2.7 Hz, 2H), 2.91 (s, 3H), 2.16 (s, 3H).

Example 34

2-(4-acetyl-1,4-diazepan-1-yl)-5-chloro-N-(2-(S-methylsulfonimido)pyridin-4-yl)-4-trifluoromethyl-benzamide (Compound 34)

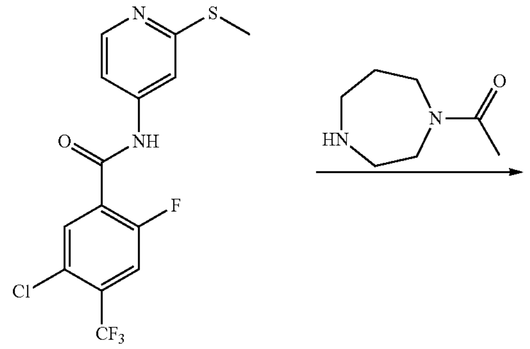

13C

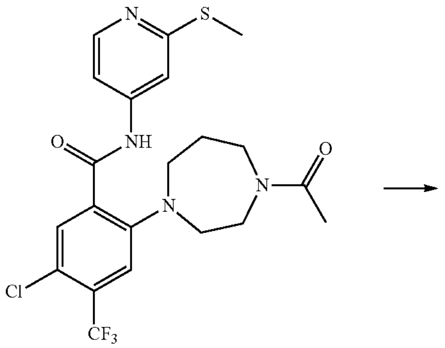

34A

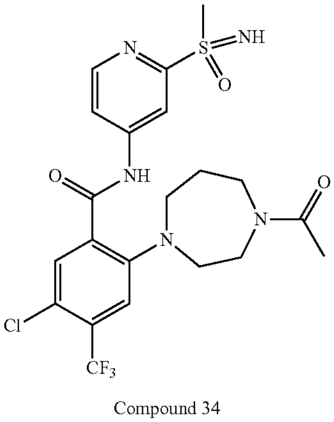

Compound 34

Step 1: 2-(4-acetyl-1,4-diazepan-1-yl)-5-chloro-N-(2-methylthio)pyridin-4-yl)-4-trifluoromethylbenzamide

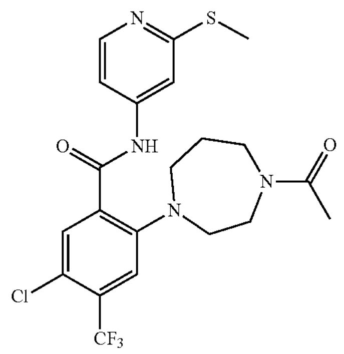 [SMILES: CSc1cc(NC(=O)c2cc(Cl)c(C(F)(F)F)cc2N2CCCN(C(C)=O)CC2)ccn1]

5-chloro-2-fluoro-N-(2-methylthio)pyridin-4-yl)-4-trifluoromethylbenzamide (120 mg, 0.33 mmol) was dissolved using N,N-dimethylformamide (2 mL), and 1-(1,4-diazepan-1-yl)ethan-1-one (140.8 mg, 0.99 mmol) and cesium carbonate (322.7 mg, 0.99 mmol) were added. Nitrogen replacement was performed, and the mixture was allowed to react at 100° C. for 16 hours. The reaction was stopped. Water was added to the reaction solution, and extraction was performed using ethyl acetate (10 mL×3). The combined organic phase was washed with a saturated saline solution (10 mL×3), dried over anhydrous sodium sulfate, and filtered. The filtrate was spun in vacuo to remove the solvent. After separation and purification by column chromatography (silica gel, petroleum ether:ethyl acetate=1:3), the title compound (90 mg, yield: 56.3%, white solid) was obtained.

MS (ESI): m/z 487.0 $[M+H]^+$;

Step 2: 2-(4-acetyl-1,4-diazepan-1-yl)-5-chloro-N-(2-(S-methylsulfonimido)pyridin-4-yl)-4-trifluoromethylbenzamide (Compound 34)

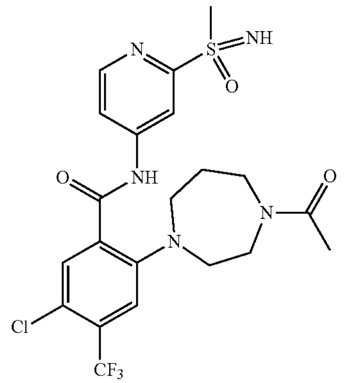 [SMILES: CC(=O)N1CCCN(c2cc(C(F)(F)F)c(Cl)cc2C(=O)Nc2ccnc(S(C)(=N)=O)c2)CC1]

2-(4-acetyl-1,4-diazepan-1-yl)-5-chloro-N-(2-methylthio)pyridin-4-yl)-4-trifluoromethylbenzamide (90 mg, 0.18 mmol) was dissolved using methanol (1 mL), and ammonium carbonate (18 mg, 0.54 mmol) and iodobenzene acetate (60.3 mg, 0.72 mmol) were added. The mixture was allowed to react at room temperature for 1 hour. The reaction was stopped, and the reaction solution was spun in vacuo to remove the solvent. After separation and purification by column chromatography (silica gel, dichloromethane:methane=20:1) followed by preparation and purification by high performance liquid chromatography (elution system: ammonium bicarbonate, water, and acetonitrile), the title compound (2 mg, yield: 2.1%, white solid) was obtained.

MS (ESI): m/z 518.1 $[M+H]^+$;

$^1H$ NMR (400 MHz, DMSO-$d_6$) δ 11.30 (s, 1H), 8.62 (d, J=5.4 Hz, 1H), 8.40 (d, J=3.2 Hz, 1H), 7.84 (d, J=5.5 Hz, 1H), 7.73 (d, J=17.0 Hz, 1H), 7.37 (d, J=10.9 Hz, 1H), 4.38 (s, 1H), 3.62-3.54 (m, 2H), 3.49-3.34 (m, 6H), 3.15 (s, 3H), 1.89 (s, 3H), 1.74 (brs, 2H).

Example 35

4-acetyl-1,4-diazacyclopenta-5-chloro-N-(4-fluoro-3-S-methanesulfonyliminophenyl)-4-trifluoromethylbenzamide (Compound 35)

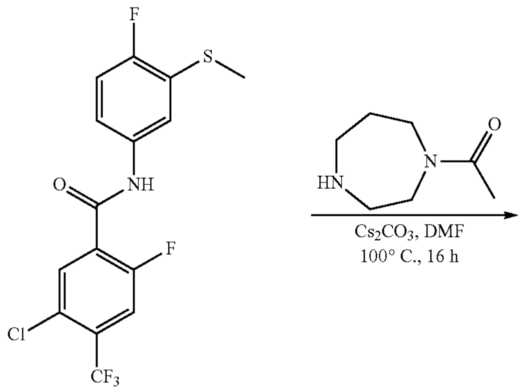

23C

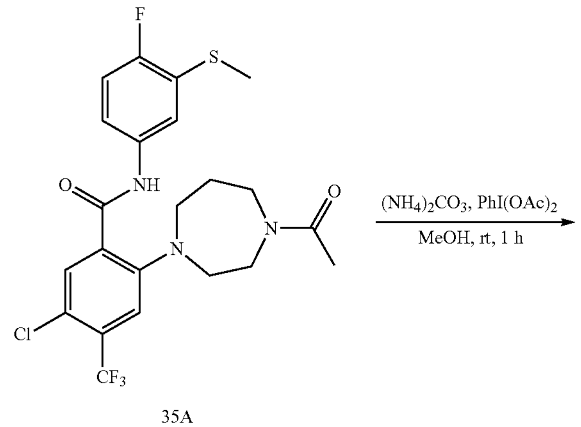

35A

-continued

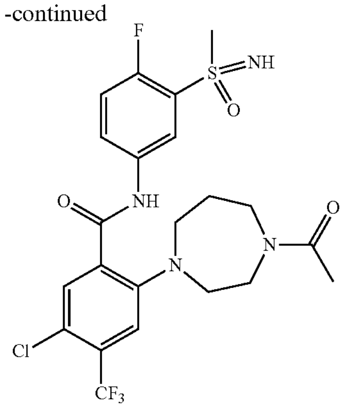

Compound 35

Step 1: 4-acetyl-1,4-diazacyclopenta-5-chloro-4-fluoro-3-methylthiobenzamide

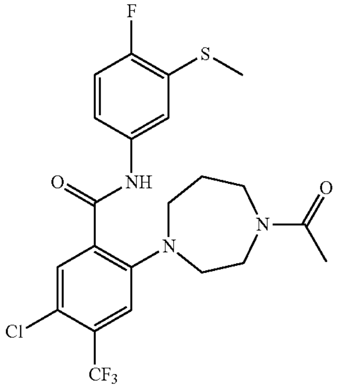 [SMILES: CSc1cc(NC(=O)c2cc(Cl)c(C(F)(F)F)cc2N2CCCN(C(C)=O)CC2)ccc1F]

5-chloro-2-fluoro-N-4-fluoro-3-methylthiobenzamide (100 mg, 0.262 mmol) and 1-(1,4-diazacyclopentenyl)ethanone (75 mg, 0.525 mmol) were dissolved in N,N-dimethylformamide (2 mL), and cesium carbonate (171 mg, 0.525 mmol) was added. The mixture was allowed to react in an oil bath at 100° C. for 16 hours. The reaction was stopped. The reaction solution was quenched by adding a saturated ammonium chloride solution (10 mL), and was extracted using ethyl acetate (30 mL×3). The combined organic phase was washed with a saturated saline solution (20 mL×3), dried over anhydrous sodium sulfate, and filtered. The filtrate was separated and purified by column chromatography (silica gel, petroleum ether:ethyl acetate=1:1), and the title compound (116 mg, yield: 88%, yellow oily matter) was obtained.

MS (ESI): m/z 504.1 $[M+H]^+$;

Step 2: 4-acetyl-1,4-diazacyclopenta-5-chloro-N-(4-fluoro-3-S-methanesulfonyliminophenyl)-4-trifluoromethylbenzamide (Compound 35)

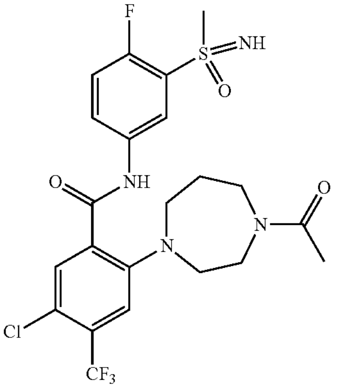 [SMILES: CC(=O)N1CCCN(c2cc(C(F)(F)F)c(Cl)cc2C(=O)Nc2ccc(F)c(S(C)(=N)=O)c2)CC1]

4-acetyl-1,4-diazacyclopenta-5-chloro-4-fluoro-3-methylthiobenzamide (96 mg, 0.19 mmol) was dissolved using methanol (2 mL), and ammonium carbonate (54.78 mg, 0.57 mmol) and iodobenzene diacetate (244.8 mg, 0.76 mmol) were added. The mixture was allowed to react at room temperature for 1 hour. The reaction was stopped, and the mixture was spun in vacuo to remove the solvent. After separation and purification by column chromatography (silica gel, ethyl acetate) followed by preparation and purification by high performance liquid chromatography (elution system: ammonium bicarbonate, water, and acetonitrile), the title compound (15.76 mg, yield: 14.85%, white solid) was obtained.

MS (ESI): m/z 535.1 $[M+H]^+$;

$^1H$ NMR (400 MHz, DMSO-$d_6$) δ 10.92 (s, 1H), 8.28 (d, J=4.3 Hz, 1H), 8.03-7.91 (m, 1H), 7.67 (d, J=16.7 Hz, 1H), 7.45 (t, J=9.3 Hz, 1H), 7.35 (d, J=9.6 Hz, 1H), 4.70 (s, 1H), 3.62-3.35 (m, 8H), 3.20 (s, 3H), 1.90 (s, 3H), 1.76 (brs, 2H).

Example 36

5-chloro-2-(4-(2,2-difluoroethyl)-1,4-diaza-1-yl)-N-(2-(S-methylsulfonimido)pyridin-4-yl)-4-(trifluoromethyl)benzamide

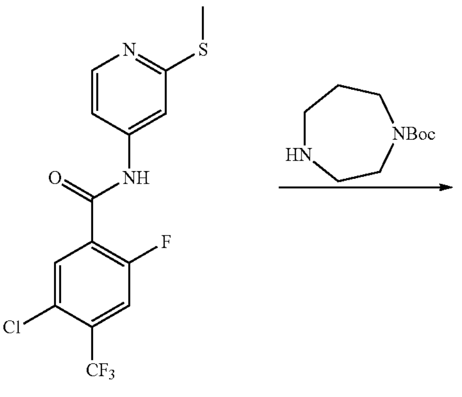

13C

-continued

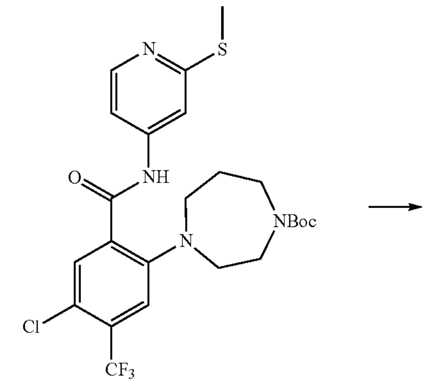

36A

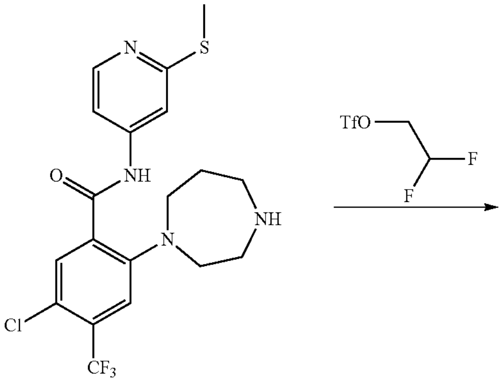

36B

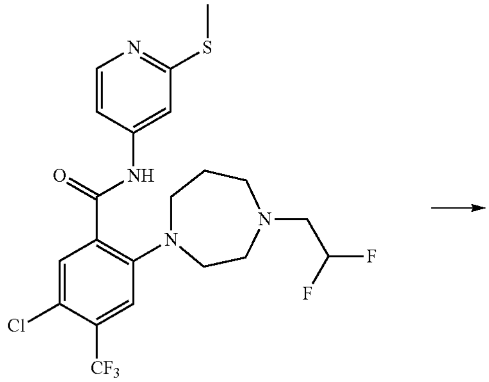

36C

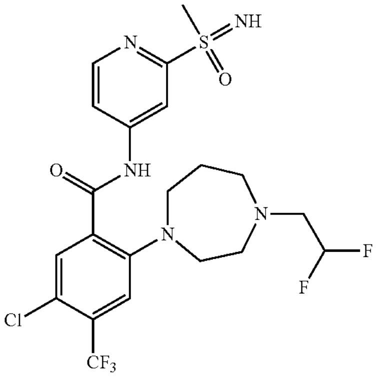

Compound 36

Step 1: Tert-butyl 4-(4-chloro-2-((2-(methylthio)pyridin-4-yl)carbamoyl)-5-(trifluoromethyl)phenyl)-1,4-diaza-1-carboxylate

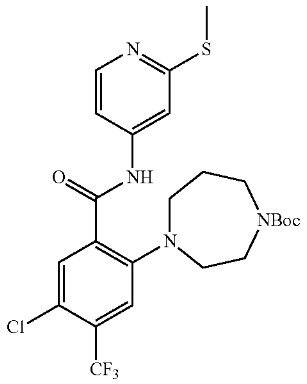 [SMILES: CSc1cc(NC(=O)c2cc(Cl)c(C(F)(F)F)cc2N2CCCN(C(=O)OC(C)(C)C)CC2)ccn1]

5-chloro-2-fluoro-N-2-methylthiopyridin-4-yl-4-trifluoromethylbenzamide (200 mg, 0.55 mmol) and tert-butyl 1,4-diaza-1-carboxylate (220.2 mg, 1.1 mmol) were dissolved in N,N-dimethylformamide (3 mL), and cesium carbonate (358.4 mg, 1.1 mmol) was added. The mixture was allowed to react in an oil bath at 100° C. for 16 hours. The reaction was stopped. The reaction solution was quenched by adding a saturated ammonium chloride solution (10 mL), and was extracted using ethyl acetate (30 mL×3). The combined organic phase was washed with a saturated saline solution (20 mL×3), dried over anhydrous sodium sulfate, and filtered. The filtrate was separated and purified by column chromatography (silica gel, petroleum ether:ethyl acetate=7:3) to obtain the title compound (215 mg, yield: 72%, yellow oil).

MS (ESI): m/z 545.1 $[M+H]^+$;

Step 2: 5-chloro-2-(1,4-diaza-1-yl)-N-(2-(methylthio)pyridin-4-yl)-4-(trifluoromethyl)benzamide

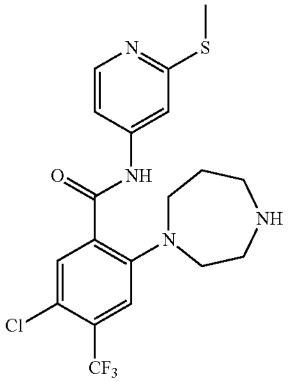 [SMILES: CSc1cc(NC(=O)c2cc(Cl)c(C(F)(F)F)cc2N2CCCNCC2)ccn1]

Tert-butyl 4-(4-chloro-2-((2-(methylthio)pyridin-4-yl)carbamoyl)-5-(trifluoromethyl)phenyl)-1,4-diaza-1-carboxylate (205 mg, 0.377 mmol) was dissolved using dichloromethane (6 mL), and trifluoroacetic acid (2 mL) was added. The mixture was allowed to react at room temperature for 1 hour. The reaction was stopped, and the mixture was spun in vacuo to remove the solvent to obtain the title compound (337 mg, yield: 98%, yellow oily matter).

MS (ESI): m/z 445.1 $[M+H]^+$;

Step 3: 5-chloro-2-(4-(2,2-difluoroethyl)-1,4-diaza-1-yl)-N-(2-(methylthio)pyridin-4-yl)-4-(trifluoromethyl)benzamide

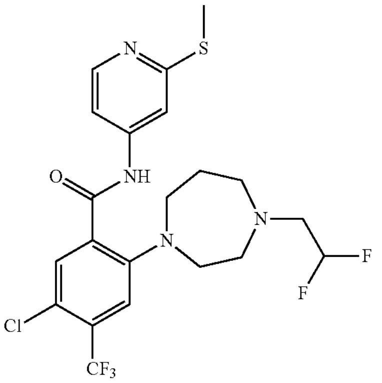 [SMILES: CSc1cc(NC(=O)c2cc(Cl)c(C(F)(F)F)cc2N2CCCN(CC(F)F)CC2)ccn1]

5-chloro-2-(1,4-diaza-1-yl)-N-(2-(methylthio)pyridin-4-yl)-4-(trifluoromethyl)benzamide (337 mg) and 2,2-difluoroethyl trifluoromethanesulfonate (96.34 mg, 0.45 mmol) were dissolved using tetrahydrofuran (1.5 mL), and triethylamine (91.5 μl) was added. The mixture was allowed to react in an oil bath at 50° C. for 16 hours. The reaction was stopped, and the mixture was spun in vacuo to remove the solvent. The residue was separated and purified by column chromatography (silica gel, petroleum ether:ethyl acetate=6.5:3.5) to obtain the title compound (148 mg, yield: 44.85%, yellow oily matter).

MS (ESI): m/z 509.1 $[M+H]^+$;

Step 4: 5-chloro-2-(4-(2,2-difluoroethyl)-1,4-diaza-1-yl)-N-(2-(S-methylsulfonimido)pyridin-4-yl)-4-(trifluoromethyl)benzamide

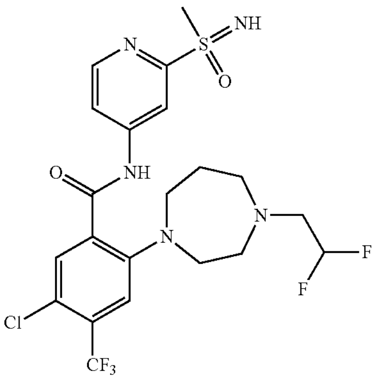 [SMILES: CS(=N)(=O)c1cc(NC(=O)c2cc(Cl)c(C(F)(F)F)cc2N2CCCN(CC(F)F)CC2)ccn1]

5-chloro-2-(4-(2,2-difluoroethyl)-1,4-diaza-1-yl)-N-(2-(methylthio)pyridin-4-yl)-4-(trifluoromethyl)benzamide (114 mg, 0.212 mmol) was dissolved using methanol (1 mL), and ammonium carbonate (11.31 mg, 0.118 mmol) and iodobenzene acetate (50.25 mg, 0.156 mmol) were added. The mixture was allowed to react at room temperature for 1 hour. The reaction was stopped, and the mixture was spun in vacuo to remove the solvent. After separation and purification by column chromatography (silica gel, petroleum ether: ethyl acetate=6.5:3.5) followed by preparation and purification by high performance liquid chromatography (elution system: ammonium bicarbonate, water, and acetonitrile), the title compound (91 mg, yield: 67.4%, yellow oily matter) was obtained.

MS (ESI): m/z 540.1 $[M+H]^+$;

Example 37

5-chloro-N-(2-methanesulfonylimino)pyridin-4-yl)-2-(4-(2,2,2-trifluoroethyl)-1,4-diazacyclopent-1-yl)-4-trifluoromethylbenzamide (Compound 37)

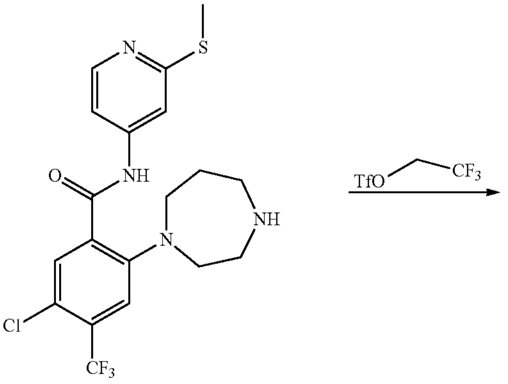

36B

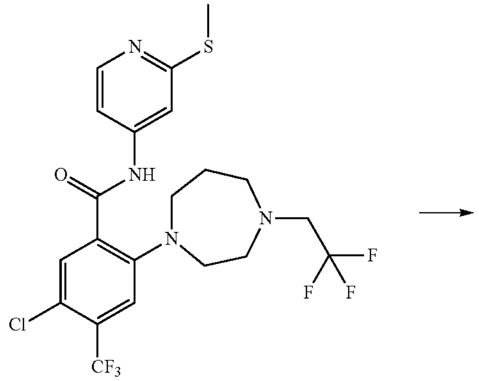

37A

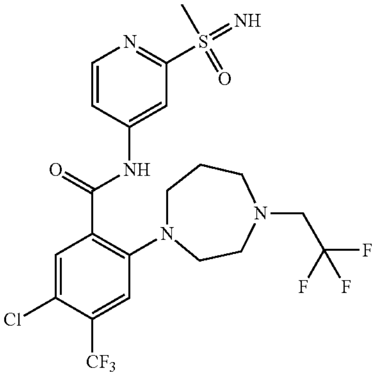

Compound 37

Step 1: 5-chloro-N-2-methylthiopyridin-4-yl-2-(2,2,2-trifluoroethyl)-1,4-diazacyclopent-1-yl)-4-trifluoromethylbenzamide

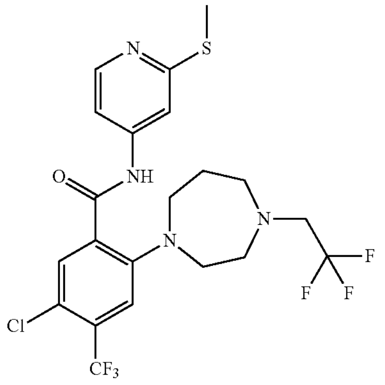 [SMILES: CSc1cc(NC(=O)c2cc(Cl)c(C(F)(F)F)cc2N2CCCN(CC(F)(F)F)CC2)ccn1]

5-chloro-2-(1,4-diazacyclopent-1-yl)-N-(2-methylthio)pyridin-4-yl)-4-trifluoromethylbenzamide (100 mg, 0.23 mmol) and 2,2,2-trifluoroethyl trifluoromethanesulfonate (208.89 mg, 0.9 mmol) were dissolved using tetrahydrofuran (2.5 mL), and triethylamine (186.19 mg, 1.84 mmol) was added. The mixture was allowed to react in an oil bath at 50° C. for 16 hours. The reaction was stopped, and the mixture was spun in vacuo to remove the solvent. The residue was separated and purified by column chromatography (silica gel, petroleum ether:ethyl acetate=7:3) to obtain the title compound (68 mg, yield: 56.7%, yellow oily matter).

MS (ESI): m/z 527.1 [M+H]$^+$;

Step 2: 5-chloro-N-(2-methanesulfonylimino)pyridin-4-yl)-2-(4-(2,2,2-trifluoroethyl)-1,4-diazacyclopent-1-yl)-4-trifluoromethylbenzamide (Compound 37)

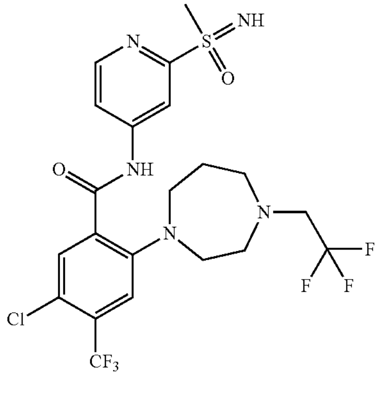 [SMILES: CS(=N)(=O)c1cc(NC(=O)c2cc(Cl)c(C(F)(F)F)cc2N2CCCN(CC(F)(F)F)CC2)ccn1]

5-chloro-N-2-methylthiopyridin-4-yl-2-(2,2,2-trifluoroethyl)-1,4-diazacyclopent-1-yl)-4-trifluoromethylbenzamide (45 mg, 0.086 mmol) was dissolved using methanol (1 mL), and ammonium carbonate (24.7 mg, 0.257 mmol) and iodobenzene acetate (110.8 mg, 0.344 mmol) were added. The mixture was allowed to react at room temperature for 1 hour. The reaction was stopped, and the mixture was spun in vacuo to remove the solvent. After separation and purification by column chromatography (silica gel, pure ethyl acetate) followed by preparation and purification by high performance liquid chromatography (elution system: ammonium bicarbonate, water, and acetonitrile), the title compound (57 mg, yield: 92.3%, yellow oily matter) was obtained.

MS (ESI): m/z 558.1 [M+H]$^+$;

Example 38

5-chloro-N-(2-((dimethyl(oxo)-$\lambda^6$-sulfanylidene)amino)pyridin-4-yl)-2-(4-fluoro-2-methylphenoxy)-4-(trifluoromethyl)benzamide (Compound 38)

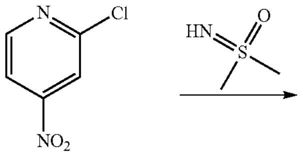

38A

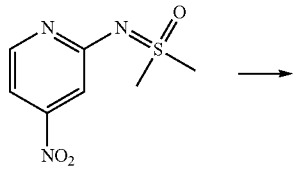

38B

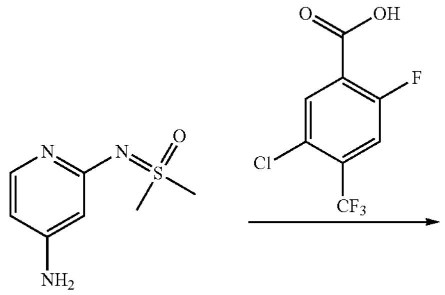

38C

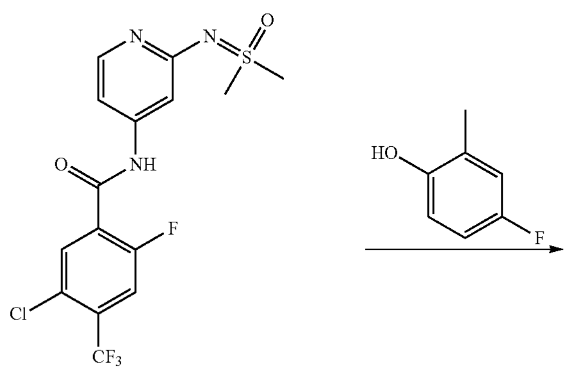

38D

-continued

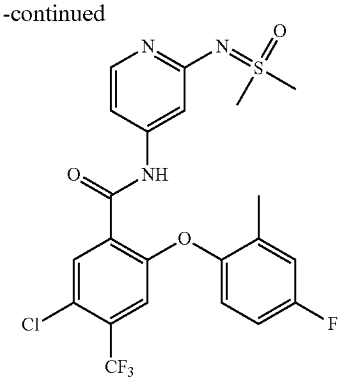

Compound 38

Step 1: (4-aminopyridin-2-yl)imino)dimethyl-6-sulfone

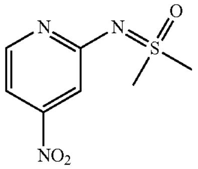

2-chloro-4-nitropyridine (1000 mg, 6.31 mmol) was dissolved using anhydrous 1,4-dioxane (20 mL), and dimethylsulfinylimine (881 mg, 9.46 mmol), cesium carbonate (6.2 g, 18.93 mmol), 4,5-bisdiphenylphosphino-9,9-dimethylxanthene (730 mg, 1.26 mmol), and tris[dibenzylideneacetone]dipalladium(0) (577 mg, 0.63 mmol) were added. The mixture was stirred and allowed to react at 100° C. overnight under nitrogen protection. The reaction was stopped. The reaction solution was spun dry, and the residue was purified by column chromatography (silica gel, petroleum ether:ethyl acetate=10:1) to obtain the title compound (1.2 g, yield: 88%, yellow solid).

MS (ESI): m/z 216.1 $[M+H]^+$;

Step 2: (4-aminopyridin-2-yl)imino)dimethyl-$\lambda^6$-sulfonamidone

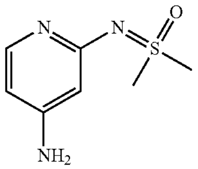

Dimethyl (4-nitropyridin-2-yl)imino)-$\lambda^6$-sulfonamidone (600 mg, 2.79 mmol) was dissolved using anhydrous methanol (10 mL), and palladium on carbon (180 mg) was added. After replacement with hydrogen, the mixture was allowed to react at room temperature for 16 hours. The reaction was stopped, and the reaction solution was filtered. The filtrate was spun in vacuo to remove the solvent, and the residue was separated and purified by column chromatography (silica gel, petroleum ether:ethyl acetate=1:1) to obtain the title compound (460 mg, yield: 89%, white solid). MS (ESI): m/z 186.2 $[M+H]^+$;

Step 3: 5-chloro-N-(2-((dimethyl(oxo)-$\lambda^6$-sulfaneylidene)amino)pyridin-4-yl)-2-fluoro-4-(trifluoromethyl)benzamide

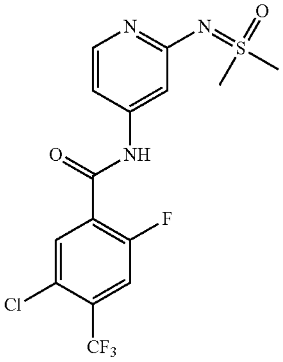 [SMILES: CS(C)(=O)=Nc1cc(NC(=O)c2cc(Cl)c(C(F)(F)F)cc2F)ccn1]

(4-aminopyridin-2-yl)imino)dimethyl-$\lambda^6$-sulfonamidone (120 mg, 0.648 mmol) and 5-chloro-2-fluoro-4-(trifluoromethyl)benzoic acid (157.17 mg, 0.648 mmol) were dissolved using pyridine (2 mL). After replacement with nitrogen, the temperature was decreased to −10° C., and phosphorus oxychloride (248.64 mg, 1.62 mmol) was added. The mixture was allowed to react at room temperature for 2 hours. The reaction was stopped. The reaction solution was quenched by adding ice water (5 mL), adjusted to be acidic by using 1 N hydrochloric acid, and extracted using ethyl acetate (20 mL×3). The combined organic phase was washed with a saturated saline solution (20 mL×3), dried over anhydrous sodium sulfate, and filtered. The filtrate was spun in vacuo to remove the solvent, and the residue was separated and purified by column chromatography (silica gel, dichloromethane:anhydrous methanol=9:1) to obtain the title compound (263.7 mg, yield: 98%, yellow oily matter).

MS (ESI): m/z 410.0 $[M+H]^+$;

Step 4: 5-chloro-N-(2-((dimethyl(oxo)-$\lambda^6$-sulfanylidene)amino)pyridin-4-yl)-2-(4-fluoro-2-methylphenoxy)-4-(trifluoromethyl)benzamide (Compound 38)

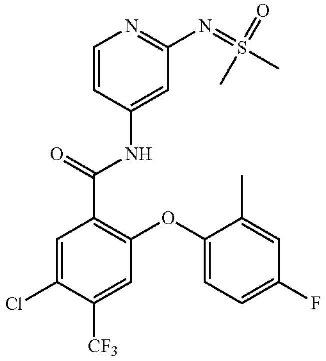 [SMILES: Cc1cc(F)ccc1Oc1cc(C(F)(F)F)c(Cl)cc1C(=O)Nc1ccnc(N=S(C)(C)=O)c1]

5-chloro-N-(2-((dimethyl(oxo)-$\lambda^6$-sulfaneylidene)amino)pyridin-4-yl)-2-fluoro-4-(trifluoromethyl)benzamide (132 mg, 0.324 mmol) and 4-fluoro-2-methylphenol (81.64 mg, 0.65 mmol) were dissolved using N,N-dimethylformamide (2 mL), and cesium carbonate (316.7 mg, 0.972 mmol) was added. The mixture was allowed to react in an oil bath at 100° C. for 2 hours. The reaction was stopped. The reaction solution was filtered, and was then purified by preparative high performance liquid chromatography (elution system: ammonium bicarbonate, water, and acetonitrile) to obtain the title compound (38.25 mg, yield: 22.9%, white solid).

MS (ESI): m/z 516.1 $[M+H]^+$;

$^1$H NMR (400 MHz, DMSO-$d_6$) δ 10.71 (s, 1H), 8.03 (s, 1H), 7.99 (d, J=5.7 Hz, 1H), 7.21 (d, J=9.0 Hz, 1H), 7.10-7.08 (m, 4H), 7.03 (d, J=5.7 Hz, 1H), 6.93 (s, 1H), 3.34 (s, 3H), 3.32 (s, 3H), 2.16 (s, 3H).

Example 39

5-chloro-2-(4,4-difluoroazepan-1-yl)-N-(2-((dimethyl(oxo)-$\lambda^6$-sulfaneylidene)amino)pyridin-4-yl)-4-(trifluoromethyl)benzamide (Compound 39)

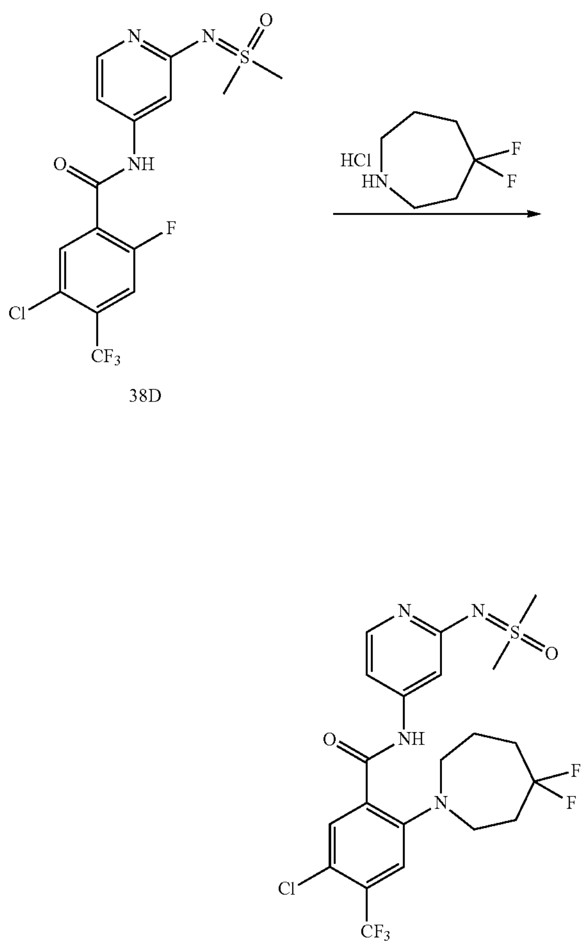

38D

Compound 39

5-chloro-N-(2-((dimethyl(oxo)-$\lambda^6$-sulfaneylidene)amino)pyridin-4-yl)-2-fluoro-4-(trifluoromethyl)benzamide (132 mg, 0.324 mmol) and 4,4-difluoroazetidine hydrochloride (322.4 mg, 1.944 mmol) were dissolved using N,N-dimethylformamide (2 mL), and cesium carbonate (1.056 g, 3.24 mmol) was added. The mixture was allowed to react in an oil bath at 100° C. for 16 hours. The reaction was stopped. The reaction solution was filtered, and the filtrate was purified by preparative high performance liquid chromatography (elution system: ammonium bicarbonate, water, and acetonitrile) to obtain the title compound (39.52 mg, yield: 23.3%, yellow solid).

MS (ESI): m/z 525.1 $[M+H]^+$;

$^1$H NMR (400 MHz, DMSO-$d_6$) δ 10.66 (s, 1H), 7.99 (d, J=5.5 Hz, 1H), 7.64 (s, 1H), 7.33 (s, 1H), 7.03 (d, J=8.8 Hz, 2H), 3.41-3.34 (m, 10H), 2.23 (brs, 2H), 2.10-2.01 (m, 2H), 1.80-1.78 (m, 2H).

Biological Test Evaluation

Test Example A: Blocking activity of the compound of the present invention on sodium ion channel 1.8 (Nav1.8)

Experimental objective: to determine the rate of inhibition of the compound on the human Nav1.8 ion channel stably expressed by CHO cells

Experimental Method

The compound was dissolved using DMSO to prepare a stock solution. The stock solution was diluted with an extracellular fluid (140 mM NaCl, 3.5 mM KCl, 1 mM MgCl2, 2 mM CaCl2), 10 mM D-glucose, 10 mM HEPES, 1.25 mM NaH2PO4 2H2O, pH=7.4 (NaOH)) to particular concentrations to be used in manual patch clamp testing.

A capillary glass tube was stretched to form a recording electrode using a microelectrode puller. A microelectrode manipulator was operated under an inverted microscope to contact the recording electrode to the cells, and negative suction pressure was applied to form a GQ seal. Once the GQ seal was formed, rapid capacitance compensation was performed, and then the negative pressure was continued to break the cell membrane, forming a whole cell recording mode. Slow capacitance was compensated for, and the film capacitance and series resistance were recorded. No leakage compensation was applied. Once the Nav1.8 current recorded in the whole cell was stabilized, administration of the compound was started. The compound was allowed to act at the first concentration for 5 min (or until the electric current stabilized), and then the second concentration was tested. For each test compound, two concentrations were tested.

The voltage stimulation protocol for whole-cell patch clamp recording of Nav1.8 sodium current was as follows: once the whole cell seal was formed, the cellular voltage was clamped at −120 mV for 30 ms. The clamping voltage was depolarized to 0 mV for 50 ms, and then the voltage was restored to −50 mV (for the specific voltage, reference was made to the half inactivation voltage in IV testing) for 8 s. Subsequently, the cell membrane potential was restored to −120 mV for 20 ins, then further depolarized to 0 mV for 50 ins, and finally restored to the clamping voltage of −120 mV for 30 ins. Data acquisition was repeated every 20 s. The effect of the compound on the peak value of the sodium current was observed. The experimental data was collected by an EPC-10 amplifier (HEKA) and was stored in PatchMaster (HEKA) software.

Experimental Results

| Compound number | Inhibition rate (%) @ 10 nM | Inhibition rate (%) @ 100 nM |
|---|---|---|
| Compound 1 | 59.80% | 91.30% |
| Compound 2 | 84.51% | 100% |
| Compound 3 | 92.00% | 98.41% |
| Compound 4 | 84.93% | 96.11% |
| Compound 5 | 78.46% | 96.77% |
| Compound 6 | 71.27% | 98.07% |
| Compound 7 | 91.54% | 97.11% |
| Compound 8 | 68.58% | 93.04% |
| Compound 9 | 60.11% | 95.23% |
| Compound 10 | 46.21% | 83.42% |
| Compound 11 | 80.53% | 97.78% |
| Compound 12 | 71.54% | 97.91% |
| Compound 13 | 52.36% | 97.24% |
| Compound 14E1 | 62.25% | 88.27% |
| Compound 14E2 | 77.64% | 97.96% |
| Compound 15 | 86.33% | 99.28% |
| Compound 17 | 71.90% | 96.51% |
| Compound 17E1 | 75.68% | 97.45% |
| Compound 17E2 | 69.40% | 97.09% |
| Compound 20 | 46.84% | 86.49% |
| Compound 23E1 | 65.27% | 95.52% |
| Compound 23E2 | 79.81% | 97.38% |
| Compound 24 | 83.91% | 99.00% |
| Compound 25 | 82.04% | 95.49% |
| Compound 27 | 75.14% | 95.95% |
| Compound 27E1 | 62.99% | 96.01% |
| Compound 27E2 | 79.57% | 97.20% |

Test Example B: Quantitative pharmacokinetic evaluation of the compound of the present invention administered by intravenous injection or gavage in rats.

Experimental objective: The object of this test example was to evaluate the pharmacokinetic properties of the compound of the present invention.

The present inventors conducted pharmacokinetic evaluation of the compound of the present invention in rats. The animal information is shown in Table 2.

TABLE 2

Table of information of the test animals in the present invention

| Germline | Grade | Sex | Weight | Age | Source |
|---|---|---|---|---|---|
| SD Rat | SPF | Male | 180-220 g | 6-8 weeks | Shanghai Sippr-BK Laboratory Animals Co., Ltd. |

Experimental Method

The compound of the present invention was administered to the test animals as a solution of 5% DMSO+5% tween 80+90% physiological saline solution. The animals were fasted for 12 hours prior to the administration, but had free access to water. For the intravenous injection administration group, the administration dose was 1 mg/kg; for gavage administration, the administration dose was 10 mg/kg. Following administration, blood was intravenously collected from the animals (approximately 0.3 mL of blood) at the following time points: 0.083 h, 0.25 h, 0.5 h, 1.0 h, 2.0 h, 4.0 h, 8.0 h, and 24 h. The blood collection tubes previously had EDTA-K2 added thereto as an anticoagulant. Each blood sample was centrifuged at 6800 g at a low temperature for 6 minutes, and plasma was collected and stored at −80° C.

Sample preparation for LC-MS/MS assay: 20 µL of the plasma sample was subjected to protein precipitation using 400 µL of methanol containing 100 ng/mL of IS (tolbutamide). The mixture was vortexed for 1 minute and then centrifuged at 18000 g for 7 minutes. 400 µL of the supernatant was transferred to a 96-well plate. 2 µL of the supernatant were subjected to LC-MS/MS analysis. The analysis results showed that the compound of the present invention had good pharmacokinetic properties in rats.

| Group | Test compound | Dose (mg/kg) | Tmax (h) | Cmax (ng/ml) | AUClast (h*ng/ml) | $T_{1/2}$ (h) | Cl (mL/min/kg) | Vz (L/kg) | F (%) |
|---|---|---|---|---|---|---|---|---|---|
| Intravenous administration group | Compound 13 | 1 | 0.08 | 496 | 2239 | 3.88 | 7.52 | 2.48 | \ |
| | Compound 17E1 | 1 | 0.08 | 653 | 3832 | 3.95 | 4.33 | 1.47 | \ |
| | Compound 17E2 | 1 | 0.08 | 659 | 2784 | 4.29 | 6.14 | 2.19 | \ |
| | Compound 27E1 | 1 | 0.08 | 727 | 1003 | 1.92 | 16.28 | 2.61 | \ |
| | Compound 27E2 | 1 | 0.08 | 577 | 1904 | 4.13 | 8.63 | 3.07 | \ |
| Gavage administration group | Compound 13 | 10 | 2.67 | 1837 | 18624 | 3.85 | \ | \ | 83.19 |
| | Compound 17E1 | 10 | 1.33 | 2789 | 28224 | 3.92 | \ | \ | 73.64 |
| | Compound 17E2 | 10 | 1.00 | 2590 | 18445 | 2.93 | \ | \ | 66.25 |
| | Compound 27E1 | 10 | 1.00 | 1837 | 6908 | 1.91 | \ | \ | 68.85 |
| | Compound 27E2 | 10 | 1.00 | 1561 | 11584 | 2.74 | \ | \ | 60.83 |

Test Example C: Quantitative pharmnacokinetic evaluation of the compound of the present invention administered by intravenous injection or gavage in mice Experimental objective: The object of this test example was to evaluate the pharmacokinetic properties of the compound of the present invention.

The present inventors conducted pharmnacokinetic evaluation of the compound of the present invention in mice. The animal information is shown in Table 3.

TABLE 3

Table of information of the test animals in the present invention

| Germline | Grade | Sex | Weight | Age | Source |
|---|---|---|---|---|---|
| ICR mice | SPF | Male | 26-32 g | 6-8 weeks | Shanghai Sippr-BK Laboratory Animals Co., Ltd. |

Experimental Method

The compound of the present invention was administered to the test animals as a solution of 5% DMSO+5% tween 80+90% physiological saline medium. The animals were fasted for 12 hours prior to the administration, but had free access to water. For the intravenous injection administration group, the administration dose was 1 mg/kg; for gavage administration, the administration dose was 10 mg/kg. Following administration, blood was intravenously collected from the animals (approximately 0.3 mL of blood) at the following time points: 0.083 h, 0.25 h, 0.5 h, 1.0 h, 2.0 h, 4.0 h, 8.0 h, and 24 h. The blood collection tubes previously had EDTA-K2 added thereto as an anticoagulant. Each blood sample was centrifuged at 6800 g at a low temperature for 6 minutes, and plasma was collected and stored at −80° C.

Sample preparation for LC-MS/MS assay: 15 µL of the plasma sample was subjected to protein precipitation using 300 μL of methanol containing 100 ng/mL of IS (tolbutamide). The mixture was vortexed for 1 minute and then centrifuged at 18000 g for 10 minutes. 300 μL of the supernatant was transferred to a 96-well plate. 2 μL of the supernatant were subjected to LC-MS/MS analysis. The analysis results showed that the compound of the present invention had good pharmacokinetic properties in mice.

| Group | Test compound | Dose (mg/kg) | Tmax (h) | Cmax (ng/ml) | AUClast (h*ng/ml) | $T_{1/2}$ (h) | Cl (mL/min/kg) | Vz (L/kg) | F (%) |
|---|---|---|---|---|---|---|---|---|---|
| Intravenous administration group | Compound 23E2 | 1 | 0.08 | 624 | 1874 | 2.62 | 8.94 | 2.01 | \ |
| Gavage administration group | Compound 23E2 | 10 | 1.33 | 2123 | 23559 | 2.14 | \ | \ | 125.68 |

The invention claimed is:

1. A compound having the structure of:

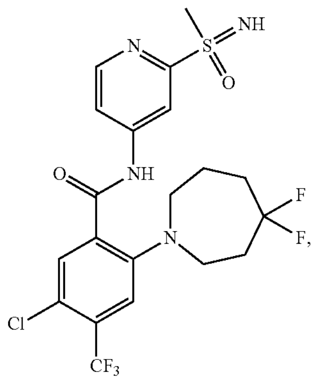 [SMILES: CS(=N)(=O)c1cc(NC(=O)c2cc(Cl)c(C(F)(F)F)cc2N2CCCC(F)(F)CC2)ccn1]

or a pharmaceutically acceptable salt thereof.

2. A compound having the structure of:

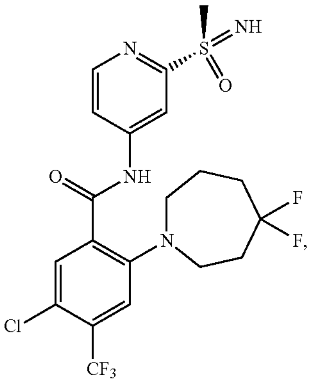 [SMILES: C[S@@](=N)(=O)c1cc(NC(=O)c2cc(Cl)c(C(F)(F)F)cc2N2CCCC(F)(F)CC2)ccn1]

or a pharmaceutically acceptable salt thereof.

3. A compound having the structure of:

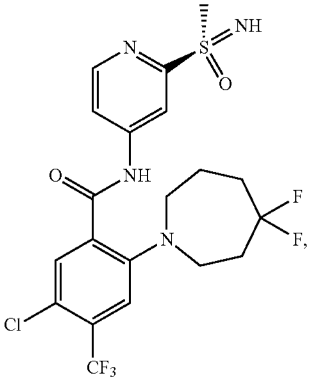 [SMILES: C[S@](=N)(=O)c1cc(NC(=O)c2cc(Cl)c(C(F)(F)F)cc2N2CCCC(F)(F)CC2)ccn1]

or a pharmaceutically acceptable salt thereof.

4. A pharmaceutical composition comprising the compound of claim 1, or a pharmaceutically acceptable salt thereof, and a pharmaceutically acceptable excipient.

5. A pharmaceutical composition comprising the compound of claim 2, or a pharmaceutically acceptable salt thereof, and a pharmaceutically acceptable excipient.

6. A pharmaceutical composition comprising the compound of claim 3, or a pharmaceutically acceptable salt thereof, and a pharmaceutically acceptable excipient.

* * * * *